(12) United States Patent  (10) Patent No.: US 7,493,160 B2
Weber et al.  (45) Date of Patent: Feb. 17, 2009

(54) NANO-ACTUATED MEDICAL DEVICE

(75) Inventors: Jan Weber, Maple Grove, MN (US);
Thomas Holman, Princeton, MN (US);
Tracee E. J. Eidenschink, Wayzata, MN (US); John J. Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 745 days.

(21) Appl. No.: 10/679,049

(22) Filed: Oct. 3, 2003

(65) Prior Publication Data

US 2004/0138733 A1 Jul. 15, 2004

Related U.S. Application Data

(63) Continuation-in-part of application No. 10/270,815, filed on Oct. 15, 2002, now Pat. No. 7,037,319.

(51) Int. Cl.
*A61M 1/18* (2006.01)

(52) U.S. Cl. .......................................................... 607/3

(58) Field of Classification Search ......... 606/191–198, 606/1, 18; 623/1.1, 1.11; 607/2, 3, 1, 72, 607/74
See application file for complete search history.

(56) References Cited

U.S. PATENT DOCUMENTS

| | | | |
|---|---|---|---|
| 4,273,128 A | 6/1981 | Lary | |
| 4,522,194 A * | 6/1985 | Normann | 600/18 |
| 4,765,332 A | 8/1988 | Fischell et al. | |
| 4,926,858 A | 5/1990 | Gifford, III et al. | |
| 4,954,388 A | 9/1990 | Mallouk et al. | |
| 4,963,313 A | 10/1990 | Noddin et al. | |
| 4,979,951 A | 12/1990 | Simpson | |
| 5,047,040 A | 9/1991 | Simpson et al. | |
| 5,049,131 A | 9/1991 | Deuss | |
| 5,092,872 A | 3/1992 | Segalowitz | |
| 5,209,728 A | 5/1993 | Kraus et al. | |
| 5,234,450 A | 8/1993 | Segalowitz | |
| 5,300,203 A | 4/1994 | Smalley | |
| 5,320,634 A | 6/1994 | Vigil et al. | |
| 5,336,234 A | 8/1994 | Vigil et al. | |
| 5,397,308 A | 3/1995 | Ellis et al. | |

(Continued)

FOREIGN PATENT DOCUMENTS

WO   WO 93/11190   6/1993

(Continued)

OTHER PUBLICATIONS

International Search Report for PCT/US03/31482 mailed Jul. 16, 2004.

(Continued)

*Primary Examiner*—Kevin T Truong
(74) *Attorney, Agent, or Firm*—Crompton, Seager & Tufte LLC

(57) ABSTRACT

A medical device is disclosed which may include the use of nanopaper. The medical device may be provided in the form of a balloon catheter wherein the nanopaper is mounted about an electrode and into which an electrically conductive solution is dispersed. An elastomeric sheath may then be provided about the nanopaper. Actuation of the electrode may cause generation of microbubbles causing the nanopaper to expand.

10 Claims, 45 Drawing Sheets

U.S. PATENT DOCUMENTS

| | | |
|---|---|---|
| 5,401,587 A | 3/1995 | Motohiro et al. |
| 5,415,634 A | 5/1995 | Glynn et al. |
| 5,424,054 A | 6/1995 | Bethune et al. |
| 5,490,837 A | 2/1996 | Blaeser et al. |
| 5,538,585 A | 7/1996 | Wakita et al. |
| 5,543,378 A | 8/1996 | Wang |
| 5,549,807 A | 8/1996 | Bell et al. |
| 5,591,312 A | 1/1997 | Smalley |
| 5,616,149 A | 4/1997 | Barath |
| 5,645,564 A | 7/1997 | Northrup et al. |
| 5,715,832 A | 2/1998 | Koblish et al. |
| 5,792,158 A | 8/1998 | Lary |
| 5,853,886 A | 12/1998 | Pinnavaia et al. |
| 5,873,907 A | 2/1999 | Frantzen |
| 5,916,642 A | 6/1999 | Chang |
| 5,919,145 A | 7/1999 | Sahatjian |
| 6,019,656 A | 2/2000 | Park et al. |
| 6,042,959 A | 3/2000 | Debe et al. |
| 6,056,720 A | 5/2000 | Morse |
| 6,074,773 A | 6/2000 | Wilkinson et al. |
| 6,080,170 A | 6/2000 | Nash et al. |
| 6,090,135 A | 7/2000 | Plaia et al. |
| 6,096,054 A | 8/2000 | Wyzgala et al. |
| 6,110,192 A | 8/2000 | Ravenscroft et al. |
| 6,135,991 A | 10/2000 | Muni et al. |
| 6,136,258 A | 10/2000 | Wang et al. |
| 6,149,775 A | 11/2000 | Tsuboi et al. |
| 6,152,938 A | 11/2000 | Curry et al. |
| 6,183,714 B1 | 2/2001 | Smalley et al. |
| 6,258,108 B1 | 7/2001 | Lary |
| 6,302,906 B1 | 10/2001 | Goicoechea et al. |
| 6,319,242 B1 | 11/2001 | Patterson et al. |
| 6,346,023 B1 | 2/2002 | Tsuboi et al. |
| 6,347,247 B1 * | 2/2002 | Dev et al. ............... 607/2 |
| 6,387,560 B1 | 5/2002 | Yadav et al. |
| 6,425,908 B2 | 7/2002 | Ravenscroft et al. |
| 6,425,914 B1 | 7/2002 | Wallace et al. |
| 6,447,478 B1 | 9/2002 | Maynard |
| 6,458,128 B1 | 10/2002 | Schulze |
| 6,468,266 B1 | 10/2002 | Bashiri et al. |
| 6,530,948 B1 | 3/2003 | Vrba |
| 6,545,384 B1 | 4/2003 | Pelrine et al. |
| 6,555,945 B1 | 4/2003 | Baughman et al. |
| 6,576,365 B1 | 6/2003 | Meitav et al. |
| 6,585,753 B2 | 7/2003 | Eder et al. |
| 6,589,682 B1 | 7/2003 | Fleckner et al. |
| 6,592,568 B2 | 7/2003 | Campbell |
| 6,607,551 B1 | 8/2003 | Sullivan et al. |
| 6,626,934 B2 | 9/2003 | Blaeser et al. |
| 2002/0062122 A1 | 5/2002 | Lehmann et al. |
| 2002/0068170 A1 | 6/2002 | Smalley et al. |
| 2002/0122766 A1 | 9/2002 | Lieber et al. |
| 2002/0179434 A1 | 12/2002 | Dai et al. |
| 2003/0032892 A1 | 2/2003 | Erlach et al. |
| 2003/0055407 A1 | 3/2003 | Walik |
| 2003/0065355 A1 | 4/2003 | Weber |
| 2003/0068432 A1 | 4/2003 | Dai et al. |
| 2003/0093107 A1 | 5/2003 | Parsonage et al. |
| 2003/0133865 A1 | 7/2003 | Smalley et al. |
| 2003/0135971 A1 | 7/2003 | Liberman et al. |
| 2003/0143350 A1 | 7/2003 | Jimenez |
| 2003/0171257 A1 | 9/2003 | Stirbl et al. |
| 2003/0180472 A1 | 9/2003 | Zhou et al. |
| 2003/0185985 A1 | 10/2003 | Bronikowski et al. |

FOREIGN PATENT DOCUMENTS

| | | |
|---|---|---|
| WO | WO 01/34685 | 5/2001 |
| WO | WO 02/082974 | 10/2002 |
| WO | WO-03/026532 A2 | 4/2003 |
| WO | WO-03/049795 A2 | 6/2003 |

OTHER PUBLICATIONS

Partial International Search Report PCT/US 03/31482; report dated Apr. 27, 2004.

"Energetics and Structure of Single Walled Carbon Nanotoroids," Gao et al., California Institute of Technology, 11 pages (2002).

"Elastic Properties of Carbon Nanotubes and Nanoropes," Jian Ping Lu, Physical Review Letters, vol. 79: No. 7, 1297-1300 (1997).

"Carbon Nanotube (A big revolution in a technology that thinks, very, very, very small)," Meyyappan et al., IEEE Potentials, 16-18 (2000).

"Large-scale purification of single-wall carbon nanotubes: process, product, and characterization," Rinzler et al., Appl. Phys. A 67, 29-37 (1998).

"Pneumatic Actuator Response from Carbon Nanotube Sheets," Spinks et al., Intellectual Polymer Research Institute, University of Wollongong, Mat. Res. Soc. Proc. vol. 706:8-13 (2002).

"Alternative Formulations for the Anti-Cancer Drug Paclitaxel (Taxol)," Adriance-Meja et al., 2002.

"Sustained Release Properties of Polyelectrolyte Multilayer Capsules," Antipov et al., J. Phys. Chem., 105:2281-2284 (2001).

"Organic Solvent Dispersions of Single-Walled Carbon Nanotubes: Toward Solutions of Pristine Nanotubes," Ausman et al., J. Phys. Chem, 104:8911-8915 (2000).

"Functionalization of Carbon Nanotubes by Electrochemical Reduction of Aryl Diazonium Salts: A Bucky Paper Electrode," Bahr et al., J. Am. Chem. Soc., 123:6536-6542 (2001).

"Carbon Nanotubes—The Route Toward Applications," Baughman et al., 297:787-792 (2002).

"Carbon Nanotube Actuators," Baughmann et al., Science, 284:1340-1644 (1999).

"Conducting Polymer Artificial Muscles," Baughman, R., Syn. Metals, 78:339-353 (1996).

"Albumin-Heparin Matrices Loaded with Growth Factor as Substrates for Endothelial Cell Seeding," Bos, G., Thesis, University of Twente, The Netherlands, 1968.

"Polymers in Controlled Drug Delivery," Brannon-Peppas, L., Medical Device Link, 1997.

"Use of Commercial Porous Ceramic Particles for Sustained Drug Delivery," Byme et al., Int. J. Pharmaceutics, 246:61-73 (2002).

"Plasma Activation of Carbon Nanotubes for Chemical Modification," Chen et al., J. Phys. Chem., 105:618-622 (2001).

"Steerable Microcatheters Actuated by Embedded Conducting Polymer Science," Della Santa et al., J. Intell., Mater. Sys. Struct., 7:292-300 (1996).

"Chemical Functionalization of Single Walled Carbon Nanotubes," Dettlaff-Weglikowska et al., Curr. Appl. Phys., 2:497-507 (2002).

"Organic Functionalization of Carbon Nanotubes," Georgakilas et al., J. Am. Chem., 124:760-761 (2002).

"Special Delivery. Alternative Methods for Delivering Drugs Improve Performance, Convenience, and Patient Compliance," Henry et al., Science/Technology, 78:49-65 (2000).

"Supramolecular Structures of Novel Carbohydrate-Based Phospholipids," Hird et al., J. Am. Chem. Soc., 122:8097-8098 (2000).

"Chemical and Physiochemical Characterization of Porous Hydroxyapatite Ceramics Made of Natural Bone," Joschek et al., Biomaterials, 21:1645-1658 (2000).

"Ion-Irradiation-Induced Welding of Carbon Nanotubes," Krasheninnikov et al., Phys. Rev., 66:245403-1-245403-6.

"Fullerene Pipes," Liu et al., Science, 280:1253-1256 (1998).

"Carbon Nanotube Bucky Paper Scaffold for Retinal Cell Transplantation," Loftus, D., NASA (2003).

"PVDF-Based Proton Conducting Membranes as Electrolytes for Polymer Fuel Cells," Magistris et al., XXI Congresso Nazionale Della Societa' Chimica Italiana, (2003).

"Structures of High-Stage Donor-Acceptor Hetero-Structure Graphite Intercalation Compounds," Murakami et al., J. Phys. Soc. Japan, 59:571-578 (1990).

"The Expansion of the Carbon-Carbon Bond Length in Potassium Graphites," Nixon et al., J. Phys. C., 2:1732-1741 (1969).

"Synthesis, Structural Characterization, and Immunological Properties of Carbon Nanotubes Functionalized with Peptides," Pantarotto et al., J. Am. Chem., 125:6160-6164 (2003).

"Studies on the Drug Release Properties of Polysaccharide Multilayers Encapsulated Ibuprofen Microparticles," Qiu et al., Langmuir, 17:5375-5380 (2001).

"Elastic and Shear Moduli of Single-Walled Carbon Nanotube Ropes," Salvetat et al., Phys. Rev. Lett., 82:944-947 (1999).

"Electrochemical Muscles: Micromachining Fingers and Corkscrews," Smela et al., Adv. Mater., 5:630-632 (1993).

"Single-Wall Carbon Nanotube Films," Sreekumar et al., Chem. Mater., 15:175-178 (2003).

"Shape Memory Alloys: Functional and Smart," Stalmans et al., in Smart Materials and Technologies—Sensors, Control Systems and Regulators, Prague, Czech Republic, 1995.

"Gummy Drug Delivery," Stover, D., Popular Science, 2000.

"Mono-sized and Single Walled 4 A Carbon Nanotubes," Wang et al., Chem. Phys. Lett., 339:47-52(2001).

"Giant Electrostriction and Relaxor Ferroelectric Behavior in Electron-Irradiated Poly(vinylidene fluoride-trifluoroethylene) Copolymer," Zhang et al., Science, 280:2010-2104 (1998).

"Crystallization and Microstructure Analysis of Calcium Phosphate-Based Glass Ceramics for Biomedical Applications," Zhang et al., J. Non-Crystalline Solids, 272:14-21 (2000).

"Transport Properties of Triblock Copolymer Ionomer Membranes for Fuel Cells," U.S. Research Laboratory.

"Polymer Gel Holds Promise for Therapeutics Delivery and Tissue Engineering," EurekaAlert, www.eurekalert.org/pub_releases/2001-03/PNNL-Pghp-2803101.php.

"Smart Capsules," in *Multilater Thin Films*, Chapter 13, 2003.

Electrochem Membrane Materials.

Foils List, Lebow Co.

Argonide Website.

Zyvex website.

GFD-Diamond website.

Macromed Website.

"Carbon Nanotubes as Actuators in Smart Structures," Monner et al., Proceedings of the SPIE-The International Society for Optical Engineering, vol. 5053, pp. 138-146.

"Carbon Nanotube/Polyelectrolyte Composites as Novel Actuator Materials," Chattopadhyay et al., Nanotubes and Related Materials, Symposium (Mater. Res. Soc. Symposium Proceedings, vol. 6363, p. A13.39, 1-6 (2001).

"Single Wall Carbon Nanotube—Nafion Composite Actuators," Landi et al., Nano Letters, vol. 2, No. 11, pp. 1329-1332, American Chem. Soc. ( Nov. 2002).

"Practical Considerations for the Demonstration of Single Walled Carbon Nanotube Actuator," Minett et al., AIP Conference Proceedings Conference, AIP Cof. Proc. (USA), No. 591, pp. 585-589 (2001).

"Work Functions of Pristine and Alkali-Metal Intercalated Carbon Nanotubes and Bundles," Jijun et al., Physical Review B (Condensed Matter and Materials Physics), vol. 65, No. 19, pp. 193401/1-4 (May 15, 2002).

"The Effect of Solvent on Electrical Transport Properties in Single-Wall Carbon Nanotubes," Masubuchi et al., AIP Conference Proceedings Conference, AIP Conf. Proc. (USA), No. 590, pp. 233-236 (2001).

"Effect of Polymer and Solvent on Purification and Cutting of Single-Wall Carbon Nanotubes," Zhang et al., Chemical Physics Letters, vol. 349, No. 1-2, pp. 25-30 (Nov. 23, 2001).

"Pneumatic Carbon Nanotube Actuators," Spinks et al., Advanced Materials, vol. 14, No. 23, Dec. 3, 2002, pp. 1728-1732 (2002).

"Electrochemical Properties of Aligned Nanotube Arrays: Basis of New Electromechanical Actuators", Gao et al., Proceedings of the SPEI—The International Society for Optical Engineering, vol. 3987, pp. 18-24 (2000).

"Neutron-Diffraction Studies of $BaC_6$: $c$-Axis Compressibility, Carbon—Carbon Bond Length, and Charge Transfer," Fischer et al., Physical Review B, vol. 36, No. 8 (Sep. 15, 1987).

* cited by examiner

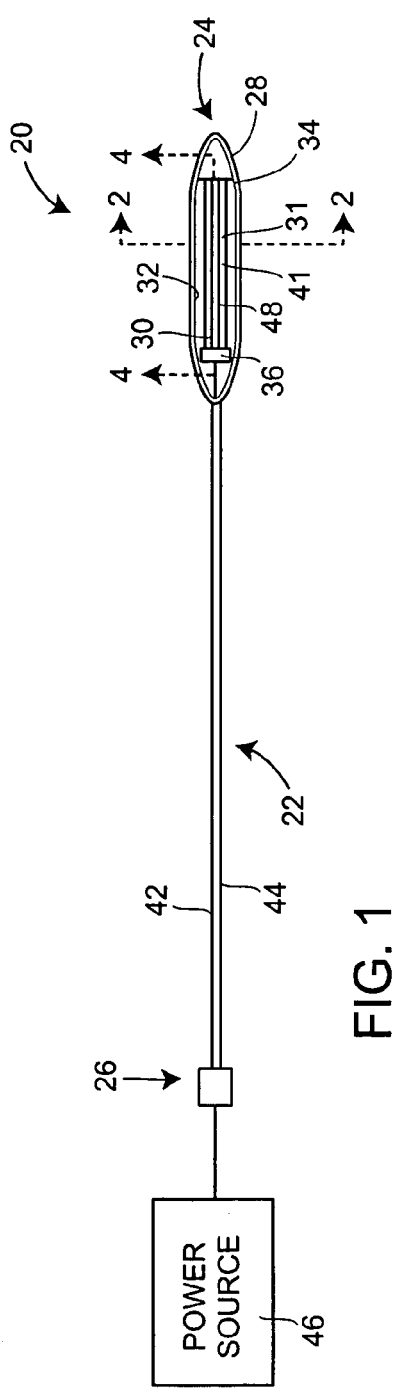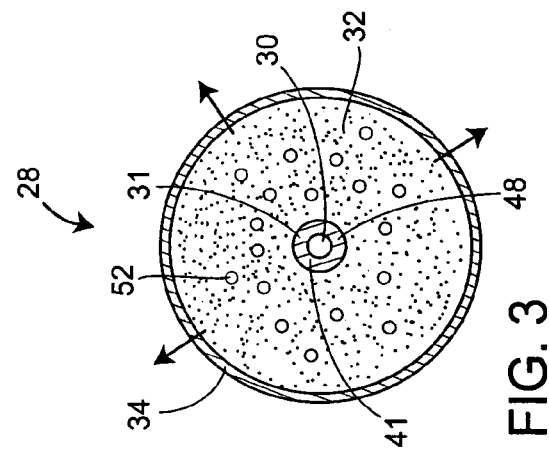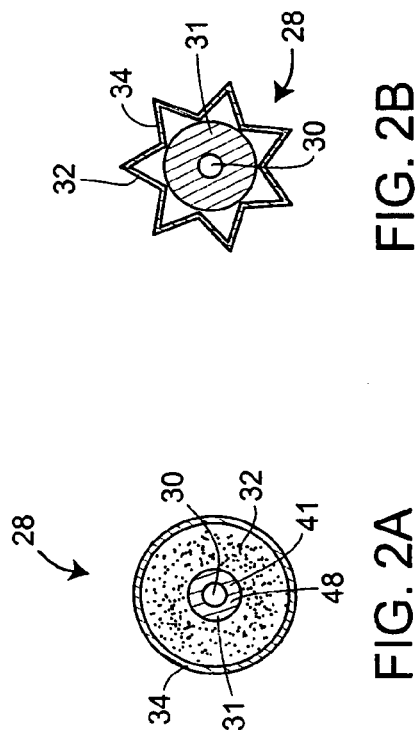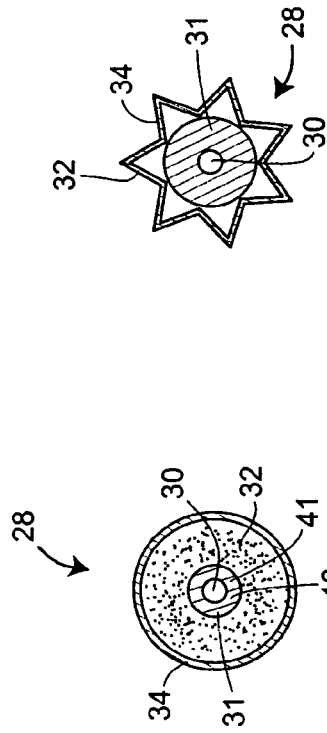

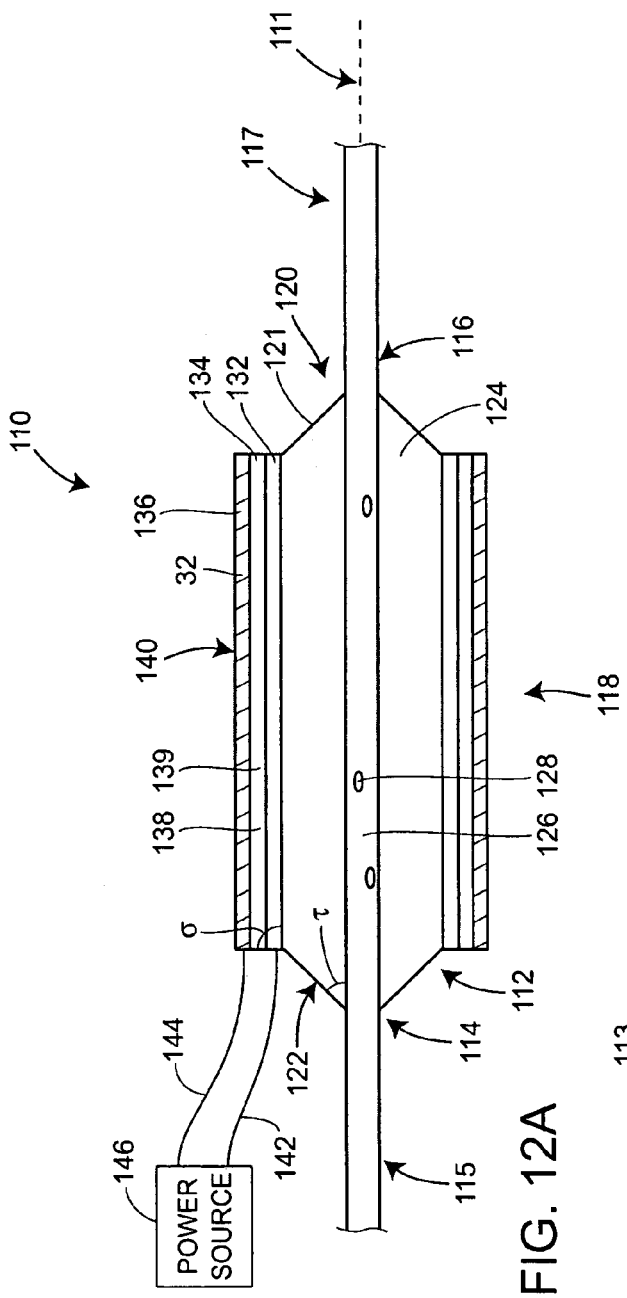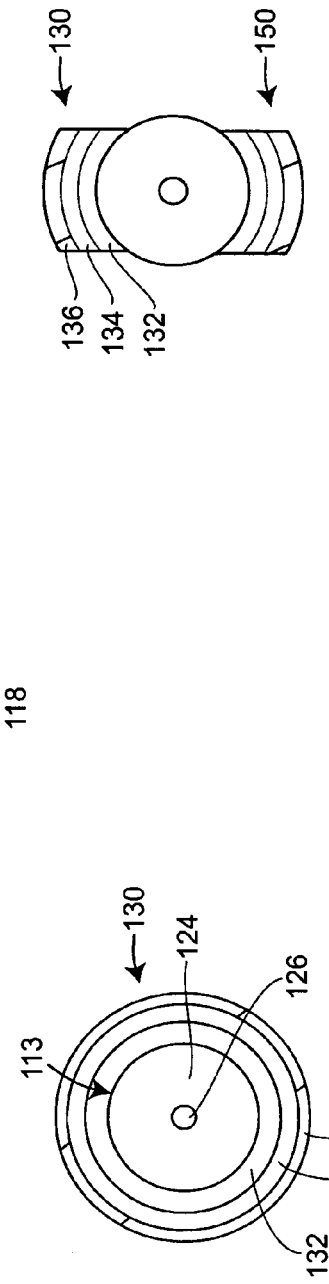

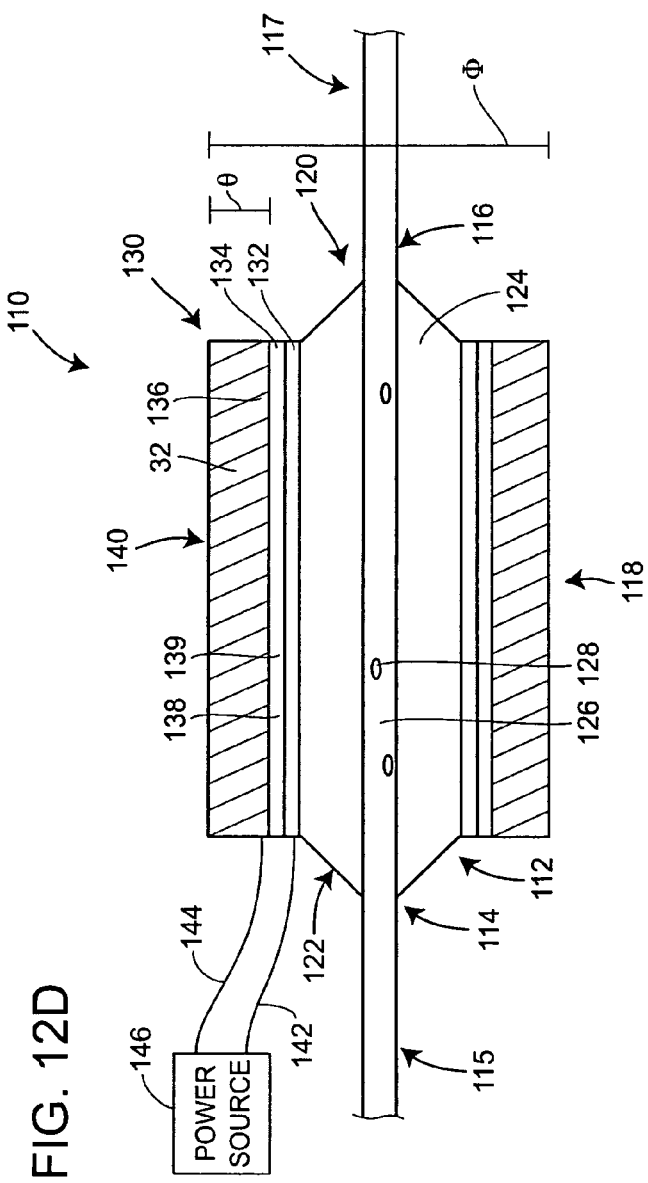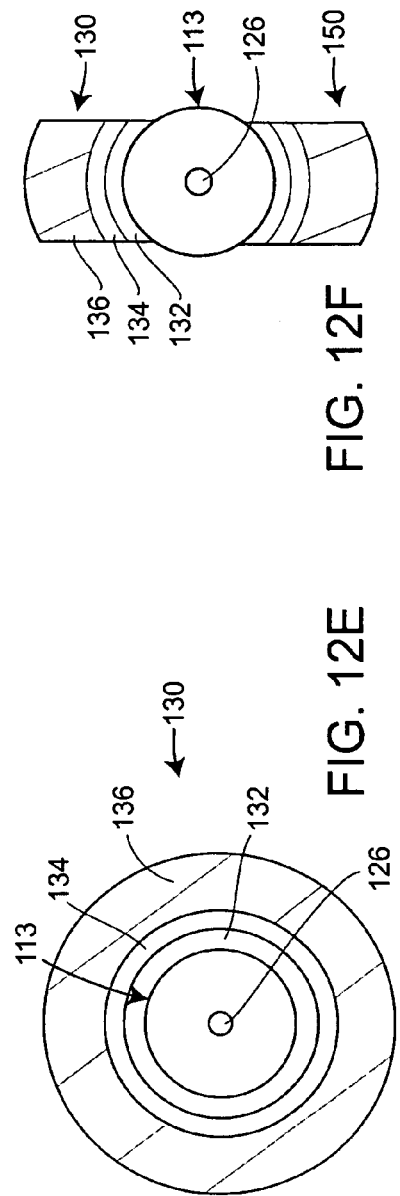

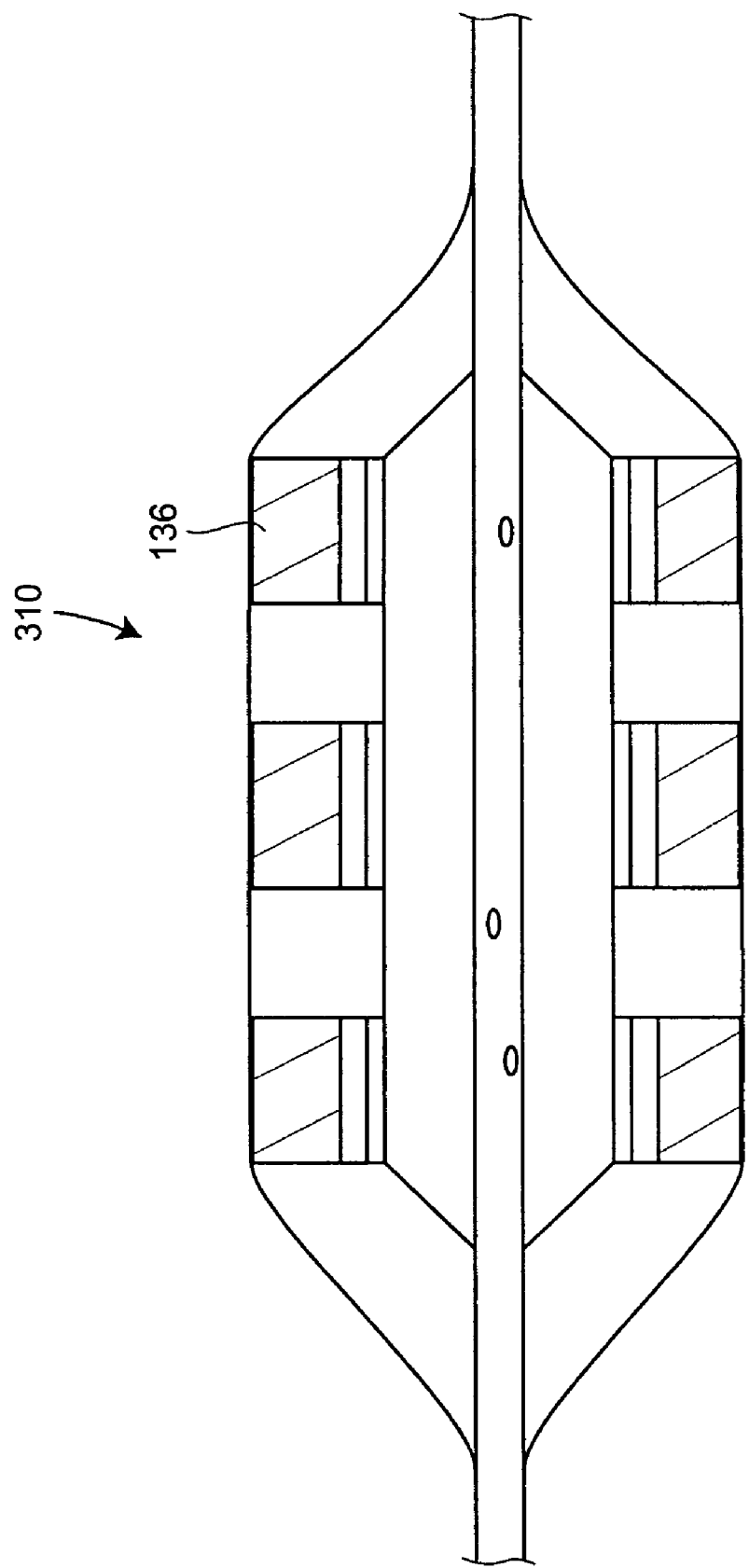

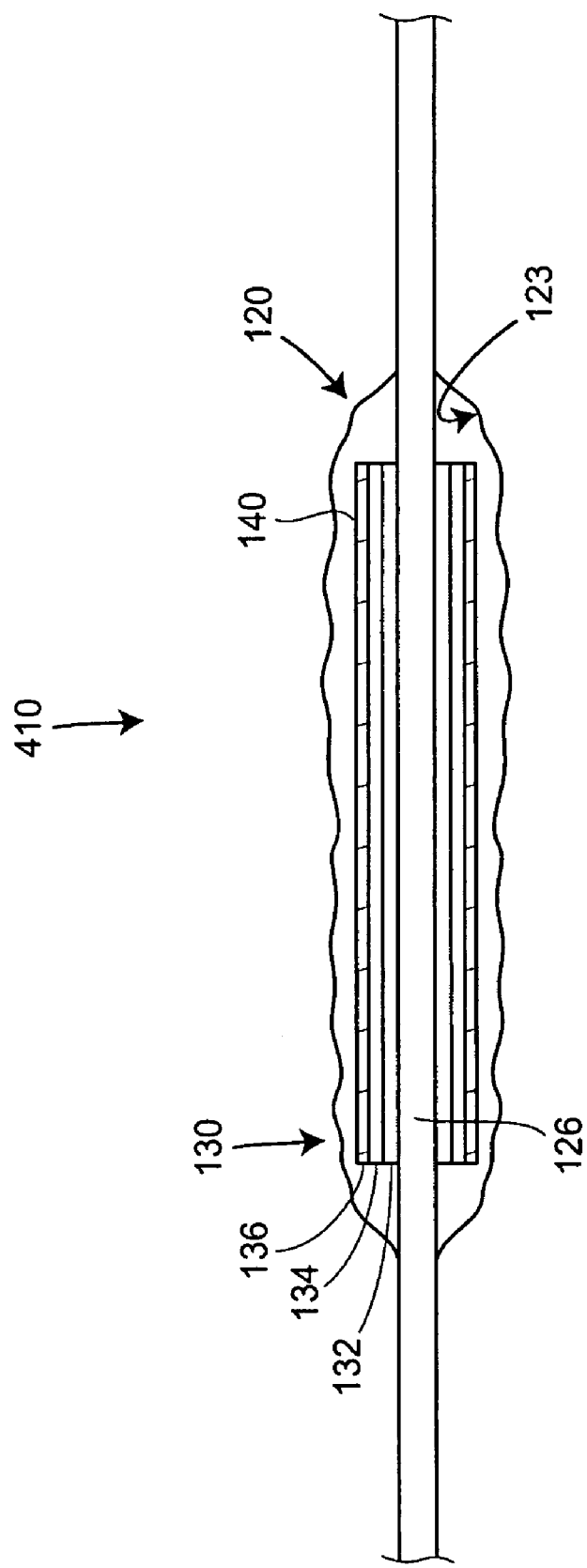

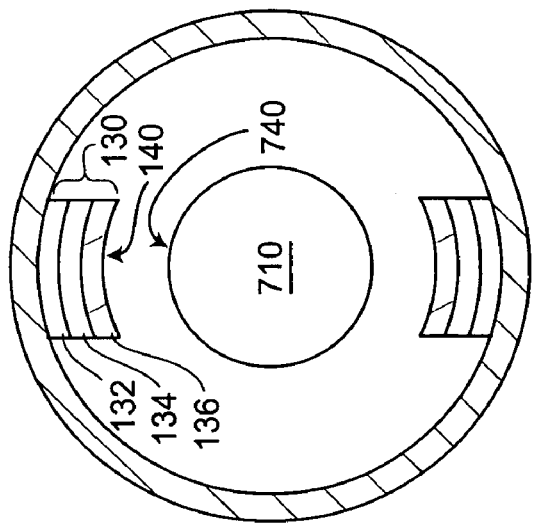
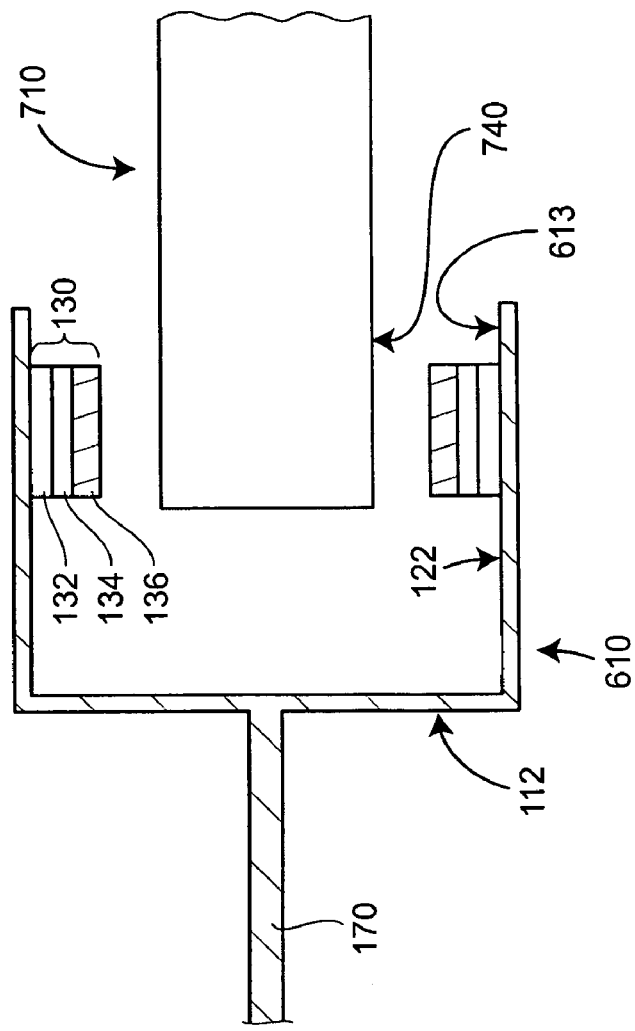

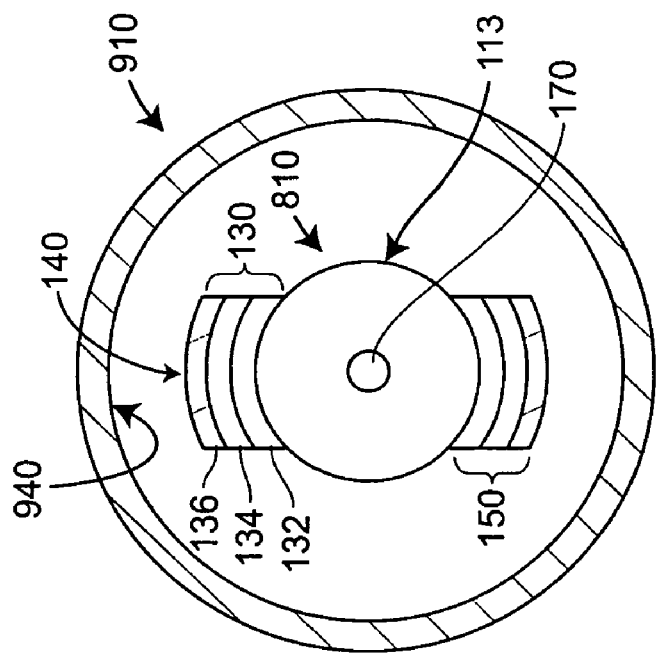
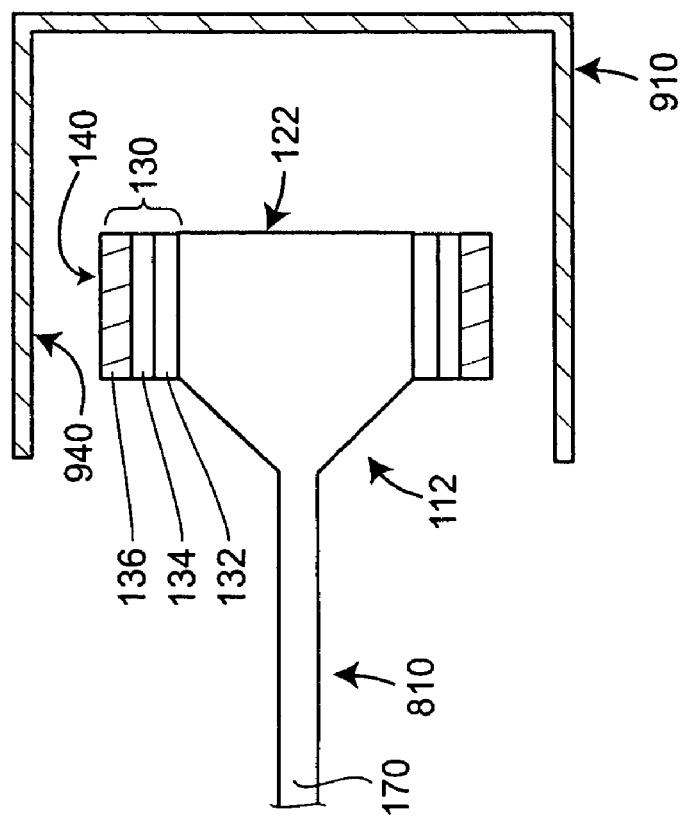
FIG. 19B
FIG. 19A

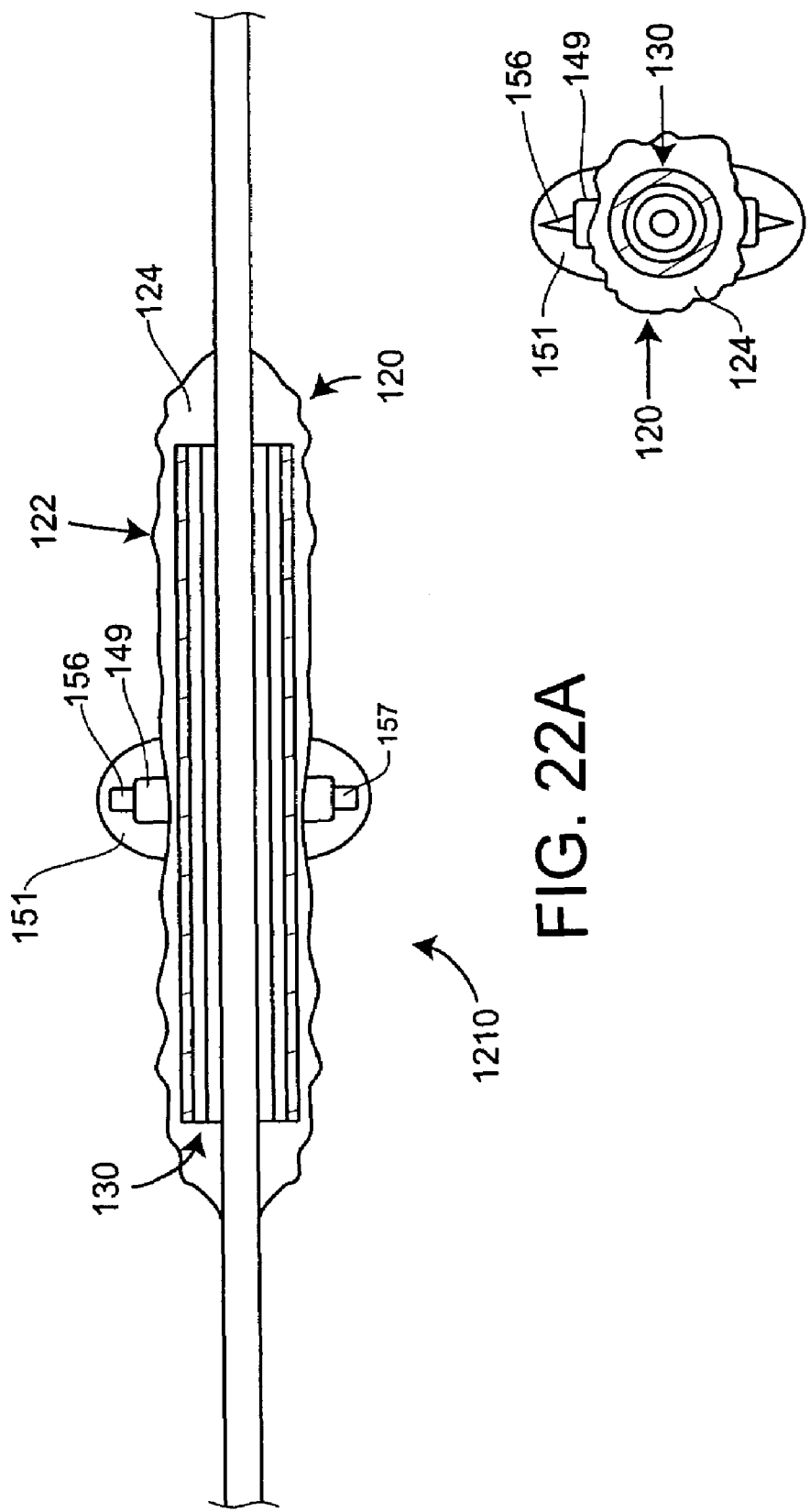
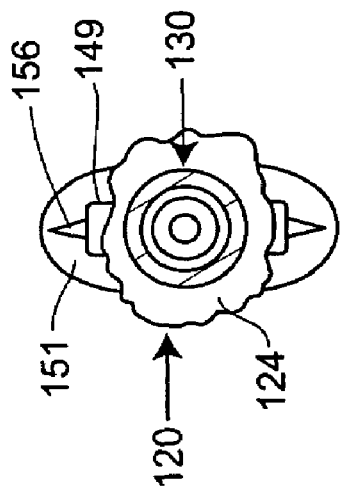

NANO-ACTUATED MEDICAL DEVICE

CROSS-REFERENCE TO RELATED APPLICATIONS

This application is a continuation-in-part of U.S. patent application Ser. No. 10/270,815 filed Oct. 15, 2002 now Pat. No. 7,037,319.

FIELD OF THE DISCLOSURE

The present disclosure generally relates to medical devices and, more particularly, relates to catheters, stents, and delivery devices.

BACKGROUND OF THE DISCLOSURE

Angioplasty procedures are well known within the medical community. During such a procedure, a catheter is navigated through a lumen of the human body to a site needing expansion. For example, a distal portion of a catheter containing a deflated balloon is directed to an area of an artery that is substantially blocked, and that can be enlarged upon expansion of the balloon.

Balloon catheters include pneumatically and hydraulically actuated catheters. Traditionally, catheters have employed hydraulic means of expansion. A balloon catheter may be manufactured from an elastomeric conduit with an enlarged diameter portion thereof forming a balloon. Upon the balloon reaching the procedure site, pressurized fluid is directed through the conduit and to the balloon so as to enlarge the diameter of the balloon, thereby imparting force against the interior walls of the lumen and thus expanding the blocked area. In order to minimize the entrance diameter of the puncture hole through the skin into the arterial system and thereby decrease the time for healing, as well as the amount of scar tissue after healing, it is desirable to be able to reduce the diameter of the balloon catheter system while non-pressurized.

Currently such angioplasty catheters are made using either compliant or non-compliant elastomeric material. Due to the necessity of being able to use high forces to open up blocked arteries, fluid pressures used to actuate the balloon can be very high (more than 20 atmosphere). With a compliant balloon material, this requires very thick elastomeric materials to be used. Thick compliant materials can withstand such high pressures, and adequately retract into their original dimension to allow for retraction through the lumen, however, their thickness is counter to the desire of having non-expanded small dimensions. Non-compliant balloon materials can be constructed having thinner balloon wall dimensions, but use of such materials generally entails balloon folding for size reduction when not expanded.

Moreover, both compliant as well as non-compliant balloon materials generally have to be hydraulically actuated, therefore one has to provide a fluid access lumen through the complete catheter system. The walls of such an access lumen have to be sufficiently strong to withstand the pressure, but this design demand is in contrast to the use of highly flexible, thin catheter systems that allow for optimization of push and track without bursting.

A further downside of hydraulic balloon actuation is the risk of balloon leakage. Leaks can originate during expansion in calcified lesions. As the creation of leaks will prevent further expansion, this can lead to very serious situations, for example, with a balloon expanded stent procedure, this can lead to a partially-deployed, and thus unstable, stent. As a result, the catheter often has a thick and bulky shaft-like construction. For most applications, small diameters and high flexibility are of great importance. For example, with neurological procedures, or procedures within the lower extremities having mostly torturous vessels, such fluid-driven elastomeric catheters and their relatively large diameters, are simply unusable. Further complicating matters is the fact that such balloon constructions can only be made to a certain minimum diameter, thus preventing usage in such lumens, as well as lumens which have been reduced to a small diameter due to a condition requiring the angioplasty. Especially challenging is the use of current balloon catheters when stenting a bifurcation. Bifurcation generally involves using two balloons in parallel, doubling the space requirements.

Medical device needs are not limited to balloon catheters. The rapid increase of use and importance of implantable medical devices, e.g., stents, in cardiology and other medical fields calls for new and improved methods and devices for delivery and retrieval of such implants. New and improved means of drug delivery allowing more precise and controlled release of pharmaceuticals are also sought.

With the miniaturization and increase in complexity and functionality of medical devices, there exists a need for improved micro-actuation technologies. Existing electro-active materials that are appropriate for use in medical device actuators include electro-active polymers (EAPs), electroactive ceramics (EACs) and shape memory alloys (SMAs). However, each of these technologies has significant limitations. While having the ability to induce strains that are as high as two orders of magnitude greater than the movements generally possible with the relatively rigid and fragile EACs, EAPs have relatively low actuator forces and mechanical energy density; some EAPs also show a lack of robustness. SMAs are fairly rigid, only have strains that reach 8%, and they do not have full reversal action.

Collectively, the current failings of balloon catheters and other medical devices, as well as the limitations of actuators appropriate for use in such devices, reveals the need for novel medical devices incorporating new actuator technologies.

SUMMARY OF THE DISCLOSURE

In accordance with one aspect of the disclosure, a radially expanding nanopaper actuation system catheter is disclosed, which may include an electrode, a membrane surrounding the electrode, a cylindrical ring of nanopaper (e.g., bucky paper, nanotube paper) surrounding the membrane, an electrolyte injected into the nanopaper, and an elastic sheath mounted about the electrode, nanopaper, and electrically conductive solution.

In accordance with another aspect of the disclosure, a method of radially expanding the distal section of an angioplasty catheter is disclosed, which may comprise navigating a distal end of the catheter to a procedure site, wherein the distal end includes a construction having a nanopaper ring acting as one electrode surrounding a membrane surrounding a second electrode, and energizing the electrode pair. The distal end of the catheter further includes an electrolyte-containing fluid within the nanopaper and membrane, and an elastic sheath surrounding the nanopaper. The energization of the electrode generates microbubbles in the nanopaper thereby causing the nanopaper to expand. This catheter system is also referred to in the following text as a "balloon" catheter.

In accordance with another aspect of the disclosure, a "balloon" catheter is disclosed which may comprise a conduit having a distal end and a proximal end, and means for expansion disposed in the distal end of the conduit, which means are electrically actuated.

In accordance with yet another aspect of the disclosure, a medical device is disclosed, which may comprise a substantially rigid tube having a closed end and an open end, nanopaper disposed in the substantially rigid tube at the closed end, electrically conductive solution dispersed in the nanopaper, a first electrode coupled to the nanopaper, the nanopaper constituting a second electrode, and electrically conductive solution, and the first electrode separated from the nanopaper by a membrane, and a deployable member disposed in the substantially rigid tube proximate the open end.

In accordance with another aspect of the disclosure, a medical device is provided, which may comprise a housing and a nanoactuator (e.g., a nanotube actuator) operatively associated with the housing. The actuator comprising a first electrode, a separator operatively associated with the first electrode and a second electrode, the second electrode comprising nanopaper, and an electrolyte operatively associated with the separator and first and second electrodes. In some embodiments of this aspect, the actuator or actuators are operatively associated with the housing so that a clamp is provided.

In accordance with another aspect of this disclosure, a method of using a medical device is provided. The method may comprise positioning the medical device in a body lumen, and activating a nanoactuator operatively associated with the medical device by applying voltage causing microbubbles to form and expand nanopaper within the nanoactuator.

In accordance with another aspect of this disclosure, a method of using a first medical device as a clamp to grip and deliver a second medical device, the method may comprise the following: Aligning the first and second medical devices relative to one another to prepare the second device to be gripped by the first medical device. Activating a nanoactuator operatively associated with a housing of the first medical device, and further having an actuator surface, so that the first medical device grips the second medical device with the actuator surface contacting a surface of the second medical device, and positioning the second medical device in a desired location within a body lumen. In some embodiments, once the second medical device is positioned and the clamp released, the first medical device may be redrawn from the body while leaving the second device implanted in the body lumen. In some embodiments, the first medical device is used to grip the second implanted medical device using the nanoactuator to remove the devices from the body lumen.

In accordance with another aspect of the disclosure, a medical device is provided that may comprise a housing with a proximal end and a distal end, a nanoactuator, a blade, and a covering. The nanoactuator may be operatively associated with the housing, the actuator comprising a first electrode, a separator operatively associated with the first electrode and a second electrode, the second electrode comprising nanopaper, and an electrolyte operatively associated with the separator and first and second electrodes. The blade may be operatively associated with the housing. The covering may be operatively associated with the blade, the covering is provided so as to envelope the blade when the nanoactuator is not activated, and allowing for at least a portion of the blade to emerge from the covering when the actuator is activated.

In accordance with another aspect of the disclosure, a method of employing a medical device is provided. The method may comprise positioning a blade in an area to be cut, activating the actuator so that at least a portion of the blade emerges from the covering, cutting with the blade, and may further comprise deactivating the actuator so that the blade is again enveloped by the covering.

In accordance with another aspect of the disclosure, a balloon catheter is provided. The balloon catheter may comprise a housing comprising a balloon with a proximal end and a distal end, a guide wire operatively associated with the housing, and a nanoactuator operatively associated with the housing. The actuator may comprise a first electrode, a separator operatively associated with the first electrode and a second electrode, the second electrode comprising nanopaper, and an electrolyte operatively associated with the separator and first and second electrodes. The actuator may be operatively associated with the distal end of the balloon or a portion of the guidewire adjacent to the distal end of the balloon.

In accordance with another aspect of the disclosure, a method for advancing a balloon catheter through a stenosis is provided, which may utilize the actuator described in the previous aspect. The method may comprise navigating all or part of the actuator into a stenosis, activating the actuator to cause expansion, the expansion thereof causing the stenosis to open at least partially, deactivating the actuator, and may further comprise advancing all or part of the balloon into the stenosis.

In accordance with another aspect of the disclosure, a medical device is provided. The medical device may provide a housing, a nanoactuator, a nanoactuator operatively associated with the housing, and a hook operatively associated with the housing and the nanoactuator. The actuator may comprise a first electrode, a separator operatively associated with the first electrode and a second electrode, the second electrode comprising nanopaper, and an electrolyte operatively associated with the separator and first and second electrodes. The hook may have a proximal end and a distal end, the distal end shifted toward the housing when in a retracted position and away from the housing when in a protracted position.

In accordance with another aspect of the disclosure, a method of attaching a medical device to a lining of a body lumen is provided. The method may comprise positioning the medical device at a desired position for attachment, and activating a nanoactuator operatively associated with a housing of the medical device and a hook of the medical device.

In accordance with another aspect of the disclosure, a method of using a first medical device to position a second medical device is provided. The method may comprise aligning a hook of the first medical device with a receptacle of the second medical device, activating a nanoactuator operatively associated with the hook of the first medical device, engaging the hook with the receptacle, and positioning the second medical device at a desired location within a body lumen.

In accordance with another aspect of the disclosure, a medical device comprising a nanoactuator, and designed to procure tissue samples for a biopsy is provided.

In accordance with another aspect of the disclosure, a method of procuring a tissue sample for a biopsy using a medical device comprising a nanoactuator is provided. The method may comprise positioning the medical device at a location where a tissue sample is to be extracted; and activating the nanoactuator to bring a first and second surface of the medical device together with the tissue sample situated between the first and second surfaces.

These and other aspects and features of the disclosure will become more apparent upon reading the following detailed description when taken into consideration with the accompanying drawings.

BRIEF DESCRIPTION OF THE DRAWINGS

FIG. 1 is a schematic representation of a system constructed in accordance with the teachings of the disclosure;

FIG. 2A is a sectional view of the balloon assembly of FIG. 1 taken along the line of 2-2 of FIG. 1;

FIG. 2B is a sectional view similar to that shown in FIG. 2A, except showing the balloon in a folded configuration;

FIG. 3 is a sectional view of the balloon assembly of FIG. 2, but depicted in an expanded or actuated state;

FIG. 12A is a partial longitudinal sectional view of a medical device with a nanoactuator, in a non-activated state, mounted on an exterior surface, according to the teachings of the disclosure;

FIG. 12B is a sectional view of the medical device shown in FIG. 12A showing an embodiment wherein the nanoactuator encircles the medical device, according to the teachings of the disclosure;

FIG. 12C is a sectional view of the medical device shown in FIG. 12A showing an embodiment wherein there are two nanoactuators positioned on opposing sides of the medical device, according to the teachings of the disclosure;

FIG. 12D shows the medical device of FIG. 12A, but in an activated state.

FIG. 12E is a sectional view of the medical device shown in FIG. 12D showing an embodiment wherein the nanoactuator encircles the medical device, according to the teachings of the disclosure;

FIG. 12F is a section view of the medical device shown in FIG. 12D showing an embodiment wherein there are two nanoactuators positioned on opposing sides of the medical device, according to the teachings of the disclosure;

FIG. 14B is an alternative embodiment of the medical device shown in FIG. 12D, according to the teachings of the disclosure;

FIG. 15A is a partial longitudinal sectional view of a medical device with a nanoactuator, in a non-activated state, mounted in an interior of the medical device, according to the teachings of the disclosure;

FIG. 18A is a longitudinal sectional view of a first medical device with an inward-facing clamp positioned relative to a second medical device, the clamp comprising a nanoactuator in a non-activated state, according to the teachings of the disclosure;

FIG. 18B is a sectional view of one embodiment of the first and second medical devices shown in FIG. 18A, according to the teachings of the disclosure;

FIG. 19A is a longitudinal sectional view of a first medical device with an outward-facing clamp positioned relative to a second medical device, the clamp comprising a nanoactuator in a non-activated state, according to the teachings of the disclosure;

FIG. 19B is a sectional view of one embodiment of the first and second medical devices shown in FIG. 19A, according to the teachings of the disclosure;

FIG. 22A is a partial longitudinal sectional view of a medical device comprising a nanoactuator and a blade, the nanoactuator in a non-activated state and within an interior of the medical device, and the blade enveloped by a covering, according to the teachings of the disclosure;

FIG. 22B is a sectional view of the medical device shown in FIG. 22A showing an embodiment wherein the nanoactuator encircles the medical device, according to the teachings of the disclosure;

Figure 4:
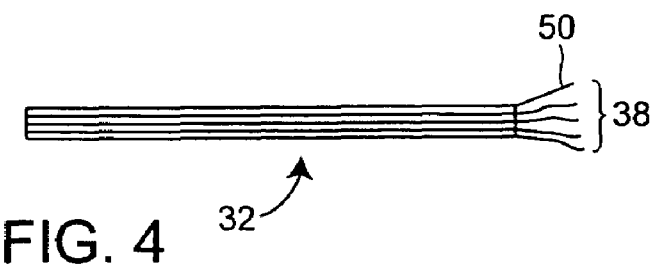
FIG. 4 is a longitudinal sectional view through the nanopaper of FIG. 1 taken along the line 4-4 of FIG. 1.

While the disclosure is susceptible to various modifications and alternative constructions, certain illustrative embodiments thereof have been shown in the drawings and will be described herein in detail. It should be understood, however, that there is no intention to limit the disclosure to the specific forms disclosed, but on the contrary, the intention is to cover all modifications, alternative constructions, and the equivalents falling within the spirit and scope of the disclosure as defined by the appended claims.

DETAILED DESCRIPTION

Referring now to the drawings, and with specific reference to FIG. 1, a medical device or system constructed in accordance with the teachings of the disclosure is generally referred to by reference numeral 20. While the following disclosure will be made with primary reference to a catheter, specifically an angioplasty catheter, it is to be understood that the teachings of the disclosure can be used in conjunction with many other types of medical devices wherein the expansion of the device through the use of electrical energization, such as, but not limited to, deploying stents, taking a biopsy, releasing medication or other pharmaceuticals, movement of a guide wire or the like, are certainly encompassed by the present disclosure.

The system 20, as depicted in FIG. 1, may include a catheter 22 having a distal end 24 and a proximal end 26. The proximal end 26 may be the end most directly manipulated by a physician or the like and the distal end 24 would be the end navigated through a lumen or other passageway of the human body for the performance of various medical procedures. At the distal end 24, a balloon assembly 28 may be provided. As shown in FIG. 1, as well as the sectional views of FIGS. 2A, 2B and 3, the balloon assembly 28 may include a central core or electrode 30 about which is provided a porous membrane (separator) 48, which itself is surrounded by nanopaper 32 (e.g., nanotube paper, bucky paper), which serves as a second electrode, and which may be provided in the shape of a tube. A function of the electrically isolating, porous membrane 48 is to allow protons and electrons to pass through the fluid entrained in its porous structure, thereby closing the electric circuit between the two electrodes 30, 32. In some embodiments, the porous membrane 32 comprises a protein exchange membrane. Around the nanopaper 32, a polymeric membrane (outer sheath) 34 may be provided. The outer sheath 34 may be elastomeric. FIG. 2B shows the balloon assembly 28 in a folded configuration that the balloon assembly may assume prior to activation of the actuator.

Figure 5:
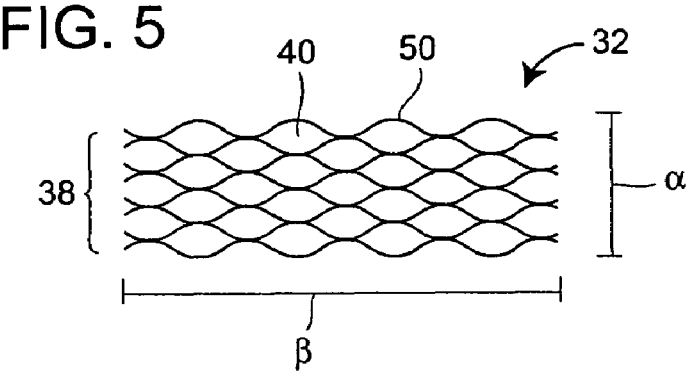
FIG. 5 is a longitudinal sectional view similar to FIG. 4, but depicted in an expanded state.

Referring now to FIGS. 4 and 5, the nanopaper 32 is shown in detail to include a plurality of layers 38 between which are provided a plurality of voids 40. Each of the layers 38 may be substantially corrugated in shape and positioned so as to form the voids 40 depicted in FIG. 5, or can be alternatively formed as by angular shapes or the like in the voids 40. Voids may also form between nanotubes and other nanostructures. Within the voids 40, an electrically conductive solution, which may comprise fluid 41 and the electrolyte 31, is placed, as by injection or the like, the importance of which will be described in further detail herein. In some embodiments, the fluid 41 itself may be electrically-conductive. In some embodiments, the fluid 41 may be non-electrically-conductive. The fluid 41 may be, but is not limited to being, aqueous, organic or a mixtures thereof. The embodiments shown in FIGS. 4 and 5 are for illustrative purposes only, as the nanopaper can take on any number of different structures and designs.

Referring again to FIG. 1, it will be noted that the system 20 further includes first and second conductors or wires 42 and 44 which extend from a power source 46 through the catheter 22 to the balloon assembly 28. More specifically, at the balloon assembly 28, the wire 42 is connected to the electrode 30, whereas the wire 44 is connected to the connector ring 36. The connector ring 36 is further connected to the nanopaper 32 and thereby to the electrolyte 31. A porous membrane 48 may be provided about the electrode as depicted in FIGS. 2 and 3. In some embodiments the porous membrane 48 comprises a proton exchange membrane.

With respect to materials, a variety of combinations can be employed, with an exemplary embodiment including an electrode 30 manufactured from gold or platinum. While other electrical conductors can certainly be employed, the use of gold or platinum further provides the feature of radiopacity to thus facilitate visibility of the device during fluoroscopy or the like. With regard to the outer sheath 34, it can be manufactured from any polymeric material. In some embodiments, the sheath 34 comprises a elastomeric material. Outer sheath 34 may comprise, but is not limited to, latex, rubber, silicon rubber, Pebax®, urethane, pelothane, Tecothane®, polyester isobutyl styrene, epoxies and thermoplastics. The electrolyte 31 can also be provided in a variety of forms, although the inventors have found the use of sodium chloride or hydrogen chloride to be particularly effective. Other chloride and halide salts may also be used. The use of sodium chloride is beneficial in that sodium chloride is naturally present within human blood, thus making any potential leaks less problematic.

The nanopaper may comprise any number of different kinds of nano- and micro-particles, materials, and structures, and is not limited to single wall carbon nanotubes (SWNT). These materials are also not limited to carbon compounds, nor is size a limitation. In some embodiments, the nanopaper comprises single wall nanotubes, the nanotubes having inner diameters of 0.34 nanometers to 4 nanometers, and lengths up to 100 micrometers. In some embodiments, the nanopaper comprises multi-wall nanotubes with inner diameters of 3 nanometers to 10 nanometers, outer diameters of 5 nanometers to 50 nanometers, and lengths up to 100 micrometers.

Other nanotubes that may be used in the nanopaper include, without limitation, those described in Wang, N., et al., *Monosized and Single-walled 4 Å Carbon Nanotubes,* Chem. Phys. Lett. 339:47-52 (2001), which is incorporated herein in its entirety. In some embodiments, microtubes or fibers comprise carbon with diameters from 0.05 micrometers to 100 micrometers, and lengths up to centimeters. Microtubes can as well be made of almost all metals or ceramics, dimensions of fibers may range from 2-4 nanometers and upwards. An example of a ceramic fiber is Alumina. Metals may also be employed, including but not limited to aluminum, gold and platinum.

The nanopaper 32 may comprise other nano- or microparticles or structures (fibers, balls, sheets, general shapes) within the paper, besides or in addition to nanotubes and/or microtubes. Examples of materials that can be mixed through the paper include, but are not limited to, multi-wall carbon nano fibers, bucky balls, NanoCeram® alumina fibers, which may be on the order of 2 nanometers in diameter, made by Argodine (Pittsburgh, Pa.). The nanopaper may comprise polymer fibers, such as polyester, polyamide, polyurethane, and high density polyether. In some embodiments, the constituents of the nanopaper 32 may provide functional groups for cross linkage and other purposes. Examples of such linkages are discussed in Bahr, J. L. et al., *Functionalization of Carbon Nanotubes by Electrochemical Reduction of Aryl Diazonium Salts: A Bucky Paper Electrode,* J. Am. Chem. Soc. 123:6536-6542 (2001).

The nanopaper 32 may comprise non-conductive as well as conductive components. The nanopaper 32 may possess a conductivity to allow for bubbles 52 to form within the paper. In some embodiments, such bubbles 52 form uniformly. The nanopaper 32 may also be designed to entrap bubbles 52. The conductivity of the nanopaper 32 may be measured by the macroscopic electrical conductivity of the nanopaper. The conductivity of nanopaper 32 comprising nanotubes may be about $0.9 \times 10^4$ to $1 \times 10^6$ Siemens/meter (S/m). Decreasing the conductivity may decrease the efficiency of the bubble formation. However, decreases in conductivity may be compensated for by increasing the voltage. Nanopaper 32 may have conductivities higher than about $1 \times 10^3$ S/m. The conductivity may depend on parameters including, but not limited to, dispersion and compression of the tubes, and average length of the tubes.

Any form of commercially available carbon nanopaper may be employed for the nanopaper 32 including, but not limited to, bucky paper or nanotube paper. Carbon nanopaper could be provided, for example, in the form of that disclosed in an article entitled *Actuator Response from Carbon Nanotube Sheets,* authored by G. M. Spinks, et al., the disclosure of which is expressly incorporated herein by reference. Another reference to produce this so-called "bucky" paper is described in *Large scale purification of single-wall carbon nanotubes: process, product and characterization,* authored by A. G. Rinzler, J. Liu, et al., Applied Physics A A67, 29-37 (1998), the disclosure of which is expressly incorporated herein by reference. Other applicable references include *Organic Solvent Dispersions of Single-Walled Carbon Nanotubes: Towards Solutions of Pristine Nanotubes,* authored by K. D. Ausman, et al., J. Physical Chem. 104(38):8911-8915 (2000), and *Single-Wall Carbon Nanotube Films,* T. V. Sreekumar, et al., Chem. Mater. 15:175-178 (2003), both of which are also expressly incorporated herein by reference. In some embodiments, the nanopaper comprises carbon nanotubes. In some embodiments, the nanopaper comprises at least 10% nanotubes by weight.

Specifically, as depicted in FIGS. 4 and 5, the nanopaper may include single walled carbon nanotubes suspensions that are vacuum-filtered to produce freestanding highly entangled nanotube ropes 50. Such single-walled (carbon) nanotubes (SWNTs) are commercially available as an aqueous suspension from, for example, Rice University of Houston, Tex. The nanotubes may be suspended in solvents comprising such constituents as surfactants (e.g., Triton X-100, i.e., alkylaryl polyether alcohol; octyl phenol ethoxylate) and organic solvents such as toluene. Nanotube mats are typically made by vacuum filtration through a poly (tetrafluoro ethylene) filter (e.g., Millipore LS, 47 mm in diameter, or Whatman Anodisc 47 Filter 20 nm pore size) of approximately 4 grams of a 0.6 milligram-per-milliliter nanotube suspension further diluted by the addition of approximately 80 milliliters of deionized water. The nanotube mat is then washed by 2×100 milliliters deionized water and 1×100 methanol followed by drying and vacuum at 70° Celsius for twelve hours. The shape of the nanotube mat (paper) may be controlled by the shape or arrangement of the filter as well as the use of centrifugal force. The typical nanotube mat produced is between 15 to 35 microns thick and has a bulk density of 0.3 to 0.4 grams per cubic centimeter and a four point conductivity of 5,000 S/cm. The nanotubes may spontaneously aggregate into bundles or ropes of approximately 10 nanometers in diameter and many microns in length. The nanotube mats are then peeled from the filter to produce freestanding films for use.

In some embodiments, nanotube mats (paper) are formed directly on the device or connected after assembly. One method is to directly deposit the nanopaper layer on top of the medical device. A medical device is positioned on top of the filter and the nanopaper layer is produced by embedding at least part of the device with the nanopaper layer at the same time. In some embodiments, a tubular filter is used in which one first produces a first nanopaper layer (using centrifugal force) after which one positions a tubular medical device (stent for example) within this ensemble with a close contact between the device and the first nanopaper layer. One then repeats the process of making a nanopaper layer. The second layer will embed the device in between the first and the second layer. In case of a stent, the struts are surrounded in whole or part by the nanopaper material.

In some embodiments, a second material is embedded inside the nanopaper, which may provide a connection with the device. One may position any number of polymer or metal fibers on the filter (or a woven structure). Secondly, one produces the nanopaper (which then embeds the fibers within the structure) while one leaves the ends of the fibers free of the paper. Once the nanopaper is made, it is taken off the filter material and the fibers may be used to provide a connection with the device. One could, for example, use polyethylene (PE) fibers and melt the ends together while wrapping the nanopaper around the device. This technique also provides for a stronger nanopaper material. Fiber materials could be made out of polymers such as PE, aramids, e.g., Nomex™, Kevlar™, or ceramic (Nextel™ fibers 3M) stainless steel (Bekaert).

In some embodiments, SWNT, suspended in an appropriate solvent, e.g., Toluene or Chloroform, is sprayed directly on the medical device and then allowed to evaporate at preferably elevated temperatures. (SWNT in such solvents is available from Zyvex, Richardson, Tex.) To provide for a high density packing of the SWNT, an additional step is taken by shrinking a shrink tube over the device or by using an elastic tube over the device. Next, one uses a high external pressure to compress the paper and subsequently removes the shrink tube. In some embodiments of the medical devices (and methods) of this disclosure, surfaces or other elements in contact with the body comprise biocompatible material.

In operation, the system 20 can be employed for medical procedures such as, but not limited to, angioplasty wherein the catheter 22 is navigated through a lumen (not shown) until the distal end 24 is appropriately positioned, such as within a blocked area of an artery. Once so positioned, the power source 46 can be actuated so as to direct a voltage, such as 1.2 Volts, or at least higher than 1 Volt, through the conductors 42 and 44. The resulting current flow may result in microbubbles 52 being formed within the fluid 41 contained with the voids 40, between nanotubes, and on surface within the nanopaper 32. Such bubbles 52 may also be formed on surfaces of nanotubes and other nanostructures of the nanopaper 32. Gas (e.g., $Cl_2$ and/or $O_2$) formation at the electrode surface starts due to the following two reactions:

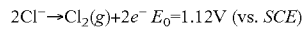

$2Cl^- \rightarrow Cl_2(g) + 2e^-$  $E_0 = 1.12V$ (vs. SCE)

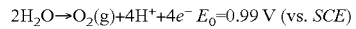

$2H_2O \rightarrow O_2(g) + 4H^+ + 4e^-$  $E_0 = 0.99$ V (vs. SCE)

As a result of gas being trapped within the pores of the carbon nanotube mat, the thickness of the carbon nanotube mat increases. As shown best in FIGS. 3 and 5, such creation of microbubbles causes the ropes 50 forming the nanopaper 32 to move apart, which in turn causes the volume of the nanopaper 32, which may include the electrolyte 31, to greatly expand. Using a nanopaper 32, such as that disclosed above, such actuation can cause nanopaper 32 to increase in thickness α by up to 300% (although lesser and greater percentages are also possible), with the length β of the nanopaper 32 remaining substantially the same. The expansion of the nanopaper 32 in turn causes the outer sheath 34 to radially expand as well, which in turn imparts force against the interior surface of the lumen, clearing the blockage. As the micro gas bubbles are trapped within the nanopaper, there is no essential need for an enclosed system. One could therefore use sodium chloride as the electrolyte given its pre-existing presence in the blood.

Once the balloon assembly 28 is expanded to open up the blockage, which may or may not include full expansion, the power source 46 can be deenergized. The microbubbles 52 will therefore no longer be generated, and the existing microbubbles 52 will reoxidize electrochemically, thereby reversing the expansion supported by the radially inward acting force from the outer sheath 34. While reoxidation may occur spontaneously or slowly over time, one generally reverses the potential of the actuator to enable fast reoxidation and removal of the microbubbles. Removal of the microbubbles 52 enables the (optional) outer sheath 34, which is elastic, to reconstrict, and thereby recompress the nanopaper 32 to a reduced diameter, which may be its original diameter before activation. Once back to a reduced diameter, the balloon assembly 28 and catheter 22 can be withdrawn from the lumen, or reactivated. While the activation step of microbubble formation and expansion of the voids 40 in the nanopaper (mat) may take on the order of tens of seconds to fill, collapse may occur in approximately one second. The sheath 34 is not necessary for reduction of diameter, but may be used to accelerate collapse. Other means of accelerating collapse include without limitation polymers provided as part of the nanopaper to accelerate collapse. Such polymers may be elastic. Nanoactuators of medical device 20, and such actuators 130 described herein, may have any number of different lifespans, with some embodiments having up to 100,000 cycles of activation and deactivation. In some embodiments, the expansion of the balloon may be made permanent by such means including, but not limited to, settable gels and mechanical means, e.g., over-center locks (e.g., for use with the hook 163 described herein), and "Chinese-finger cuff-like" locks.

Figure 6:
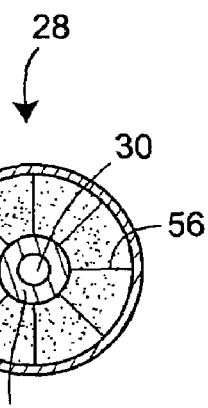
FIG. 6 is a sectional view of an alternative embodiment of a balloon assembly constructed in accordance with the teachings of the disclosure.

Referring now to FIG. 6, an alternative embodiment of the balloon assembly 28 is shown in cross-section. As shown therein, the balloon assembly is substantially the same as that depicted in the first embodiment. Wherein like elements are employed, like reference numerals are used. However, such an embodiment further includes a plurality of radial slits 56 through the nanopaper 32. As indicated above, during expansion, in some embodiments, the nanopaper 32 can expand in circumference by up to 300%. The resulting tangential stress on the paper can lead to radial cracks detrimentally affecting the performance of the balloon assembly 28. Accordingly, the radial cuts 56 may be made along the longitudinal axis of the nanopaper 32 prior to mounting the outer sheath 34.

Figure 7:
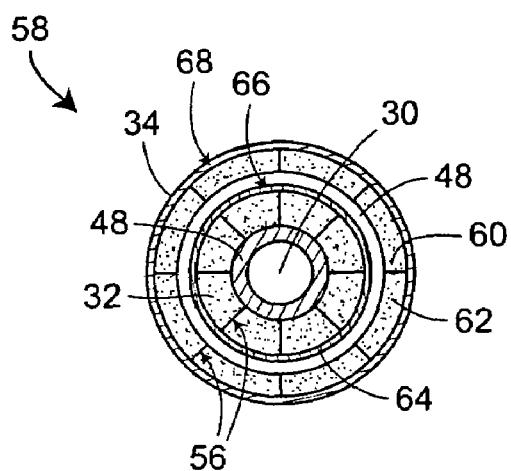
FIG. 7 is a sectional view through a second alternative embodiment of a balloon assembly constructed in accordance with the teachings of the disclosure.

As indicated above, in one exemplary embodiment, the nanopaper 32 employed has a thickness of between 15 and 35 micrometers. However, the scope of the disclosure certainly includes other dimensions, with such thicknesses being advantageous depending upon the size of the lumen through which the catheter 22 is to be navigated. One way to change the resulting diameter would be to use a multi-layered construction as depicted in FIG. 7. As shown therein, the balloon assembly 58 includes a second ring 60 of nanopaper 62. In addition, to serve as an electrical connection, a metallic coating 64 could be provided around an outer surface 66 of the first ring of nanopaper 32 with the outer sheath 34 being provided around an outer surface 68 of the second ring 60. In addition, it should be noted that in the depicted embodiment, a plurality of slits 56 is provided through each of the first and second rings 32, 60. It is to be understood that such a multi-ringed embodiment could be produced without slits as well.

In addition, while not depicted, it will be understood that separate electric connections can be provided to both the electrode 30 and metallic coating 64 to separately and selectively actuate each of the rings 32 and 60. Accordingly, depending upon the ring being actuated, the thickness or diameter of the resulting balloon assembly 58 can be tailored to the specific lumen diameter.

Figure 8:
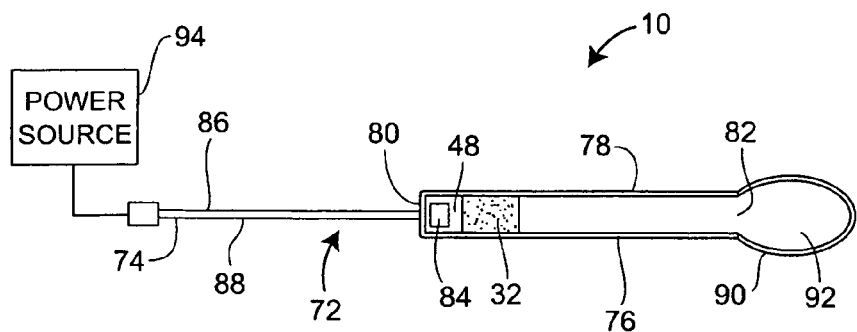
FIG. 8 is a schematic representation of an alternative system constructed in accordance with the teachings of the disclosure and employing a substantially rigid tube.
Figure 9:
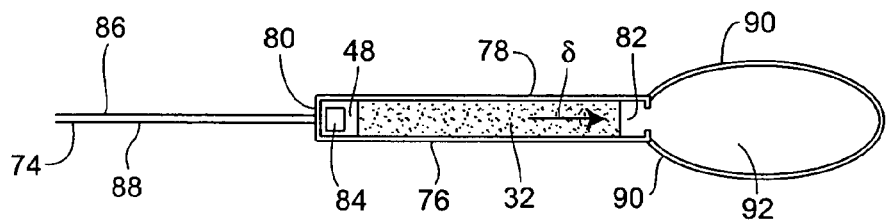
FIG. 9 is a schematic representation similar to that of FIG. 8 but depicting the system in a deployed state.

In a still further embodiment, depicted in FIGS. 8 and 9, the nanopaper 32 can be used to expand in a longitudinal direction, as opposed to the radial expansion depicted in the first three embodiments. More specifically, a medical device 70 is depicted in FIGS. 8 and 9 and can be placed at, for example, a distal end 72 of a guide wire 74 or the like. The medical device 70 may include a substantially rigid tube 76 manufactured of a suitable polymer, metal, or ceramic and may include a cylindrical sidewall 78, a closed end 80, and an open end 82. An electrode 84 may be provided proximate the closed end 80 and be electrically connected to conductors 86, 88. The nanopaper 32 is placed within the substantially rigid tube 76 proximate the electrode 84. A deployable member 90 may then be placed next to the nanopaper 32 proximate the open end of the substantially rigid tube 76. In the depicted embodiment, the deployable member 90 is provided in the form of a balloon 92 filled with an electrically conductive solution that may comprise an electrolyte such as sodium chloride. In those embodiments depicted in FIGS. 8-11, the nanopaper 32 may be layered so that when activated expansion occurs towards the open end 82.

In a still further embodiment, multiple sections along the axial direction can be included in the "balloon" design, sharing the central electrode, but with each nanopaper ring being individually actuable. Such a system allows sections to be expanded in timed sequences. This for example, can be advantageous in expanding stents where either the central sections or end sections have to be expanded first. It is even possible to alternate the activation of multiple sections in order to establish a very controlled uniform radial expansion of the stent along the axial direction. In some embodiments, a stent may be deployed at an ostium, placing and deploying the proximal end of the stent near the ostium, so any foreshortening or length expansion will be taken at the distal end once that section of the actuator is being expanded. In some embodiments, the deployment of several short stents placed adjacent to each other on a single delivery device comprising multiple axially positioned actuators, each serving one individual stent section, which allows stenting along a relatively long section of a the vessel while minimizing the issue of length change associated with single long stents.

As shown in a comparison between FIGS. 8 and 9, actuation of a power source 94 energizes the electrode 84 that is separated from the nanopaper 32 by a membrane 48, which in turn causes the nanopaper 32 to expand based on the principles identified above. However, since the substantially rigid tube 76 constricts radial expansion in the depicted embodiments, the nanopaper 32 expands longitudinally as indicated by the arrow δ. Expansion of the nanopaper 32 accordingly then causes the balloon 92 to exit through the open end 82, which, upon clearing the cylindrical sidewall 78, expands in a radial direction. Such expansion capability can be used in angioplasty procedures or the like. Since the nanopaper 32 and balloon 92 are operatively associated with one another, not only will the balloon 92 not exit the substantially rigid tube 76, but upon deactuation of the power source 94, the nanopaper 32 will retract, thereby drawing the balloon 92 back into the substantially rigid tube 76. In some embodiments, a device a knife or needle may be attached to the front of the balloon, allowing for cuts or punctures to be made in chronic total occlusions.

Figure 10:
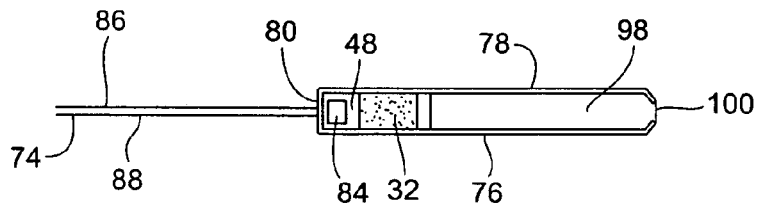
FIG. 10 is a schematic representation of a second system constructed in accordance with the teachings and of the disclosure and used for deploying medical devices or medication.
Figure 11:
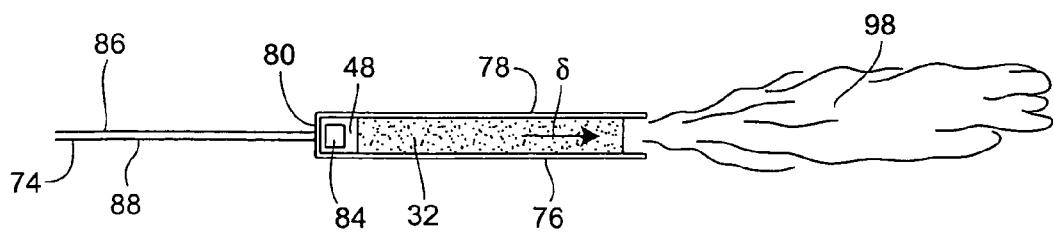
FIG. 11 is a schematic representation similar to that of FIG. 10, but depicted in a deployed state.
Figure 13A:
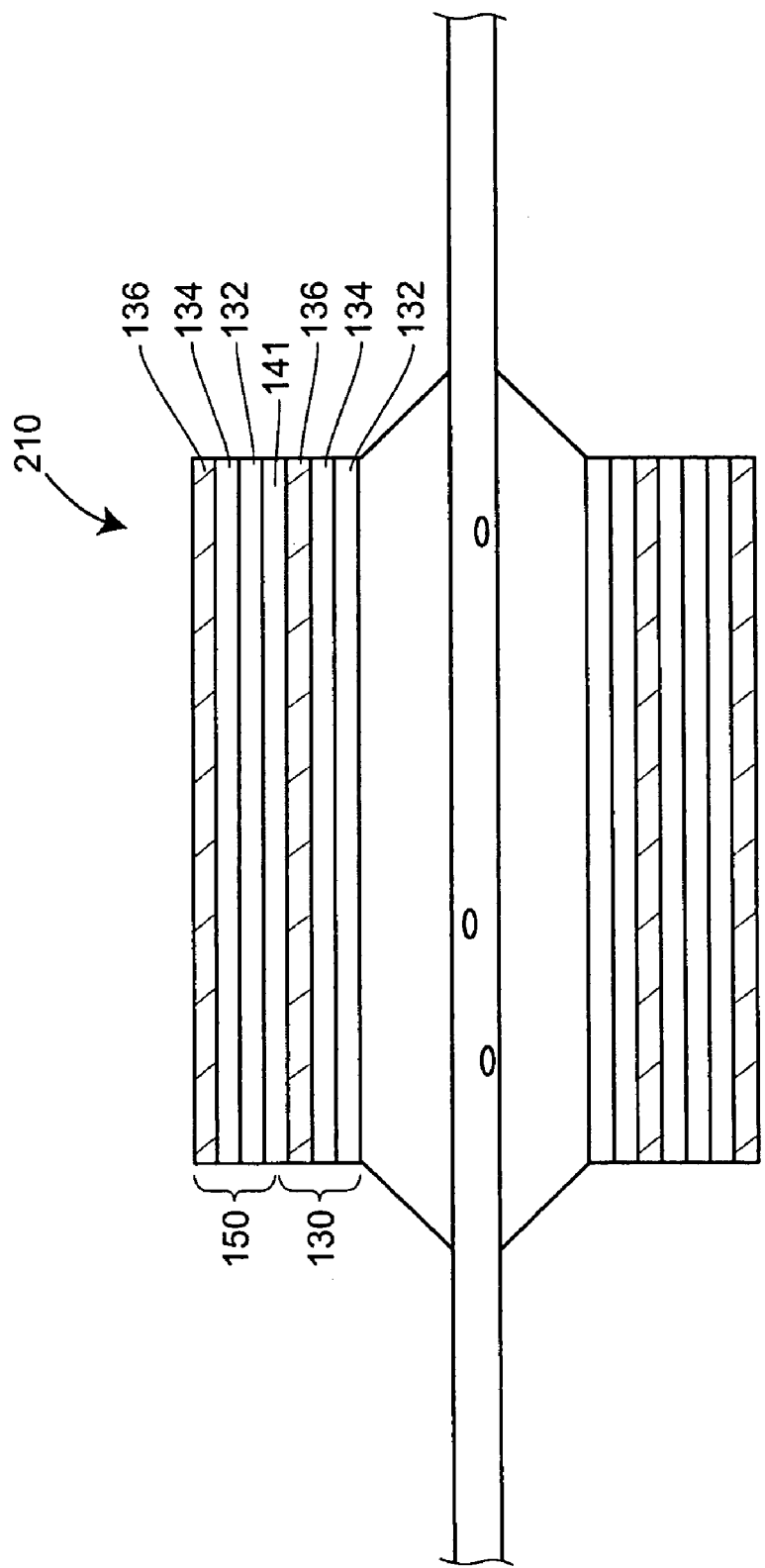
FIG. 13A is a partial longitudinal sectional view of a medical device with a "multi-layer" nanoactuator (i.e., "stacked" nanoactuators), in a non-actuated state, mounted on an exterior surface, according to the teachings of the disclosure.
Figure 13C:
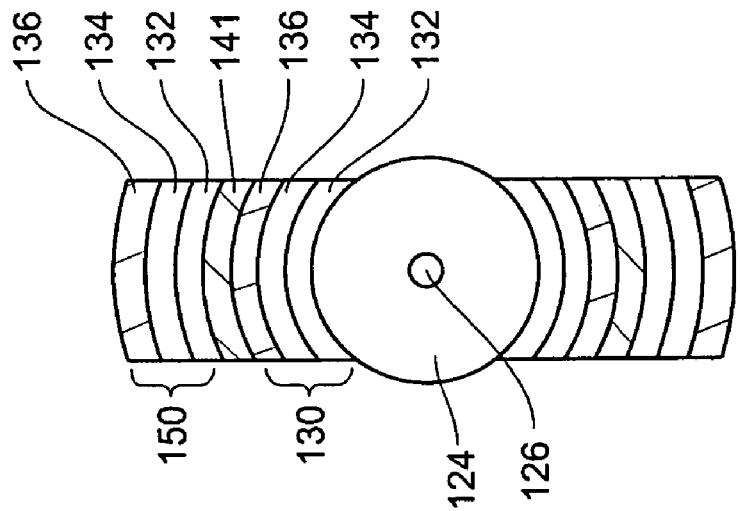
FIG. 13C is a section view of the medical device shown in FIG. 13A showing an embodiment wherein there are two nanoactuators positioned on opposing sides of the medical device, according to the teachings of the disclosure.
Figure 13B:
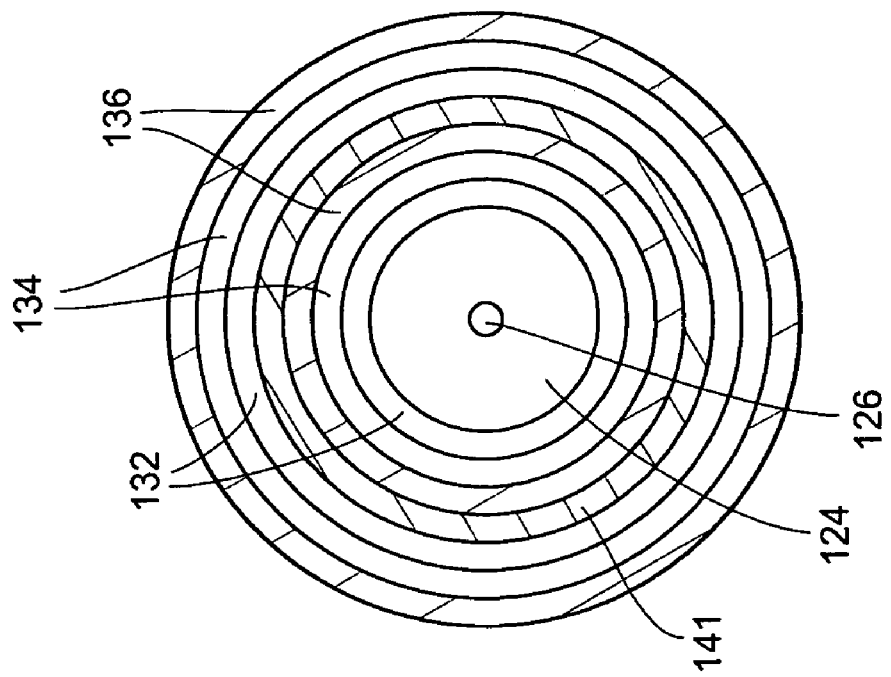
FIG. 13B is a sectional view of the medical device shown in FIG. 13A showing an embodiment wherein the nanoactuator encircles the medical device, according to the teachings of the disclosure.
Figure 13D:
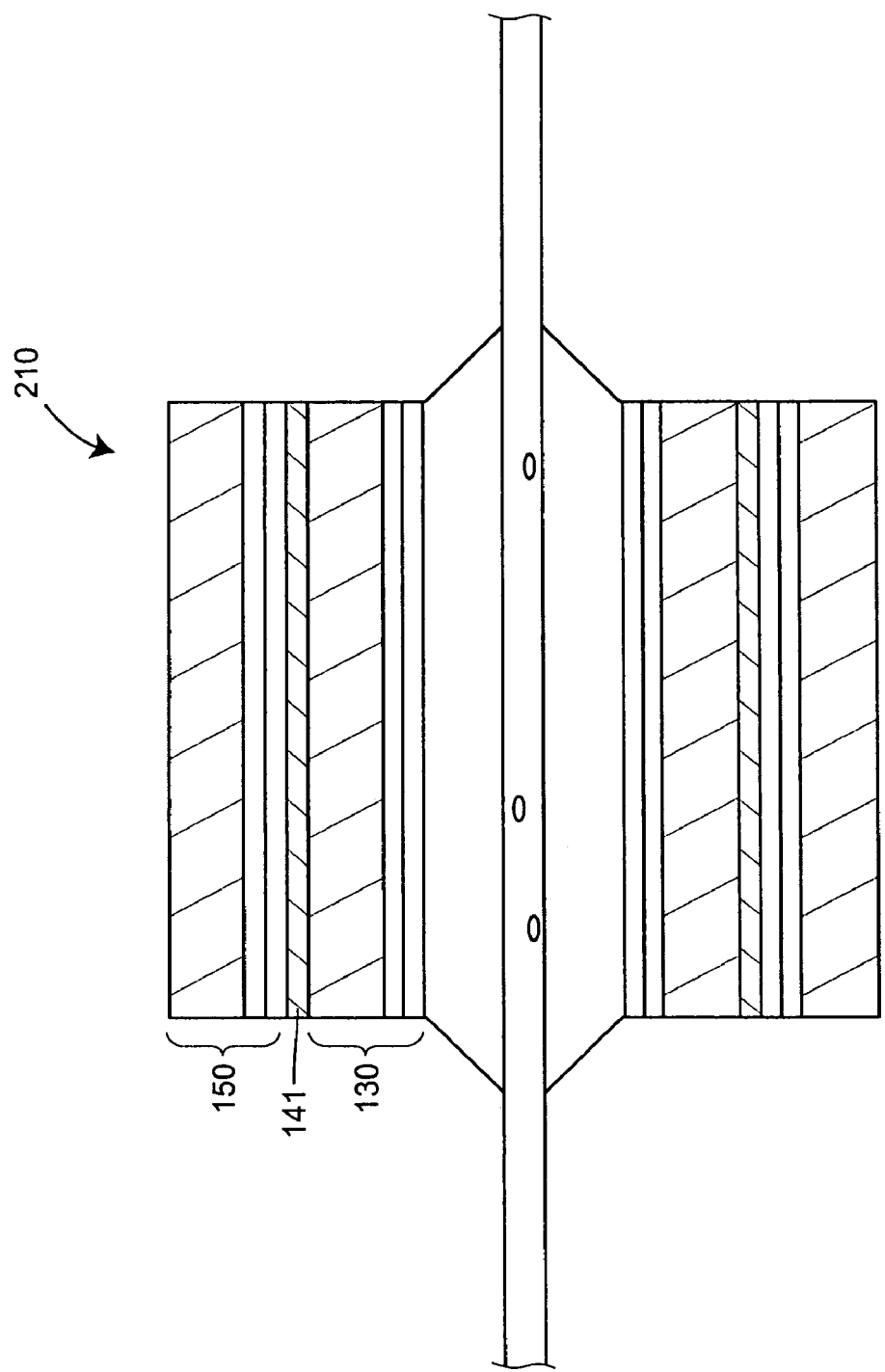
FIG. 13D shows the medical device of FIG. 13A, but in an activated state.
Figure 13F:
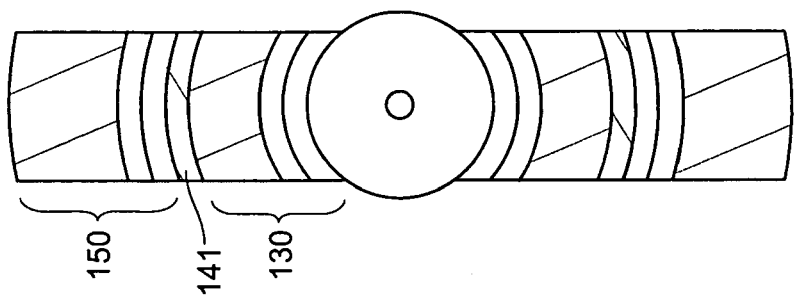
FIG. 13F is a section view of the medical device shown in FIG. 13D showing an embodiment wherein there are two nanoactuators positioned on opposing sides of the medical device, according to the teachings of the disclosure.
Figure 13E:
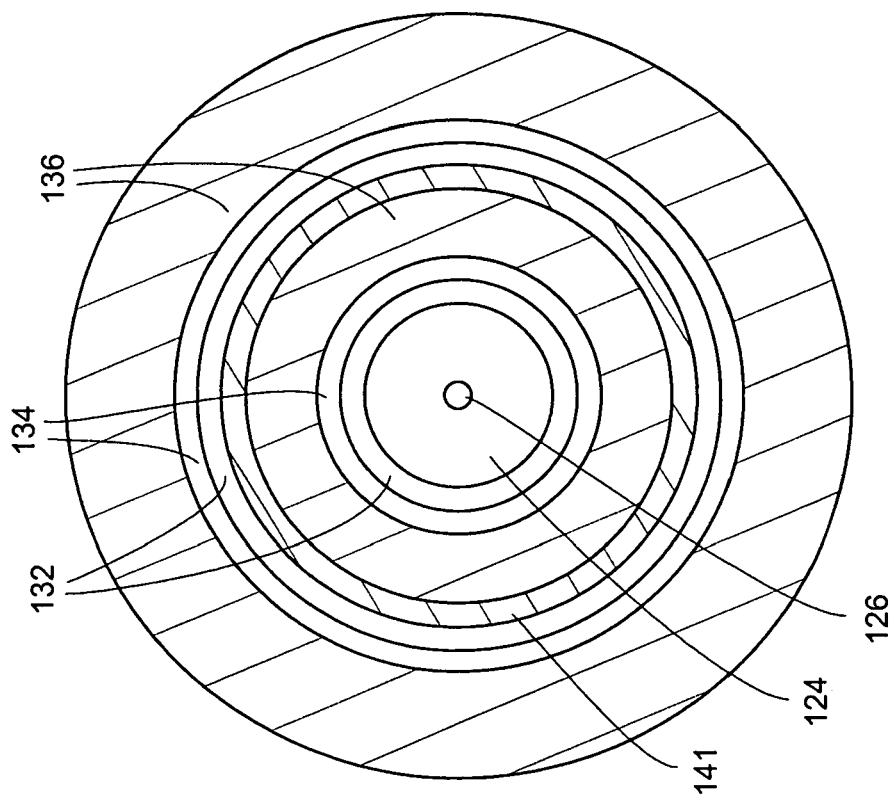
FIG. 13E is a sectional view of the medical device shown in FIG. 13D showing an embodiment wherein the nanoactuator encircles the medical device, according to the teachings of the disclosure.

In a still further embodiment, depicted in FIGS. 10 and 11, the deployable member 90 can be provided in the form of another medical device or pharmaceutical 98. More specifically, as opposed to a balloon 92, FIGS. 10 and 11 indicate that a medication or pharmaceutical 98 can be provided within the substantially rigid tube 76 proximate the open end 82. In order to maintain the pharmaceutical 98 in the rigid tube until deployment is desired, a frangible membrane 100 can be provided. The frangible membrane 100 is sufficiently strong to maintain the medication or pharmaceutical 98 within the substantially rigid tube 76 under low pressure, but upon expansion of the nanopaper 32, the resulting force of expansion as indicated by arrow δ is sufficient to overcome the frangible membrane 100, the frangible membrane 100 then ruptures, thus releasing the pharmaceutical 98. This design may be particularly advantageous when releasing pharmaceuticals, such as a contrast or the like for visualization purposes of a specific area of the lumen, or protein sequences, DNA or RNA which can be injected into the vessel wall. In addition, the deployable membrane 90 could be provided in the form of a separate medical device such as a membrane wire or gel for use in treating an aneurysm or the like. In some embodiments, the membrane 100 may be selectively porous so that when the nanopaper 32 expands, the resulting pressure opens membrane pores sufficiently to allow release of the pharmaceutical 98. In some embodiments, the membrane 100 may be provide at locations in addition to, or instead of, the open end 82 of the rigid tube 76.

In a further embodiment, a medical device or system 110 is provided as shown in FIGS. 12A-F. The medical device 110 may comprise a housing 112 with a proximal end 114 and a distal end 116. The proximal 114 and distal 116 ends in general refer to a region 118 of the housing 112 of particular interest, e.g., the region 118 comprising one or more nanoactuators 130. The medical device 110 may also comprise further proximal 115 and distal 117 regions. The nanoactuators 130 of the present disclosure may be found anywhere along the length of the housing 112, not just in the region 118 but also in proximal 115 and distal 117 regions.

From the foregoing, one of ordinary skill in the art will appreciate that the teachings of the disclosure can be used to construct an electrically actuated medical device for use in enlarging lumens or deploying other medical devices within lumens of the body or taking samples. In comparison to hydraulically actuated balloon catheters, it will be clear that there is no need for fluid access lumens. However, in some embodiments, including, but not limited to, those discussed below, such lumens may be present.

As shown in FIG. 12A, the medical device 110 is shown as a balloon catheter, but this is for illustrative purposes only. Other medical device embodiments include, but are not limited to, stents, medication supply devices, aneurysm coils and other devices discussed herein. In embodiments where the medical device 110 consists of or comprises a balloon catheter, the medical device may comprise a balloon 120. Either pneumatic or hydraulic balloons may be used or both. The medical device 110 and housing 112, including but not limited to, those embodiments with balloons 120, may comprise an exterior surface 122, and an interior 124. The medical device 110 may comprise an interior tube 126 in the interior 124. The inner tube 126 may provide one or more holes 128 that allow for inflation of the balloon 120, i.e., as an inflation lumen. The inner tube 126 may also provide a lumen for a guide wire or other components including, but not limited to the conductors 142, 144. While the balloon 120 is shown inflated, that is for illustrative purposes only, and in some embodiments the balloon 120 may be deflated while the actuator 130 is activated or deactivated. In other embodiments, balloon inflation may occur simultaneously with actuator activation, or may even constitute the same process as in those embodiments where the actuator 130 itself constitutes the balloon 120, see, e.g., medical device 510 discussed below in regards to FIGS. 16A and 16B.

The nanoactuator 130 may comprise a first electrode 132, a separator 134 and a second electrode 136. The first electrode 132 may comprise any number of conductive materials including, but not limited to, metal foils, gold, platinum, conductive polymers, and nanopaper 32. In some embodiments, the first electrode 132 may comprise the housing 112. The separator 134 may comprise a porous membrane including, but not limited to, a proton exchange membrane (PEM) that serves to electrically separate the two electrodes 132, 136. PEMs that may be utilized include, but are not limited to Nafion (which, for example, may comprise a Nafion solution of perfluorinated ion-exchange solution of approximately 5 percent by weight in mixture of lower aliphatic alcohols and water), and triblock copolymer ionomers such as sulfonated poly(styrene-isobutlyene-styrene) (S-SIBS). Nafion products including membranes and solution are available from ElectroChem, Inc. (Woburn, Mass.). Details and use of S-SIBS is provided in *Transport Properties of Triblock Copolymer Ionomer Membranes For Fuels Cells*, Y. A. Elabd, et al., 23rd Annual Army Science Conference Oral Paper AO-02. (2002), the disclosure of which is expressly incorporated herein by reference. In some embodiments, the separator 134 may comprise a material that has holes introduced into it using a laser, such materials include without limitation Tecothane® and ceramics. In some embodiments the separator 134 comprises a nanoporous electrical isolator and/or a microporous electrical isolator. The description of materials described for the separator 134 are also applicable toward the porous membrane 48, and vice versa. The second electrode may comprise nanopaper 32, the composition and manufacture of which have been described herein. Single or multiple layers of nanopaper may be employed in a given electrode. In some embodiments, the first electrode 132 may also comprise nanopaper 32.

An electrolyte 138 is provided in the actuator 130 so as to allow for a completed electrical circuit between the first and second electrodes 132, 136. The electrolyte 138 may be carried in a suitable fluid 139 to yield an electrically conductive solution. The electrolyte 138 and fluid 139 operatively associated with the separator 134 and first and second electrodes 132, 136. The electrolyte 138 may provide an ion that allows for formation of a gas that will form upon activation of the actuator, the gas forming microbubbles 52, e.g., of oxygen, chlorine, etc., causing expansion of the nanopaper 32 as described herein for the system 20. The nanoactuator(s) 130 shown in FIGS. 12A-C is in a non-activated state. Suitable electrolytes 138 include, but are not limited to, sodium chloride and hydrogen chloride. One will appreciate that the choice of electrolyte 138 and fluid 139 will be influenced by whether the actuator 130 is to be open to, i.e., fluidically associated with, body fluids. The description for the electrolyte 138 and fluid 139 are also applicable to those for the electrolyte 31 and fluid 41, and vice versa.

Figure 14A:
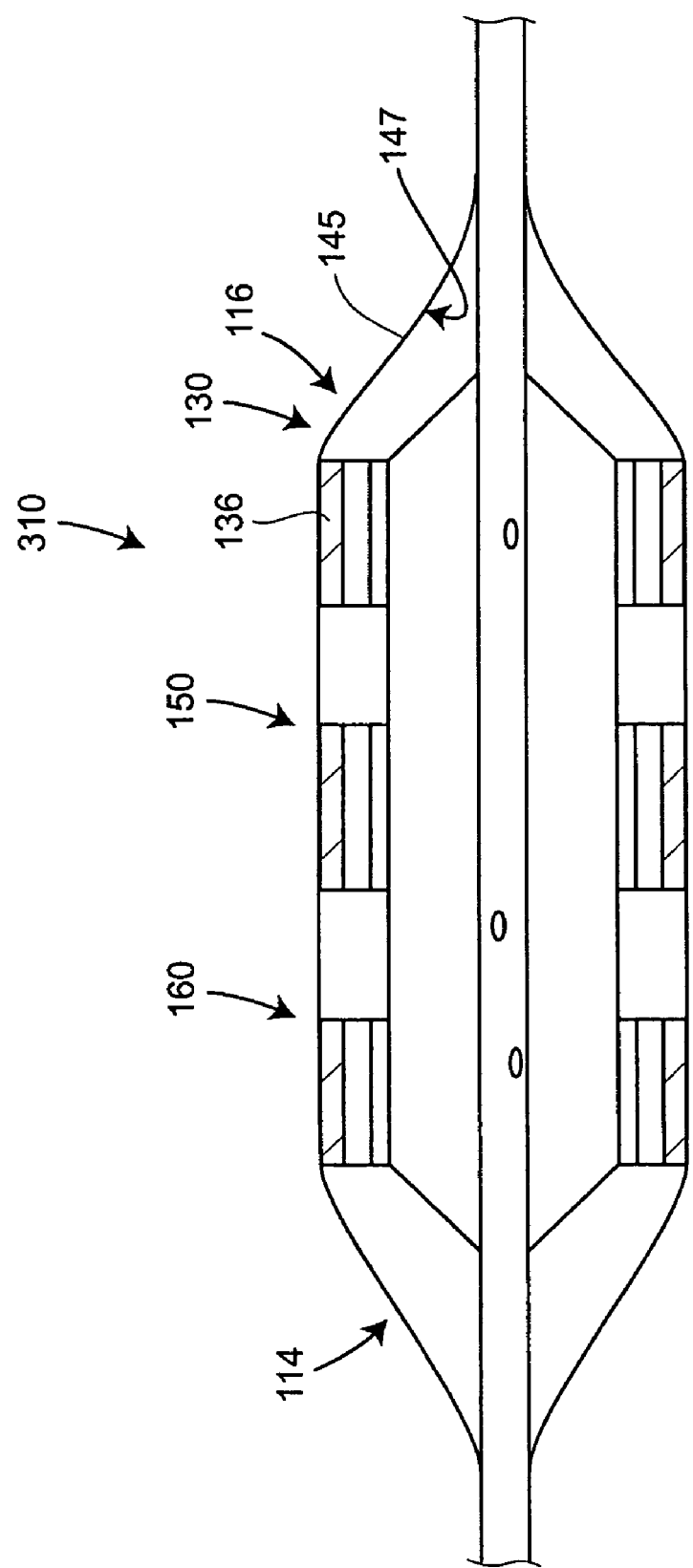
FIG. 14A is an alternative embodiment of the medical device shown in FIG. 12A, according to the teachings of the disclosure.

The actuator 130 may have an outer surface 140 suitably designed in respect to exterior environment of the medical device 110, which may depend on the particular application to which the medical device 110 is applied. During assembly, the components of the actuator 130 may be pressed together at between 130° C. and 150° C. to create a robust interface. In some embodiments, during assembly, the polymer components of the actuator 130 may be pressed together near the melting temperatures of the polymer components to create a robust interface. In some embodiments, nanopaper of 15 to 35 micrometers in thickness is used. In some embodiments, the actuator comprises 15 micrometer thick nanopaper, 5 micrometer thick Nafion membrane and 0.1 micrometer platinum foil (e.g., from supplier as the Lebow Company, Goleta, Calif.) to yield an approximately 20 micrometer thick actuator. In some embodiments, Nafion membranes from 0.002" to 0.017" thickness may be used (e.g., from Sigma Aldrich, Milwaukee, Wis.). These ranges and values do not serve as limitations on the dimensions of the actuator and its constituents. Thicker actuators may also be achieved by stacking actuators, see, e.g., the description of medical device 210 below. The layers of the actuator may be hot-pressed together before wrapping the actuator around a surface 122 of the housing 112 or balloon 120. Means of connecting the actuator 130 to the housing 112 or balloon 120 include glue and outer sheaths 145 (e.g., as shown in FIGS. 14A and 14B). Examples of glues include, but are not limited to, cyanoacrylics, polyurethanes, and UV curable glues. The actuator may also be sewn together on the housing 112 or balloon 120, or attached with clamps.

An outer sheath 145 comprising a porous elastic membrane may allow use of blood plasma or other body fluids as the electrolyte 138 and fluid 139. In those embodiments wherein the actuator components are not open to the environment, the components may be presoaked with an appropriate electrolyte 138 in an appropriate fluid 139. Components may also be presoaked when open to the environment. The actuator 130 or components thereof may be molded in the shape of a particular medical device. Examples of such devices may include, without limitation, Congestive heart failure devices, septal defect repair devices, valve treatment devices, aneurysm repair, ear canal repair devices, retrieval devices, urological devices, lesion treatment, and septal closure devices. In some embodiments, the outer sheath 145 is not porous, e.g., as in those embodiments where the actuator components are presoaked. However, even in those embodiments with a porous outer sheath, the components may still be presoaked. In some embodiments, the outer sheath 145 may comprise some or all of the qualities described for the outer sheath 34. The outer sheath 145, it can be manufactured from any polymeric material. In some embodiments, the sheath 145 comprises a elastomeric material. Outer sheath 145 may comprise, but is not limited to, latex, rubber, silicon rubber, Pebax®, urethane, pelothane, Tecothane®, polyester isobutyl styrene, epoxies and thermoplastics.

The first and second electrodes 132, 136 may be operatively associated with a power source 146 by means of first and second conductors 142, 144, respectively. The power source 146 may be immediately adjacent to the actuator 130 or may be present in a proximal region 115 or distal region 117 of the medical device. The power source 146 may also be external to medical device 110 and connected to the medical device by conductors 142, 144. In some embodiments, the power source 146 may comprise a battery. In some embodiments, the battery may be operatively associated with, including, but not limited to, immediately adjacent to, the medical device 110 in region 118, or proximal 115 or distal 117 regions. In some embodiments, the conductors 142, 144 may comprise, but are not limited to, wires comprising gold, platinum, conductive polymers, or combinations thereof. A conductive ring 36, as described in relation to system 20, may also be employed. In some embodiments, the power source 146 may be operatively associated to the actuator 130 by wireless means.

The power source 146 should apply sufficient power to supply a voltage sufficient for the formation of gas bubbles from the electrolyte 138 when activating the actuator 130, and sufficient voltage to reverse that chemical process when deactivating the actuator 130. A power source 146, and conductors 142, 144, may be employed with any of the embodiments shown in the figures regardless of whether the power source and conductors are depicted in a particular figure. The power source 146 may supply direct current. The embodiments described for power source 146 are also applicable to power sources 46 and 94, and vice versa. Similarly, the embodiments described for conductors 142, 144 are also applicable to conductors 42, 44 and vice versa.

FIG. 12A is a partial longitudinal sectional view of the medical device 110. FIGS. 12B and 12C, respectively, demonstrate two different, possible lateral sectional views of the medical device 110 as shown in FIG. 12A. FIG. 12B is representative of embodiments of the medical device 110 wherein the actuator 130 extends continuously about an outer perimeter (e.g., diameter) 113 of the housing 112 (or in some embodiments the balloon 120) to constitute a single actuator 130. FIG. 12C is representative of embodiments wherein the medical device 110 comprises two or more actuators 130 disposed about the outer perimeter 113. As shown in FIG. 12C, there is a first actuator 130 and a second actuator 150 diametrically opposed to one another. However, this number and arrangement is for illustrative purposes only, as particular embodiments may have any number of actuators in any number of different arrangements and orientations.

In some embodiments, the actuator 130 is disposed around not an outer perimeter 113, but rather about a portion of the wall 121 of the housing 112 (or balloon 120) so that the actuator 130 is located both within the interior 124 and along an exterior surface 122 of the housing 112. Embodiments comprising more than one actuator 130 may be so configured so that the individual actuator may be activated collectively or independently. In some embodiments, groups of actuators may each be activated collectively, with each group being capable of being activated independently of the other groups. Further embodiments and aspects of embodiments including multiple actuators are discussed in greater detail below.

FIGS. 12D, E, and F, corresponding to FIGS. 12A, B and C, show the medical device 110 in an activated state. As depicted in FIGS. 12D-F, activation of the nanoactuator has expanded radially the thickness θ of the second electrode 136 comprising the nanopaper 32 as described herein, which has consequently increased the overall width/diameter Φ of the medical device 110. The features, elements, and properties discussed in relation to system or medical device 110 are applicable to the other systems or medical devices described, and vice versa, unless otherwise noted.

FIGS. 13A-F show an embodiment wherein a medical device 210 comprises at least two actuators with a second actuator 150 surrounding the first actuator 130. FIGS. 13A-F are also analogous to FIGS. 12A-F in respect to non-activated and activated states, sectional views and elements shown. The first and second actuators 130, 150 may be joined by a partition 141. The partition 141 may comprise an insulator or a (an intervening) separator. The insulator may comprise, without limitation, ceramics, non-conductive polymers, poor conductors, latex, rubber, silicon rubber, Pebax®, urethane, pelothane, Tecothane®, polyester isobutyl styrene, epoxies and thermoplastics. An intervening separator may have the same properties of separators 48 and 134. In the embodiment shown in FIGS. 13A-F, the first and second actuators 130, 150 have the same orientation. The partition 141 may comprise a separator when the two adjacent actuators have the same orientation in respect to the arrangement of the first electrode 132 and second electrode 136 of each conductor 130, 150. When two adjacent actuators have opposing orientations, the partition 141 may comprise an insulator. In embodiments such as those shown in FIGS. 13A-F, the actuators may be operatively associated with a power source 146 so that the actuators may be activated independently or collectively. Any number of actuators may be "stacked" on one another, FIGS. 13A-F depict two stacked actuators for illustrative purposes only. Stacked actuator arrangements such as those shown in respect to medical device 210 may also be employed in the other systems and medical devices herein described.

FIGS. 14A and 14B show a medical device 310 and are representative of some embodiments having multiple actuators. For illustrative purposes only, the medical device 310 is shown with a first actuator 130, a second actuator 150 and a third actuator 160. While specific lateral sectional views are not provided for medical device 310, such views are analogous to those shown in FIGS. 12B, C, E and F. In some embodiments, the medical device, e.g., 310, may have only a first actuator 130 at distal end 116, or only a third actuator 160 at the proximal end 114, or only a second actuator 150 in the middle. Such embodiments allow medical devices such as balloon catheters to be tapered, thus achieving a tapered profile. Tapering can also be achieved in whole or part by differential stacking of actuators on different areas of the medical device. Selective and timed activation of actuators may also be employed in a manner similar to that described herein for some embodiments of method 180.

The medical device 310 may comprise an outer sheath 145 that surrounds the actuators 130, 150 and 160. The sheath 145 may further comprise an interior surface 147 to which a conductive element is applied. Such a conductive element may be used to electrically connect the individual actuators.

Individual actuators may also be connected together with a conductive layer applied to the surface 122 of the housing 112. Such a layer may include, but is not limited to, gold and conductive carbon, and those materials described for conductors 42, 44, 142 and 144. As described herein, the individual actuators may be activated (and deactivated) together or independently. The outer sheath 145 may be provided on any embodiment of any medical device of the present disclosure and is shown in connection with medical device 310 for illustrative purposes only. In some embodiments individual actuators are connected using connectors, e.g. 142, 144, such as wires. These means of connecting individual actuators are shown for illustrative purposes only, and so are not meant to be limiting.

No limits are contemplated as to ways for attaching an outer sheath 34 or 145. In some embodiments, the outer sheath, e.g., 145 (description for 145 also applicable to 34, and vice versa) expand by exposing the outer sheath 145 to a solvent it can absorb. The absorption of the solvent will expand the outer sheath 145, allowing the insertion of the nanoactuator 130 into the outer sheath 145. Evaporation of the solvent allow the outer sheath to contract, in some embodiments to its original diameter. Appropriate outer sheath 145 materials for such uses include without limitation Tecothane® (aromatic polyether-based polyurethane) using Toluene as the expansion solvent. This method may also be employed in covering crimped stents. Tecothane® is an elastic polymer which comes into a variety of hardnesses. Appropriate Tecothane® varieties, include without limitation, soft varieties, e.g., 74A and 85A, which may provide 100% expansion, and harder varieties, e.g., 95A, which may provide 50% expansion.

The outer sheath 145 may be polymeric without being elastomeric or not completely elastomeric. The sheath can plastically deform as well as elastically deform both during assembly (or re-assembly) of the medical device or during operation (use) of the medical device. The outer sheath after retracting need not obtain its original diameter. In addition to solvent methods described herein, shrink wrapping of the outer sheath 145 over the actuator 130 may be performed using heat, e.g., through a glass transition temperature. In some embodiments the outer sheath 145 may be free blown. In other embodiments, the outer sheath 145 may be formed using a mold. For illustrative purposes only, Tecothane® may be free-blown and re-shrunk using heat. Another example, again without limitation, is Pebax, which may be blown (either free-blown or in a mold) and re-shrunk. Others suitable polymers include without limitation pellathane, polyolefins, and polyesters. As the wall 121 of the balloon 120 is analogous to the outer sheaths 34 and 145, the above described assembly processes are also applicable to the manufacture of medical devices including without limitation the medical device 410 shown in FIGS. 15A and 15B.

Figure 15B:
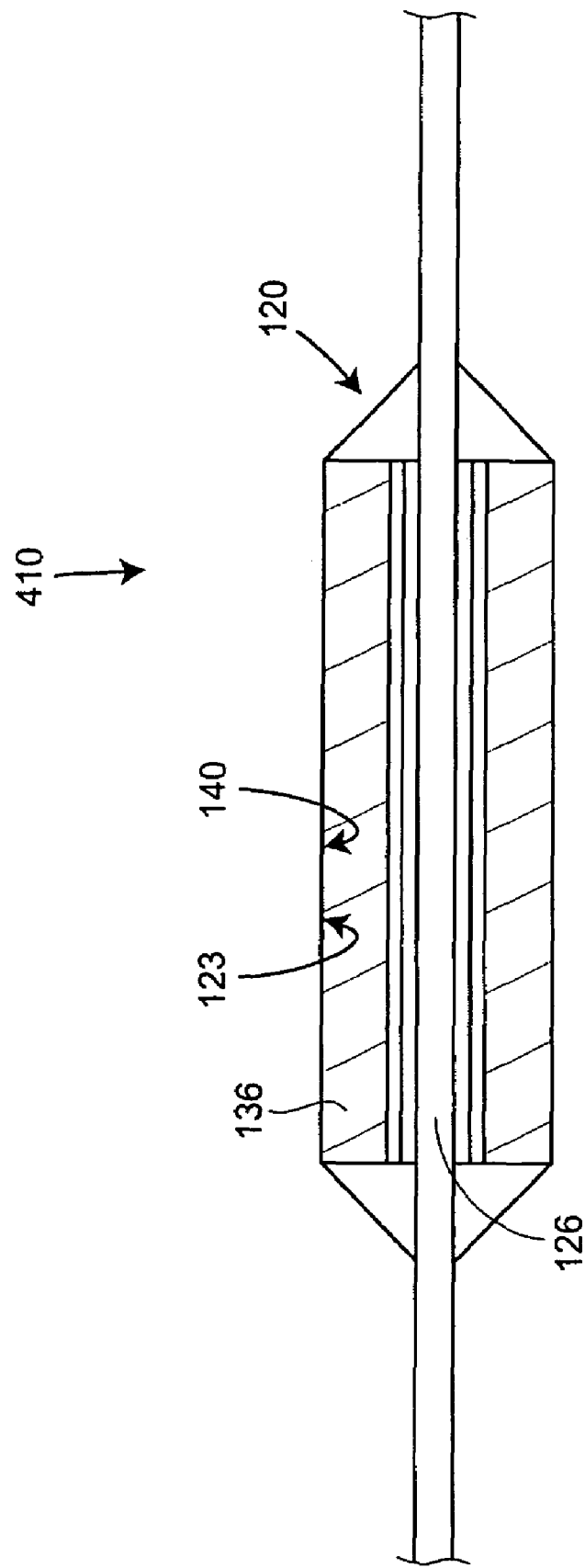
FIG. 15B shows the medical device of FIG. 15A, but in an activated state, according to the teachings of the disclosure.

FIGS. 15A and 15B show a medical device 410 wherein the actuator 130 is within an interior 124 of the housing 112. In the embodiment shown, the actuator 130 is more specifically within the interior 124 of a balloon 120. In FIG. 15A, the actuator 130 is in a non-activated state. The interior of the housing 112 or balloon 120 may comprise an interior surface 123. In FIG. 15B, the actuator is in an activated state with the outer surface 140 of the actuator 130 pressing against the interior surface 123 of the balloon 120. The balloon 120 may then be expanded without the need for inflating with fluid (gas or liquid) using the inner tube 126 and holes 128 therein as depicted in preceding figures. In fact, such tube 126 and holes 128 need not be present in such embodiments, such that the first electrode 132 is solid as depicted by 30 in respect to system or medical device 20. While specific lateral sectional views are not provided for medical device 410, such views are analogous to those shown in FIGS. 12B, C, E and F, 22B and 22D. In some embodiments, the actuator 130 remains in contact with the interior surface 123 when the actuator 130 is in an activated state and a non-activated state.

Figure 16A:
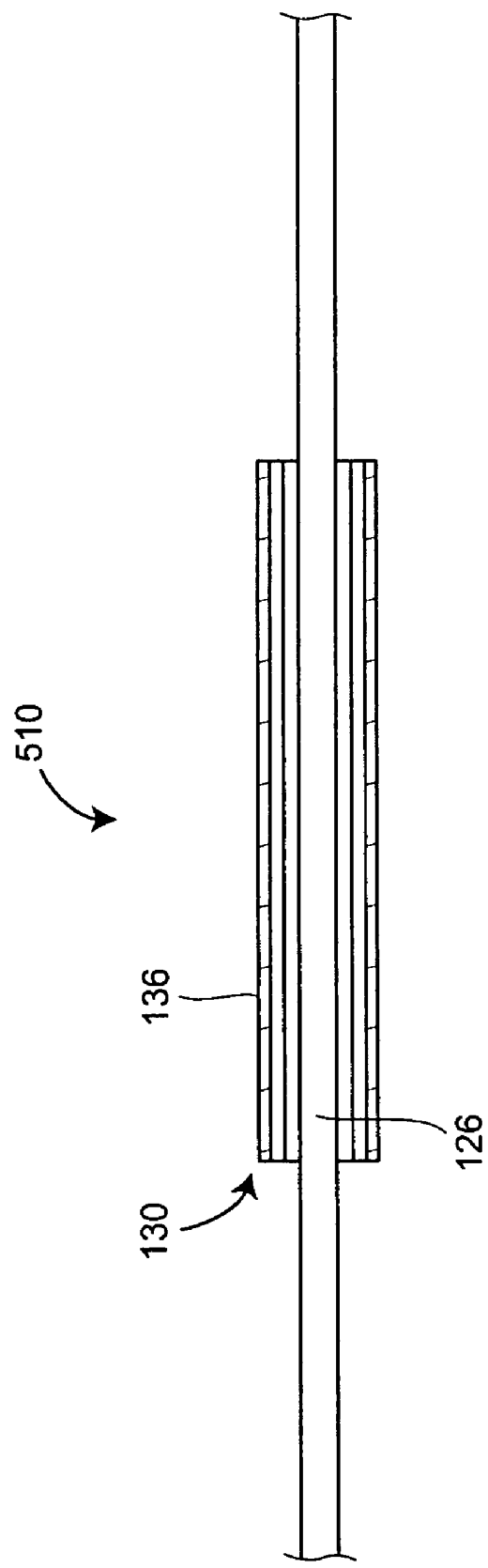
FIG. 16A is a longitudinal sectional view of a medical device with a nanoactuator, in a non-activated state, according to the teachings of the disclosure.
Figure 16B:
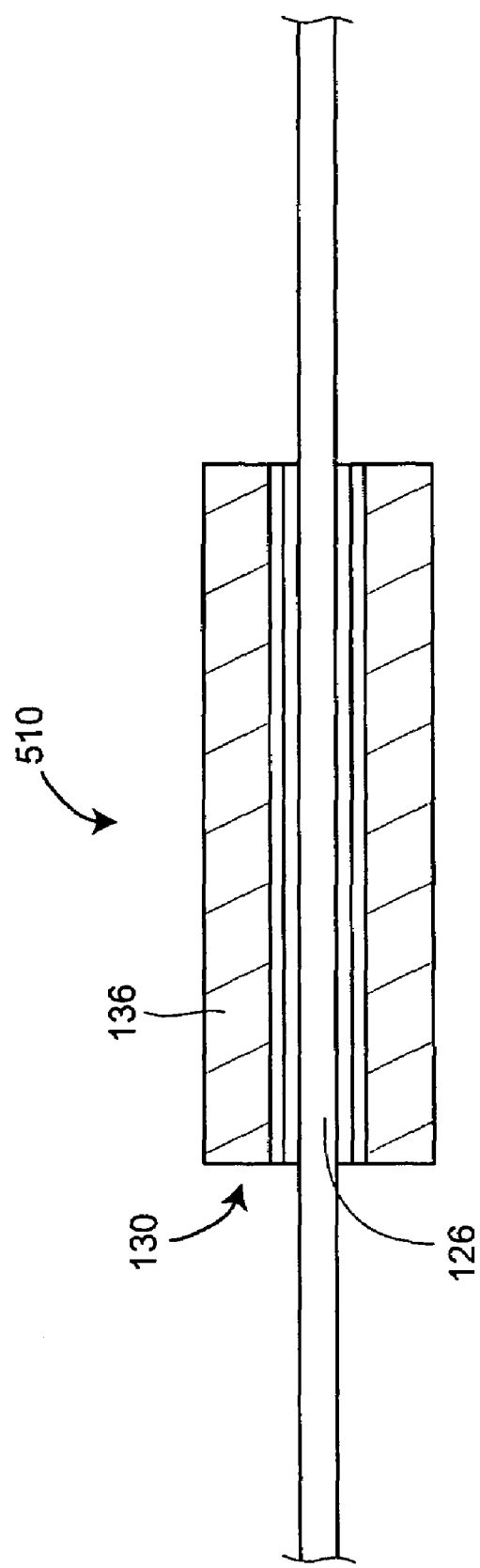
FIG. 16B shows the medical device of FIG. 16A, but in an activated state, according to the teachings of the disclosure.

FIG. 16A and FIG. 16B show a medical device 510, constituting a variation on the embodiment shown in FIGS. 15A and B, in which no separate balloon 120 is present. The second electrode 136 comprising the nanopaper 26 acts as a balloon by itself. In such embodiments, no inner tube 126 or holes 128 therein are necessary. While specific lateral sectional views are not provided for in medical device 510, such views are analogous to those shown in FIGS. 12B, C, E and F, 22B and 22D. In some embodiments, wherein an inner tube 126 is present, an actuator 130 may be used to control the stiffness of the tube 126, e.g., a catheter shaft, in part or in entirety. Such a use results in higher efficiency to transfer push force exerted from the proximal end (or region 115) to distal end (or region 117) of a catheter or other medical device, i.e., so called "pushability."

Figure 17:
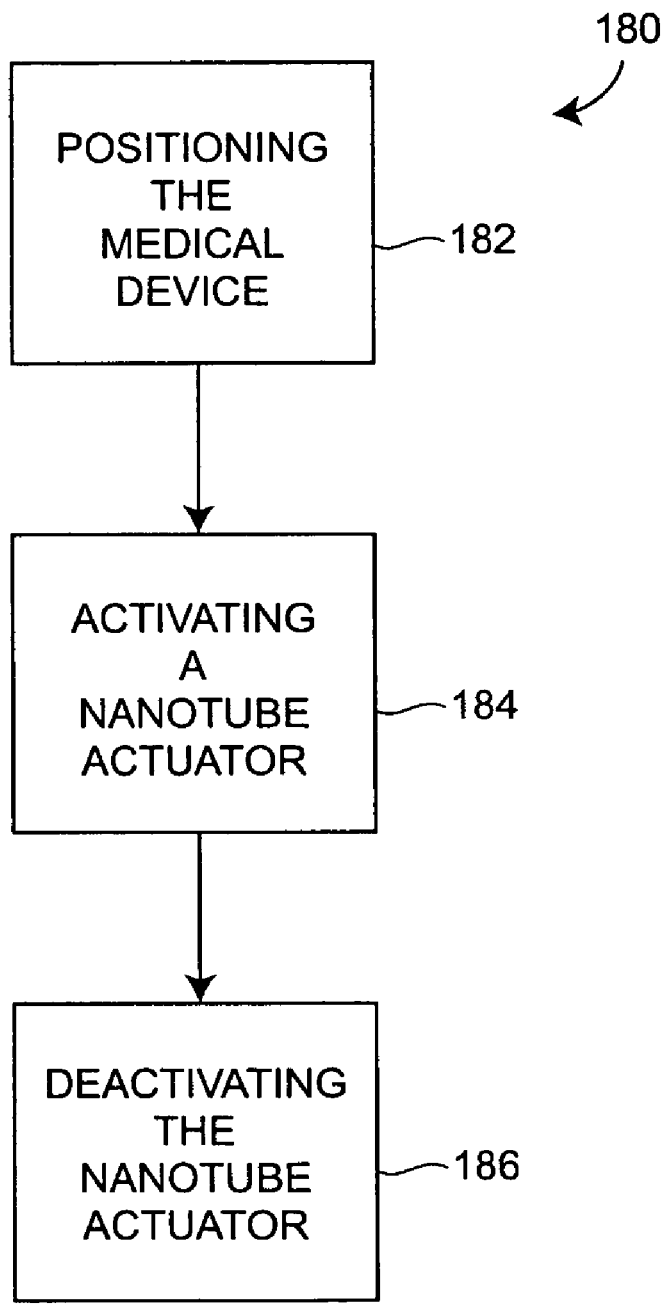
FIG. 17 is a flow chart showing a method of using a medical device with a nanoactuator, according to the teachings of the disclosure.

FIG. 17 provides a general method 180 for utilizing the medical devices and systems of this disclosure, including, but not limited to 20, 110, 210, 310, 410, 510, 610, 710, 810, 910, 1110, 1210, 1310, 1410, 1510, 1610, 1710, 1810, and 1910. The method 180 may comprise a first step 182 of positioning the medical device in a body lumen and a second step 184 of activating a nanoactuator operatively associated with the medical device by applying voltage causing microbubbles 52 to form and expand nanopaper within the nanoactuator. The method 180 may also comprise the step 186 of deactivating the nanoactuator by reversing the voltage sufficiently such that the microbubbles degenerate. One will understand that the actuator may be left in an activated state indefinitely, although over time the actuator may slowly or rapidly (or spontaneously) return to a deactivated state without reversing potential.

In some embodiments, the method 180 may be employed using a medical device 310 as shown in FIGS. 14A and 14B such that the first actuator 130, second actuator 150, and third actuator 160 are activated in sequence so that the width (diameter) Φ, as depicted in FIG. 12D, of the medical device is increased starting with the distal end 116 of the balloon to the proximal end 114. In other embodiments, the order of activation is reversed. In some embodiments, the second actuator 150 is activated first and then the first 130 and third 160. In other embodiments, the first and third actuators 130, 160 are activated first, and then the second 150. In some embodiments, a number of actuators other than three are involved. In other embodiments of method 180, successive deactivation of actuators is employed. Embodiments of method 180 employing medical devices such as 310 as well as other embodiments of the present disclosure demonstrate that the medical devices of the present disclosure can be used to achieve a tapered profile. The method 180 as well as the other methods and devices of the present disclosure may be employed to deploy stents to prevent "barbelling" and other undesired results. The various medical devices of this disclosure may also be used to help prevent "watermeloning" difficulties that may be associated with certain medical devices.

In some embodiments, the medical device 310 may have a means for drug delivery. In some embodiments the drug delivery means takes the form of a lumen that may be filled with a drug (pharmaceutical) with side ports or other opening provided in the lumen housing to allow for release of drug that may be activated by syringe means. Such holes may be located at various positions of the medical device 310, including, but not limited to, the area between the actuators and through an opening drilled through the second actuator 150. In some embodiments, the drug lumen may be C-shaped, but other shapes may be used as well. The drug may comprise, but is not limited to, placitaxel, microparticles, and those pharmaceuticals and biologically active substances described herein in reference to blade-released pharmaceutical embodiments. In some embodiments, the medical device 310 may provide an additional lumen allowing for blood bypassing. In such embodiments, proximal to the most proximal actuator is a sidehole that allows blood to flow into the lumen, and the lumen may have an exit distal to the most distal actuator. This configuration allows for sustained blood flow during the procedure as described herein.

The medical device 310 may be used to deliver a drug to a particular area of a body lumen. In some embodiments, the middle actuator 150 is first actuated to open up a stenosis in an area that may or may not contain a stent. The second actuator 150 is deactivated and the first and third actuators 130 and 160 are activated to create a temporary chamber. Drug may then be deployed in the chamber. After the drug has been administered, and optionally allowed to incubate or react with surrounding surfaces (tissue, medical device or other surfaces), the first and third actuators 130 and 160 may be deactivated. The device 310 may then be removed.

In some embodiments, the medical device, e.g., 110, is a balloon catheter and the balloon 120 is in a non-inflated state. For example, the balloon 120 may be "wing-folded," a practice that allows the balloon to be more easily fit into a body lumen. Activation of the actuator 130 is then used to unfold the balloon. When wing-folded, the actuator may be itself triple-folded. Embodiments with the actuator 130 in an interior 124 and supported by the inner tube 126 allow full 30 bar stress pressure to open up calcified lesions. The activator 130 may be activated regardless of whether the balloon 120 is inflated or deflated independent of the actuator, e.g., hydraulically, pneumatically, etc. One will also appreciate that the medical devices, e.g., 110, of the disclosure can achieve cone angles σ of up to and including 90° for the actuator 130, whereas cone angles τ for the balloon 120 itself generally are difficult to achieve a 90° cone angle.

Figure 18D:
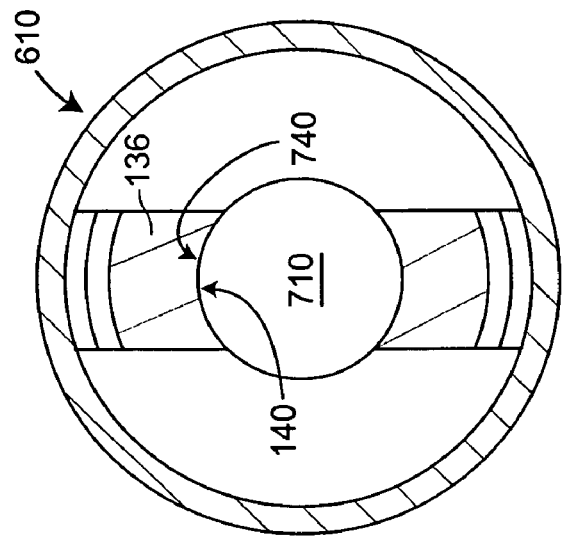
FIG. 18D is one embodiment of a sectional view of the first and second medical devices shown in FIG. 18C, according to the teachings of the disclosure.

FIGS. 18A-D show a medical device 610 positioned so as to surround a second medical device 710. At least one nanoactuator is operatively associated with the housing 112 in a manner substantially similar to that described in respect to medical device 110. The housing 112 may be made of a variety of materials including, but not limited to, metals and conductive polymers. The first medical device 610 may further comprise a handle 170 and the second medical device 710 may have an outer surface 740. FIG. 18B is a lateral sectional view of medical devices 610, 710 analogous to that shown in FIG. 12C, except that in FIG. 18, the actuator(s) is orientated inwards. This view is for illustrative purposes only as the actuator 130 may in some embodiments extend about the entire inner perimeter (circumference) 613 of the housing 112 of medical device 610 analogous to that shown in FIG. 12B, except that in FIG. 18, the actuator(s) is orientated inwards. Such embodiments may provide a seal owing in part to the extent of the actuator. And, as described herein, the medical device 610 may comprise any number of actuators 130. In some embodiments, actuators are provided instead on the second medical device 710, and in still others, actuators may be provided on both first and second medical devices 610, 710. In some embodiments, the first medical device 610 may comprise in the alternative or in addition to the handle 170, an opening allowing for the second medical device 710 to pass through the first medical device 710.

Figure 18C:
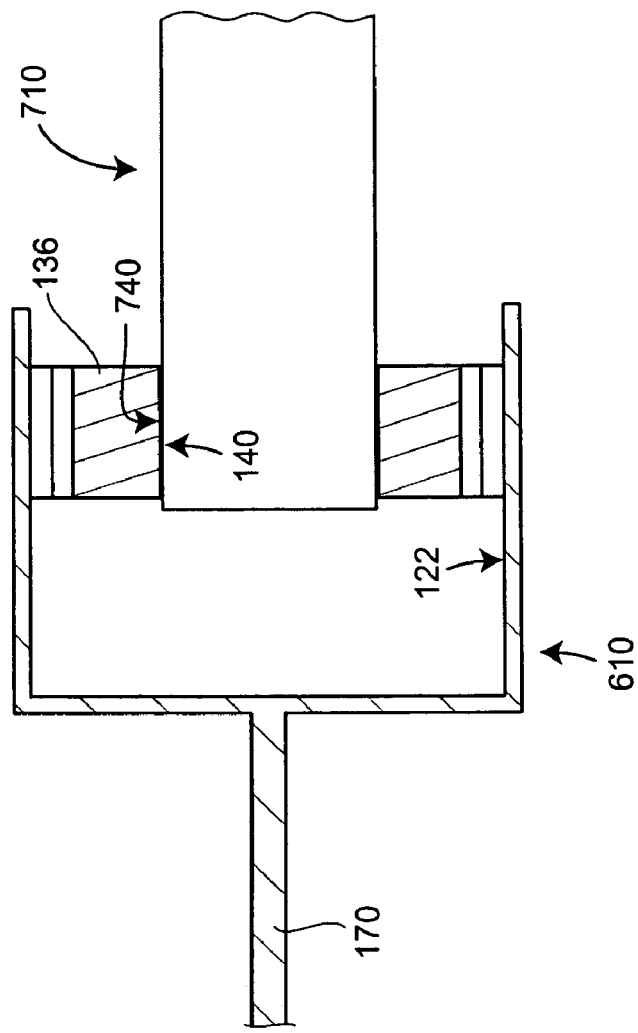
FIG. 18C shows the first and second medical devices of FIG. 18A, but with the nanoactuator in an activated state.

While FIGS. 18A and 18B show the actuator 130 in a non-activated state, FIGS. 18C and 18D show the actuator in an activated state. In such an activated state, the outer surface 140 is in contact with the outer surface 740 so that the first medical device 610 is gripping the second medical device 710. Surfaces 140 and 740 may be designed to provide a firm grip when the actuator(s) is activated so as to prevent slippage from occurring. In some embodiments, the surfaces 140 and 740 (as well as 940 described herein) may be designed to provide a slideable seal. In some embodiments, the slideable seal may be a piston driven by a hydraulic fluid, e.g., a saline solution, in the interior of the housing. If the actuator (seal) is opened after the sliding action is concluded, the piston and connected parts can be left behind in the body. In some embodiments, the slideable seal may be used in association with an aneurism coil. In some embodiments, the slideable seal may comprise a Teflon ring.

Figure 19D:
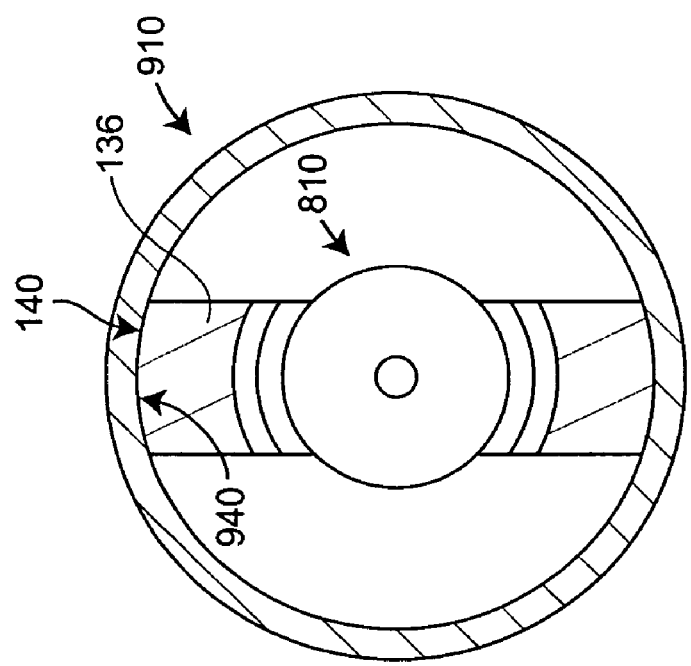
FIG. 19D is one embodiment of a sectional view of the first and second medical devices shown in FIG. 19C, according to the teachings of the disclosure.

FIGS. 19A-D show a medical device 810 positioned within a second medical device 910. At least one nanoactuator is operatively associated with the housing 112 in a manner substantially similar to that described in respect to medical device 110. The first medical device 810 may further comprise a handle 170 and the second medical device 910 may have an inner surface 940. FIG. 19B is a transverse sectional view of medical devices 810, 910 analogous to that shown in FIG. 12C. This view is for illustrative purposes only as the actuator 130 may in some embodiments extend about the entire outer perimeter (circumference) 113 of the housing 112 of medical device 810 analogous to that shown in FIG. 12B. Such embodiments may provide a seal owing in part to the extent of the actuator. And, as described herein, the medical device 810 may comprise any number of actuators 130. In some embodiments, actuators are provided instead on the second medical device 910, and in still others, actuators may be provided on both first and second medical devices 810, 910.

Figure 19C:
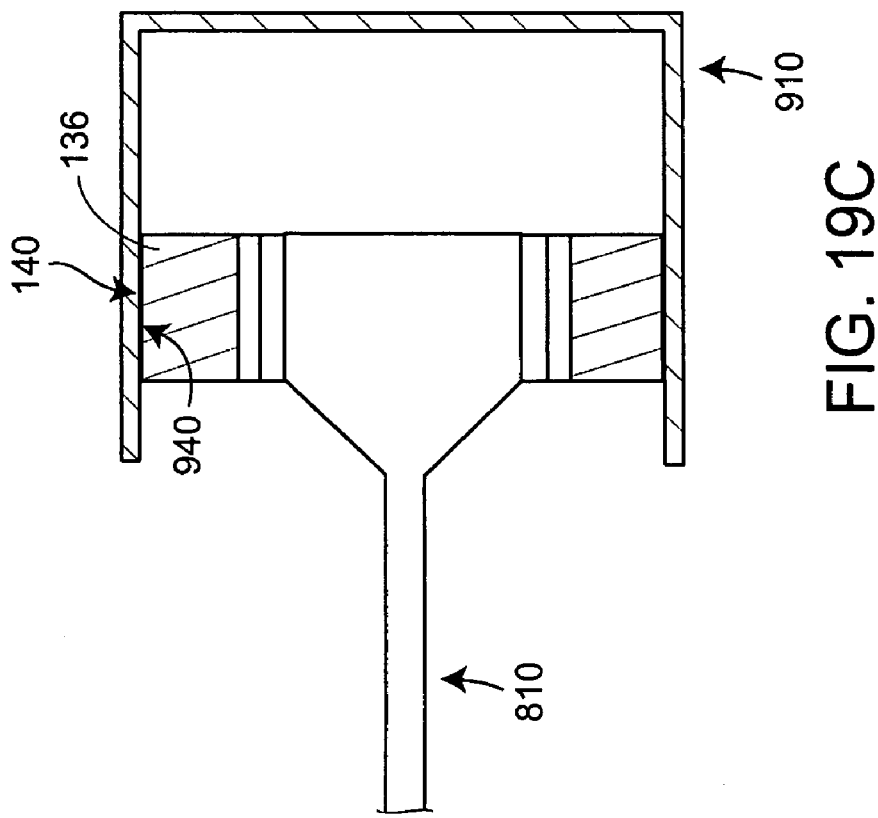
FIG. 19C shows the first and second medical devices of FIG. 19A, but with the nanoactuator in an activated state.

While FIGS. 19A and 19B show the actuator 130 in a non-activated state, FIGS. 19C and 19D show the actuator in an activated state. In such an activated state, the outer surface 140 is in contact with the outer surface 940 so that the first medical device 810 is gripping the second medical device 910. Surfaces 140 and 940 may be designed to provide a firm grip when the actuator(s) is activated so as to prevent slippage from occurring. In some embodiments, the surfaces may be designed to provide a slideable seal, e.g., as described herein.

Figure 20:
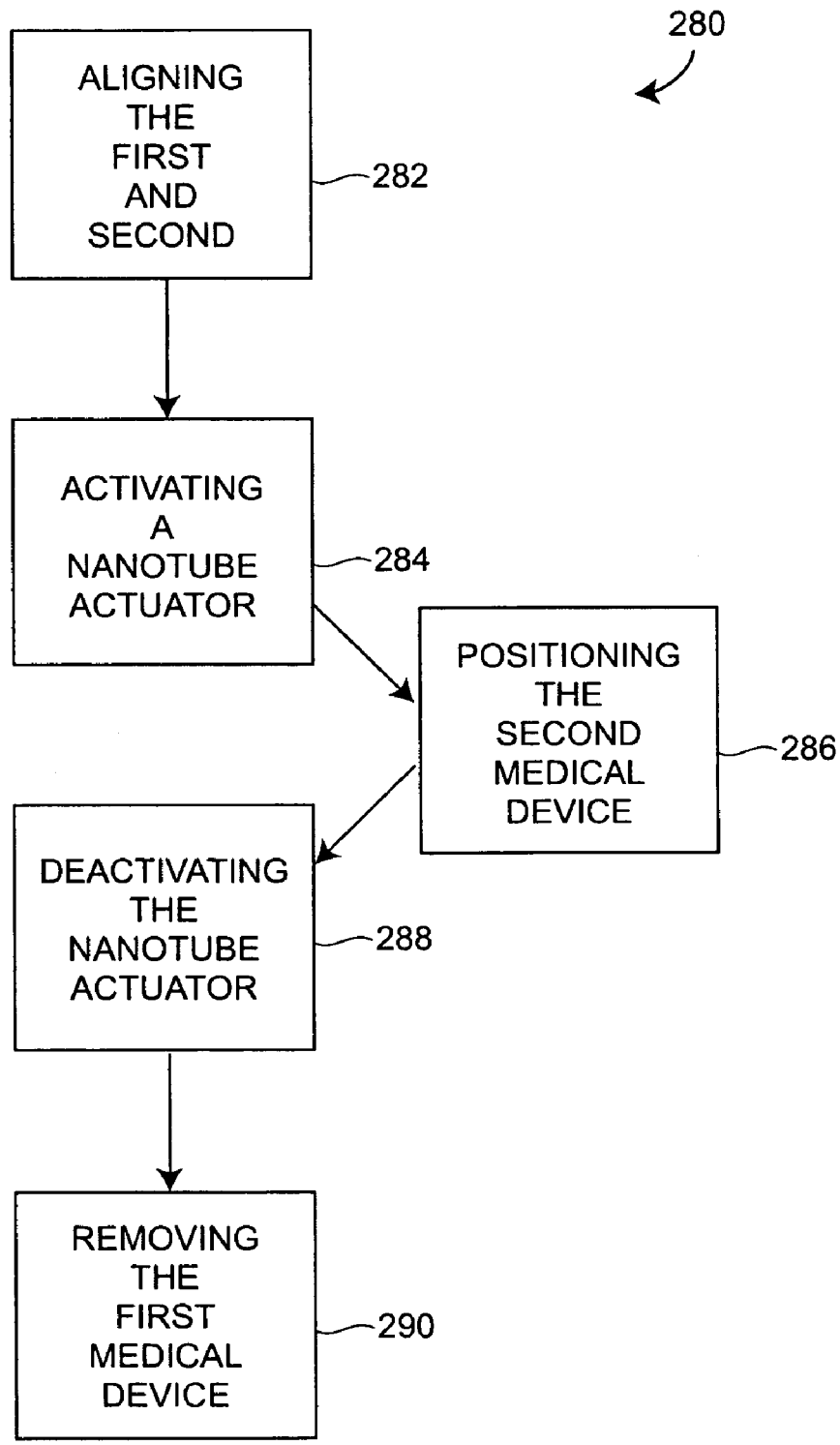
FIG. 20 is a flow chart depicting a method of using a first medical device as a clamp to grip and deliver a second medical device, according to the teachings of the disclosure.

FIG. 20 depicts a method 280 for using medical devices, e.g., the medical devices or systems shown in FIGS. 18 and 19, such that a first medical device is used as a clamp to grip second medical device. The method 280 may comprise a step 282 aligning the first and second medical devices relative to one another to prepare the second device to be gripped by the first, a step 284 of activating a nanoactuator operatively associated with a housing of the first medical device, and a step 286 of positioning the second medical device in a desired location within a body lumen. The method 280 may further comprise a step 288 of deactivating the nanoactuator. The step 288 is generally performed after the second medical device has been positioned in a desired location. The method 280 may still further comprise a step 290 of removing the first medical device. The step 290 is generally performed after the actuator is deactivated. In some embodiments, the actuator(s) is located on the second medical device, and in still others on both the first and second medical devices. In some embodiments, the first medical device is used to retrieve the second medical device from a body lumen.

The first and second medical devices, as well as any of the medical devices of the present disclosure (e.g., 20, 110, 210, 310, 410, 510, 610, 710, 810, 910, 1110, 1210, 1310, 1410, 1510, 1610, 1710, 1810, and 1910.), may be selected from such medical devices that include, but are not limited to drug coated (e.g., placitaxel and those pharmaceuticals and biologically active substances described herein in reference to blade-released pharmaceutical embodiments), aortic, wall, vascular (including without limitation covered stents such as PTFE (polytetrafluoroethylene)-covered stents), cerebral. nitinol, Palmaz-Schatz, Gianturco-Roubin, Wiktor, AVE Micro, Strecker, and Cordis stents. Medical devices may also be vena cava filters, aneurysm coils, coils, stent grafts, pacers, graphs, venous valves, septal defect devices, and guide wires. Medical devices may also be selected from the group consisting of catheters, vascular catheters, balloon catheters, guide wires, balloons, filters (e.g., vena cava filters), cerebral aneurysm filler coils (including without limitation GDC (Guglilmi detachable coils) and metal coils), vascular grafts, myocardial plugs, pacemakers, pacemaker leads, heart valves and intraluminal paving systems, filterwires, venous valves, bifurcation stents, aortic stents, Y-adapters, torque devices, indeflators, and in essence all devices that can be utilized in the vascular system. Medical devices may be balloon catheters including without limitation to over-the-wire, fixed-wire, rapid-exchange, perfusion balloon, ablation, and various specialty balloon catheters. Balloon material (and/or housing) may be selected from, but not limited to, compliant, minimally compliant and non-compliant materials. A medical device may also be, without limitation, an intravascular occlusion device, needle, hydrocephalus shunt, draintube, dialysis device, small or temporary joint replacement, urinary sphincter, urinary dilator, long term urinary device, penile prosthesis, vascular catheter port, peripherally insertable central venous catheter, long term tunneled central venous catheter, peripheral venous catheter, drug deposit, distal protection device, and short term central venous catheter.

Figure 21A:
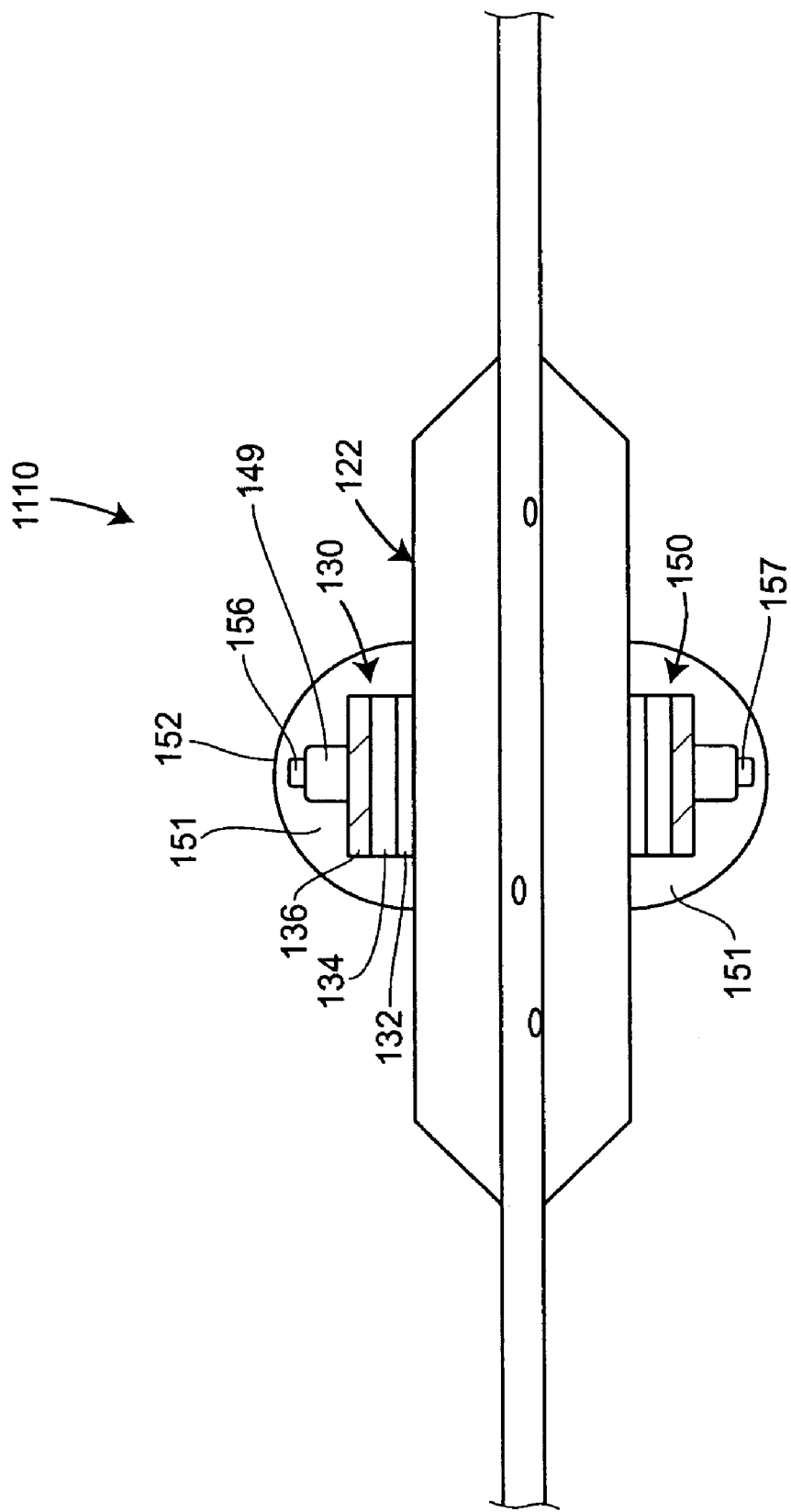
FIG. 21A is a partial longitudinal sectional view of a medical device comprising a nanoactuator and a blade, the nanoactuator in a non-activated state and operatively associated with an exterior surface, and the blade enveloped by a covering, according to the teachings of the disclosure.

FIG. 21A depicts a medical device 1110 that comprises a blade 156 operatively associated with a nanoactuator 130. The blade may be attached to the actuator by means 149, said means 149 may take a number of different forms including, but not limited to, a hard polymer (e.g., polyurethanes, polyamides, cyanoacrylates, and polyethylene oxide (PEO), Pebax, nylon, polyethyleneterephthalate (PET) and polybutyleneterephthalate (PBT)) and fiber (thread or flexible polymer string through a hole in one or more blades or on the edge or base of one or more blades). Other means of blade attachment include, without limitation, adhesives, rings, windings, hooks, rods, bolts, screws, brackets, and bands. In some embodiments employing bands, the band provided is elastic and provided around a circumference of the medical device holding one or more blades to the housing 112, balloon 120 or actuator 130 by means of a blade segment. Other means of blade attachment include, without limitation, adhesives, inject molding, mechanical locks. The blade 156 may comprise, but is not limited to, such materials as diamond and metal, e.g., steel. In some embodiments, the blade 156 may have a composite construction of a diamond cutting knife glued to a metal or polymer carrier in any size. In some embodiments, the blade 156 may comprise a series of axially placed single cutting blades connected (glued) to a single carrier. The blade 156 may be produced using micro-structuring techniques so that it has a width on the order of a human hair with blade tip radius on the order of 3 nm. Diamond blades may comprise a cutting edge of only a few atoms thick (e.g., as available from GFD Gesellschaft für Diamantprodukte mbH, Ulm, Germany). Small blades are advantageous for use on small balloons. Diamond blades are useful, because they do not dull as often as metal blades, and also will not appreciably affect MRI images. The blade 156 may be made in different shapes and sizes. The properties that the blade 156 may possess are not limited. The blade may have any degree of sharpness, and the sharpness may be selected in a particular embodiment to suit the intended use of the device. For example, a relatively sharp blade may be preferred when tissue is to be cut. Whereas in those embodiments involving drug delivery, a relatively dull blade may be used to puncture the surface 152. In some embodiments, the blade 156 may be supplemented or substituted for a needle, e.g., a coring needle for taking samples, a needle for injecting pharmaceuticals, or a suturing needle. In some embodiments, the blade 156 may comprise wire, stainless steel wire, polymer, hardened polymer, or alternating polymer or hardened polymer bumps. Any means or device that may puncture or score the surface 152 of the covering 151 may be used as the blade 156.

In FIG. 21A, the actuator 130 is a non-activated state and the blade 156 is enveloped in a covering 151, which may have a surface 152. In some embodiments, the covering 151 may comprise a soft polymer. Soft polymers may have a shore hardness of less than about 40D. Examples of soft polymers include, but are not limited to gels, polyurethane, Tecothane®, low durometer Pebax, silicone and SIBS. In some embodiments, the covering 151 may comprise a fabric, including without limitation, polytetrafluoroethylene (PTFE), Teflon and Teflon-like polymer fabrics, and Gortex. The covering may also comprise those materials discussed for the outer sheaths 34 and 145. In some embodiments, there is not a covering 151. In some embodiments, the covering 151 may comprise a combination of different materials. In some embodiments, the covering 151 is not operatively associated with one or more blades, or is not associated at all with the medical device 1110.

In some embodiments, the covering 151 may comprise a pharmaceutical, biologically active substance or other compound such that when the blade 156 emerges from the covering, the pharmaceutical is released. Such embodiments may further comprise a pharmaceutically acceptable diluent, adjuvant, excipient, carrier, or mixture thereof. Examples of pharmaceuticals and biologically active substances that may be used in conjunction with the present disclosure include, without limitation, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. For example, biologically active solutes include anti-thrombogenic agents such as heparin, heparin derivatives, urokinase, and PPACK (dextrophenylalanine proline arginine chloromethylketone); prostaglandins, prostacyclins/prostacyclin analogs; antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetylsalicylic acid, and mesalamine, lipoxygenase inhibitors; calcium entry blockers such as verapamil, diltiazem and nifedipine; antineoplastic/ antiproliferative/antimitotic agents such as paclitaxel, 5-fluorouracil, methotrexate, doxorubicin, daunorubicin, cyclosporine, cisplatin, vinblastine, vincristine, colchicine, epothilones, endostatin, angiostatin, squalamine, and thymidine kinase inhibitors; L-arginine; antimicrobials such as triclosan, cephalosporins, aminoglycosides, and nitrofurantion; anesthetic agents such as lidocaine, bupivacaine, and ropivacaine; nitric oxide (NO) donors such as linsidomine, molsidomine, NO-protein adducts, NO-polysaccharide adducts, polymeric or oligomeric NO adducts or chemical complexes; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; interleukins, interferons, and free radical scavengers; vascular cell growth promoters such as growth factors, growth factor receptor antagonists, transcriptional activators, and translational promotors; vascular cell growth inhibitors such as growth factor inhibitors (e.g., PDGF inhibitor—Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; Tyrosine kinase inhibitors, chymase inhibitors, e.g., Tranilast, ACE inhibitors, e.g., Enalapril, MMP inhibitors, (e.g., Ilomastat, Metastat), GP IIb/IIIa inhibitors (e.g., Intergrilin, abciximab), seratonin antagonist, and 5-HT uptake inhibitors; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof, and beta blockers. Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules.

Figure 21C:
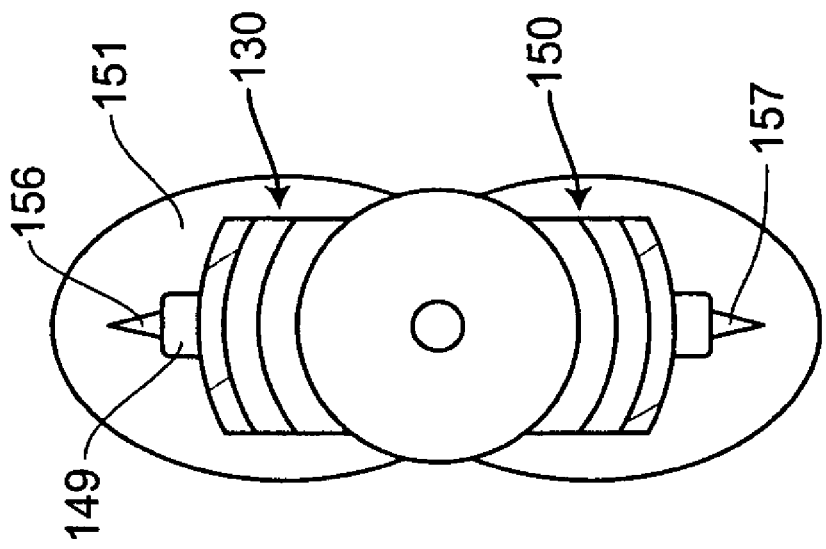
FIG. 21C is a section view of the medical device shown in FIG. 21A showing an embodiment wherein there are two nanoactuators positioned on opposing sides of the medical device, according to the teachings of the disclosure.
Figure 21B:
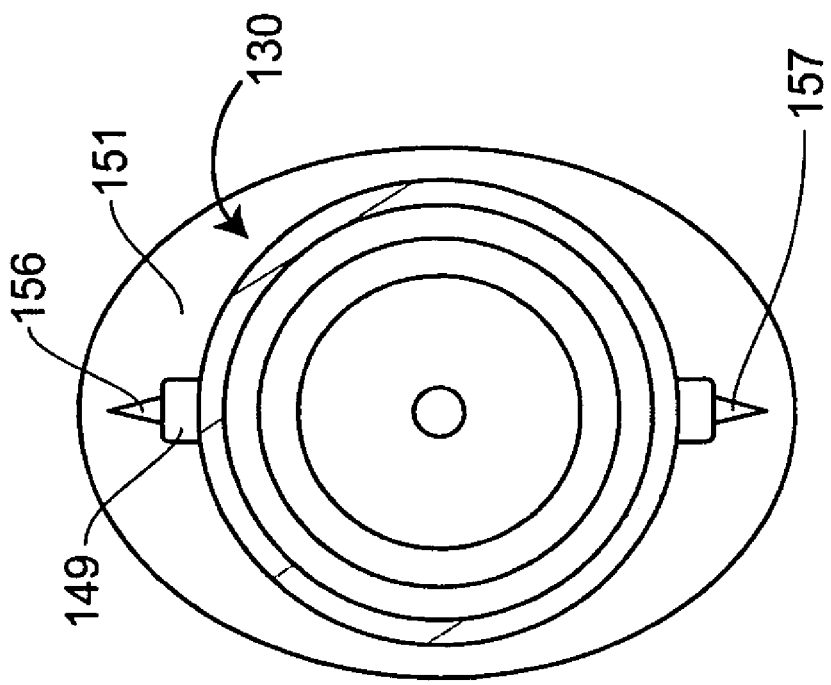
FIG. 21B is a sectional view of the medical device shown in FIG. 21A showing an embodiment wherein the nanoactuator encircles the medical device, according to the teachings of the disclosure.
Figure 21D:
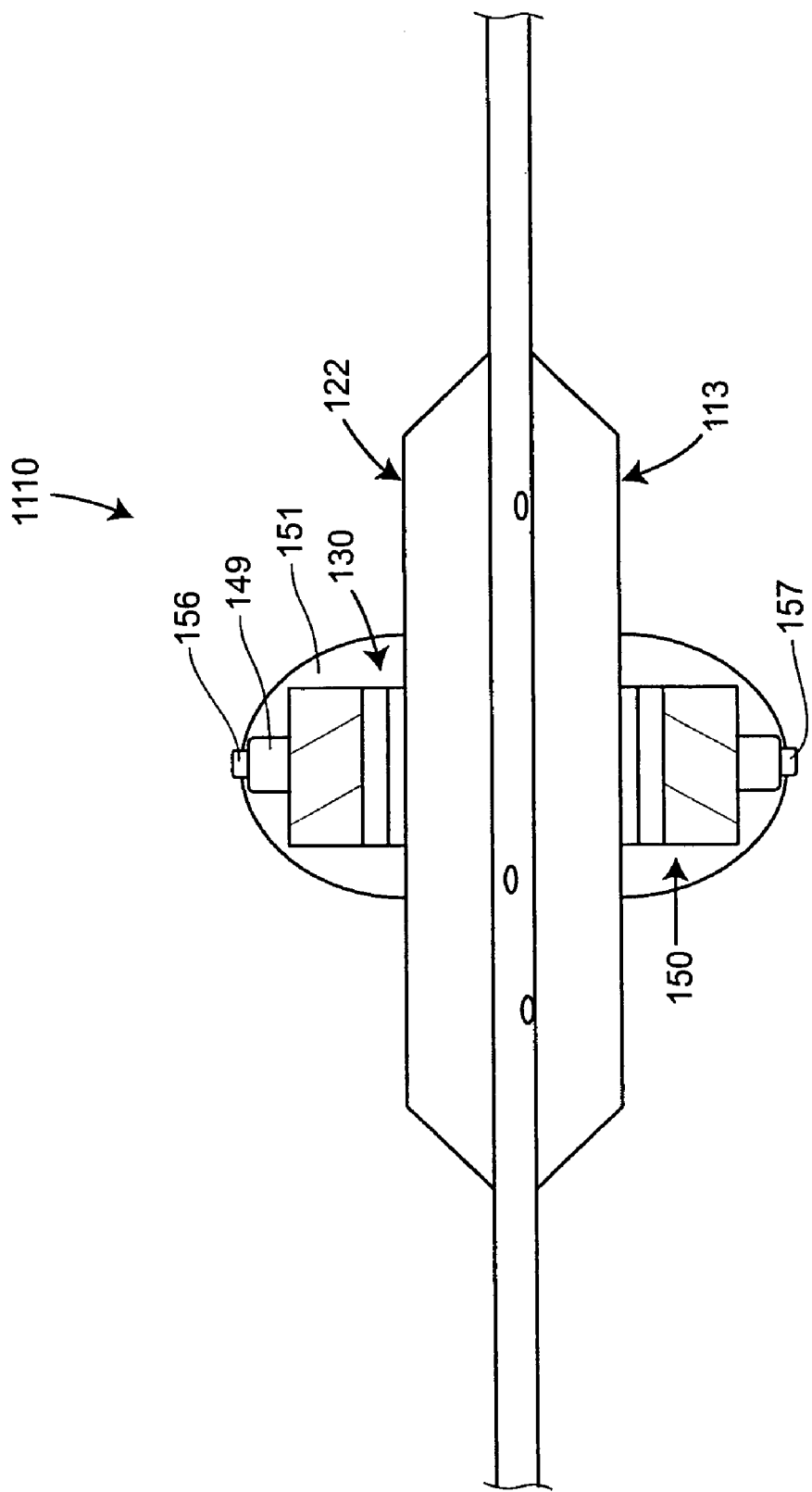
FIG. 21D shows the medical device in FIG. 21A, but with the nanoactuator in an activated state and blade emerged from the covering.
Figure 21F:
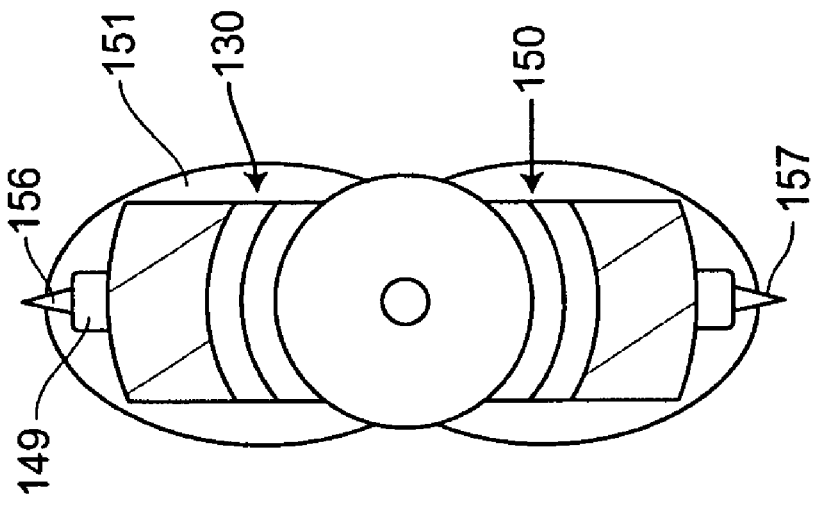
FIG. 21F is a section view of the medical device shown in FIG. 21D showing an embodiment wherein there are two nanoactuators positioned on opposing sides of the medical device, according to the teachings of the disclosure.

Two blades 156, 157 are shown in FIGS. 21A-F, but that is for illustrative purposes only, as the medical device 1110 may have any number of different blades. The blades, e.g., 156, 157, may be attached to the same actuator 130 or attached to multiple actuators, e.g., 130 and 150. For example, the blades may be arranged linearly in some embodiments. In some embodiments, a linear arrangement is achieved by using overlapping blades. In some embodiments, the blades are arranged about a perimeter, e.g., 113, of the medical device, e.g., 1110, 1210, at various angles, including, but not limited to, 15, 30, 45, 60, 90, 120 and 180 degrees. In some embodiments, the medical device has three blades spaced 120° apart about a perimeter. FIGS. 21B and 21C show lateral sections of the medical device 1110 analogous to FIGS. 12B and 12C. FIGS. 21C and 21F provide examples of an embodiment wherein the blades 156, 157 are arranged at 180 degrees from one another.

Figure 21E:
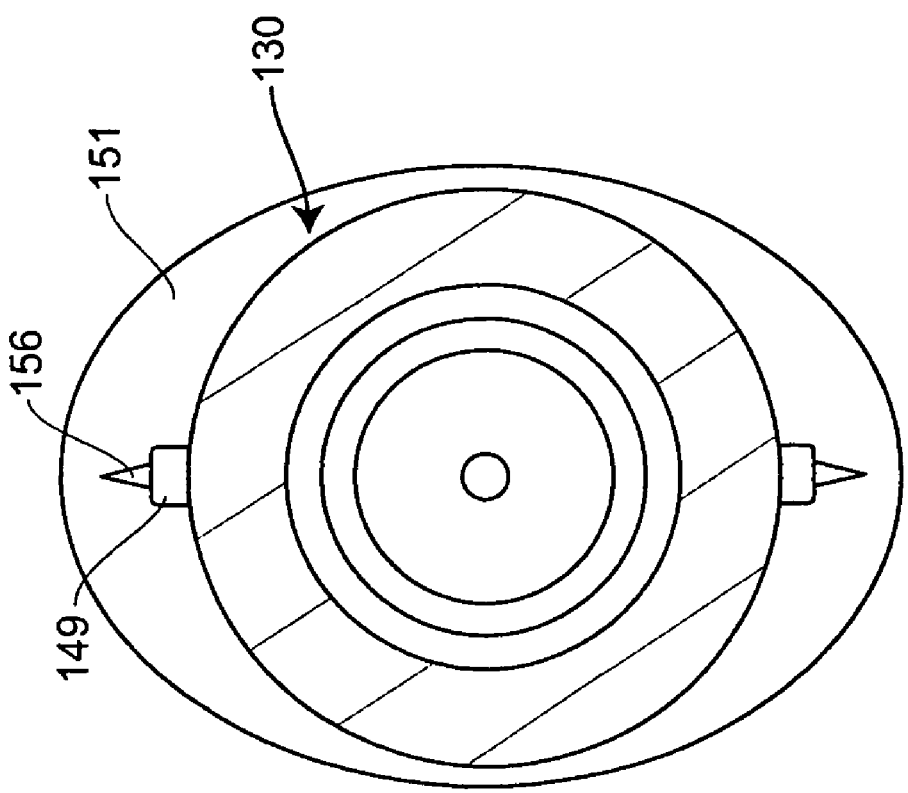
FIG. 21E is a sectional view of the medical device shown in FIG. 21D showing an embodiment wherein the nanoactuator encircles the medical device, according to the teachings of the disclosure.

FIGS. 21D-F show the medical device 1110 with the actuator 130 in an activated state. With the actuator in the activated state, the blade 156 emerges from covering 151 so that the blade is exposed and can be used for cutting purposes. The covering 151 on medical devices, e.g., 1110, 1210 may cover all or part of the exterior surface 122 of the housing 112 or balloon 120. The extent, including, but not limited to depth, width, volume and area, of the covering's coverage as shown in FIGS. 21 and 22 is for illustrative purposes only.

Figures 22C, 22D:
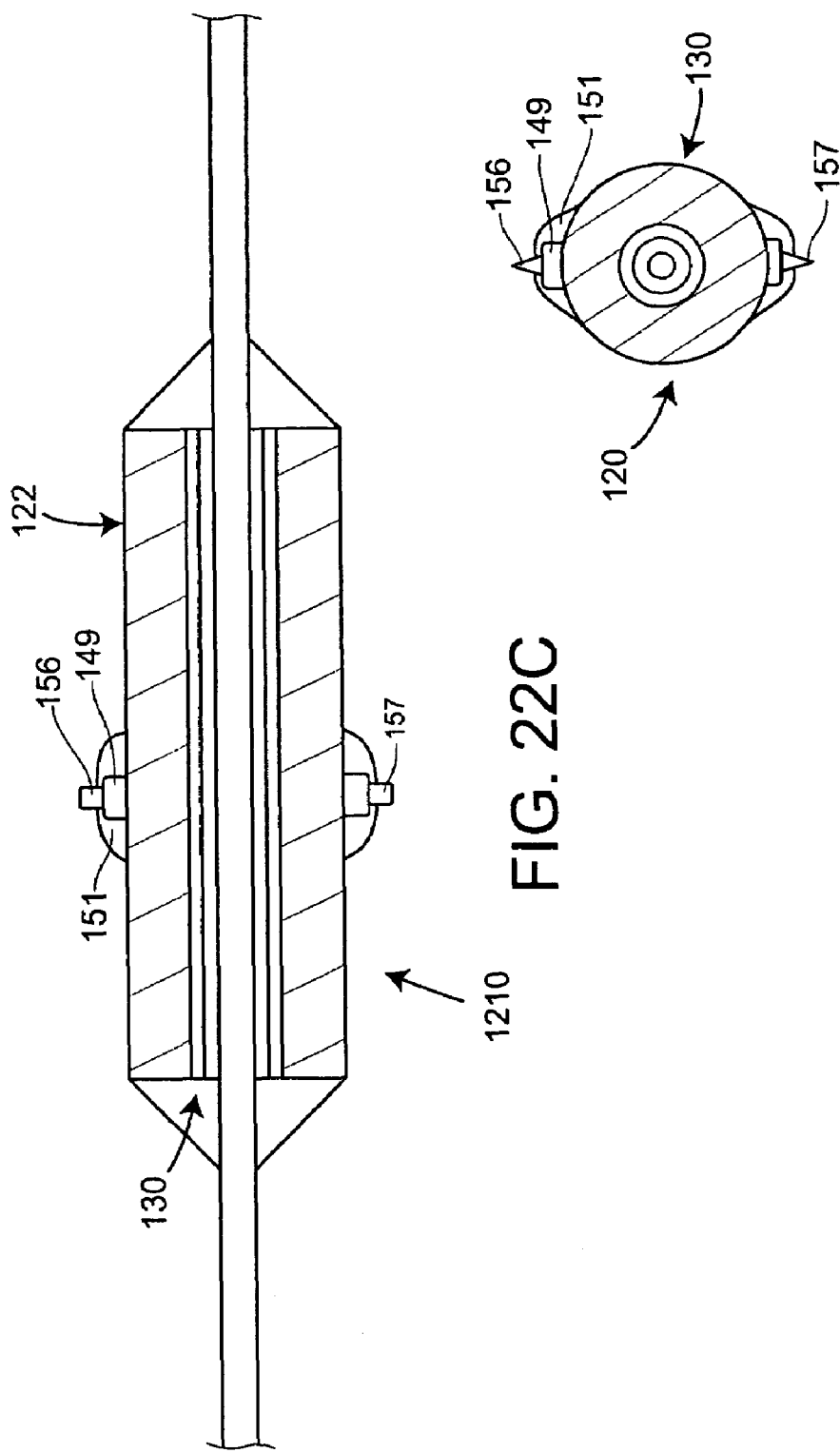
FIG. 22C shows the medical device in FIG. 22A, but with the nanoactuator in an activated state and blade emerged from the covering.
FIG. 22D is a sectional view of the medical device shown in FIG. 22C showing an embodiment wherein the nanoactuator encircles the medical device, according to the teachings of the disclosure.

FIGS. 22A-D show a medical device 1210, which is a variation on medical device 1110. Unlike the medical device 1110, wherein the actuator is attached to an exterior surface 122 of the housing 112 (e.g., balloon 120), the actuator 130 of the medical device 1210 is located in an interior 124 of the housing 112 (e.g., balloon 120). While an embodiment of medical device 1210 analogous to medical device 1110 shown in FIG. 21C, such embodiments are also possible for the medical device 1210. FIGS. 22C and 22D show the medical device 1210 with the actuator 130 in an activated state such that the balloon 120 has expanded and blade 156 has emerged from the covering 151, and the blade can be used for cutting purposes.

One will also appreciate from this disclosure that such blade arrangements with the blade 156 enveloped in a covering 151 with the balloon 120 deflated and with the blade 156 at least partially exposed with the balloon 120 inflated can be achieved without an actuator 130, i.e., using just a classical balloon catheter. In embodiments where the balloon 120 is expanded so that the blade 156 emerges from the covering 151, sufficient pressure may be exerted so that the surface tension allows the blade 156 is pushed at least partially out of the covering 151. In some embodiments, the medical devices 1110 and 1210 lack a balloon 120 in an arrangement analogous to that shown for device 510 shown in FIGS. 16A and 16B. The blade 156 may be attached to the housing 122, or the inner tube 126. In some embodiments the blade(s) 156 and actuator(s) 130 are operatively associated with a guide wire 153. In some embodiments, the medical devices 1110 and 1210 have actuators, e.g., 130, both in an interior 124 and operatively associated with a exterior surface 122. In some embodiments the blade 156 may comprise a pivot or hinge 165 such as that described herein in respect to medical device 165.

Figure 23:
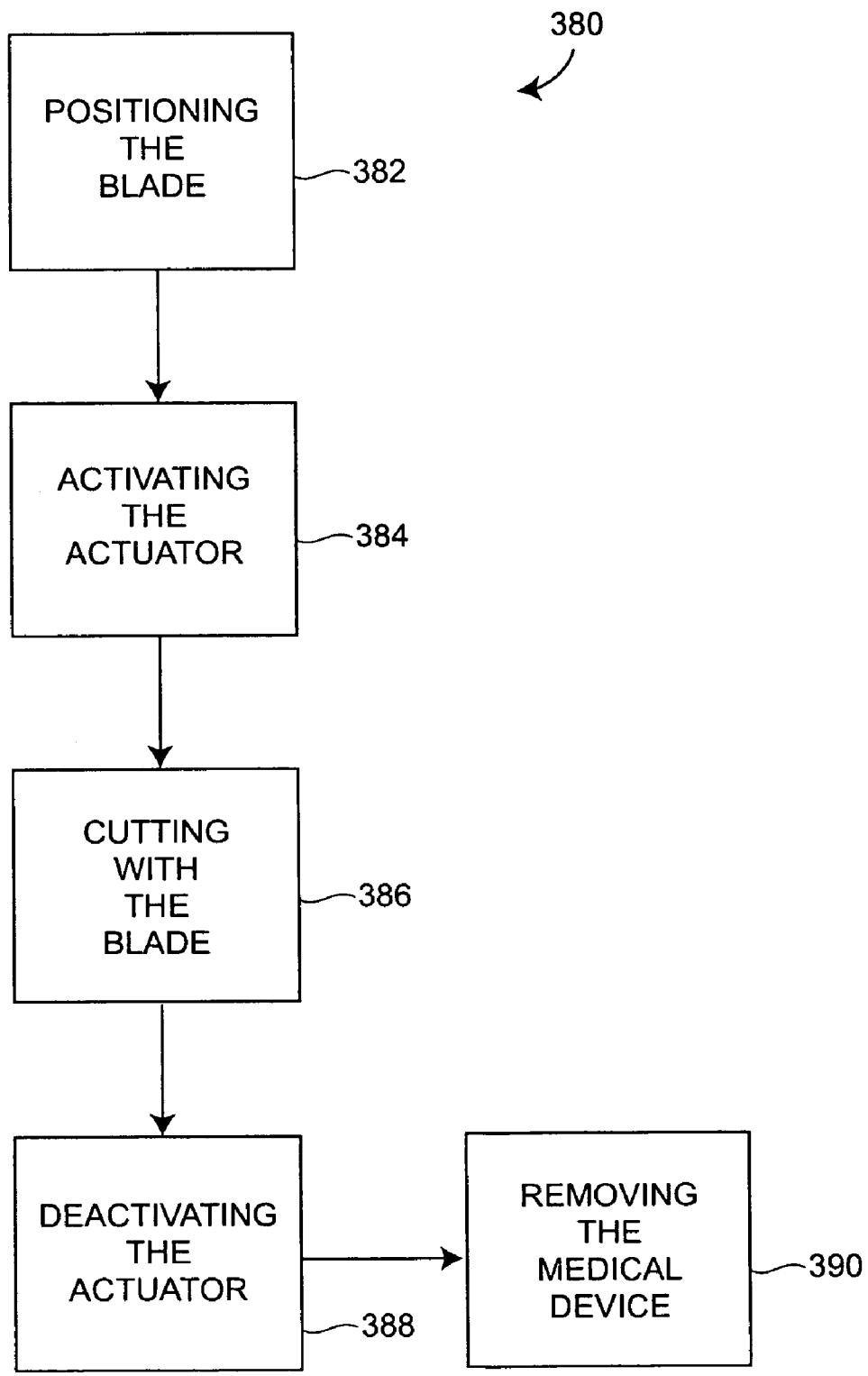
FIG. 23 is a flow chart showing a method of cutting with a blade, according to the teachings of the disclosure.

FIG. 23 depicts a flow chart of a method 380 of employing a medical device with a blade, e.g., 1110, 1210. The method 380 may comprise the step 382 of positioning the blade in an area to be cut, a step 384 of activating the actuator so that at least a portion of the blade emerges from the covering, a step 386 of cutting with the blade, and a step 388 of deactivating the actuator so that the blade is again enveloped by the covering. In some embodiments, the method 380 is practiced so that the blade(s) is positioned in a stenosis in order to cut the same. In some embodiments, the method 380 is repeated so as to remove all or part of a stenosis. The cutting step 386 may comprise rotating the medical device about an axis 111. In some embodiments, the blade(s) 156 is used to attach a medical device to the lining of a body lumen. In some embodiments, the method 380 further comprises the step 390 of removing the medical device. In some embodiments, the covering 151 comprises a pharmaceutical such that when the actuator is activated the blade 156 may pierce the surface 152 of the covering 151 resulting in the release of the pharmaceutical from the covering 151.

Figure 24A:
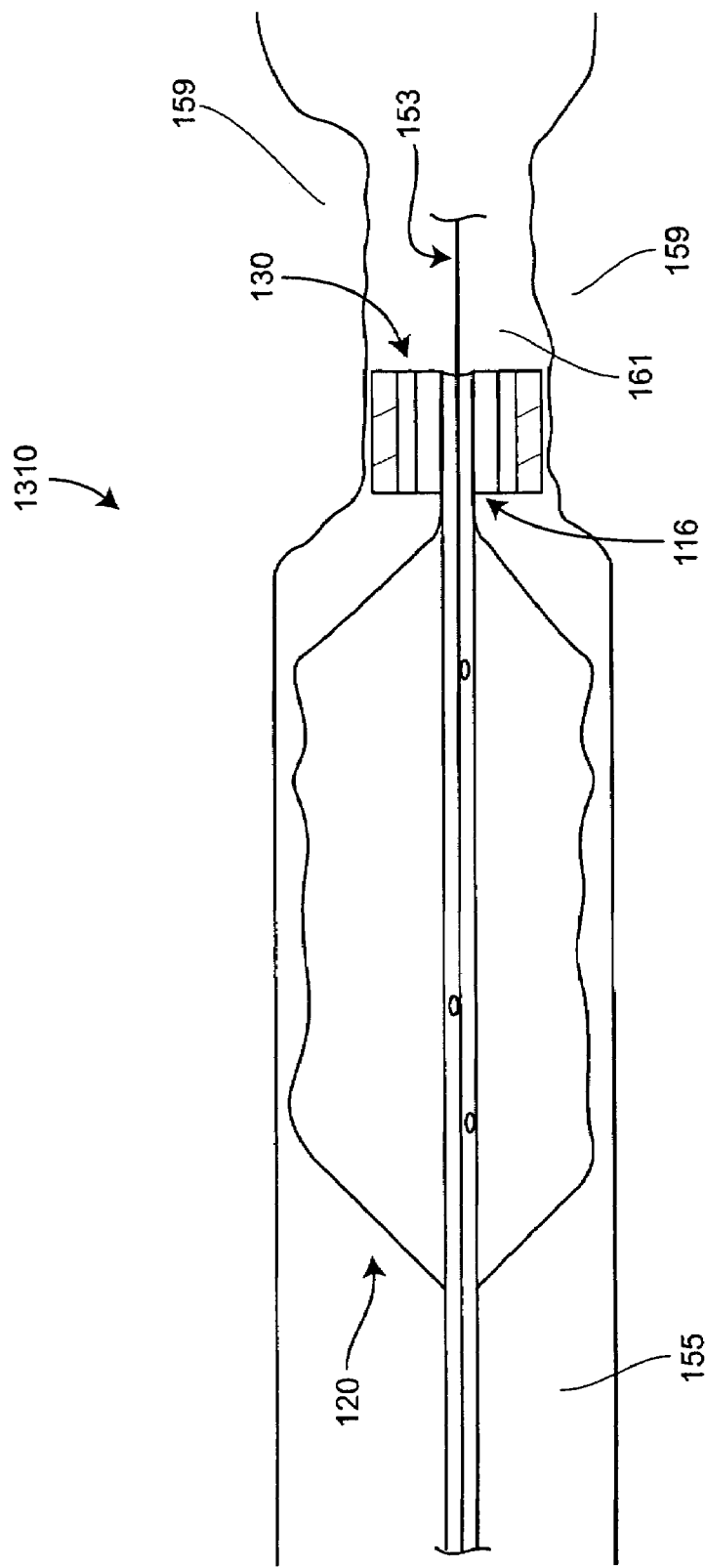
FIG. 24A is a partial longitudinal sectional view of a balloon catheter with a nanoactuator at its distal end, the distal end inserted into a stenosis, the actuator in a non-activated state, according to the teachings of the disclosure.
Figure 24B:
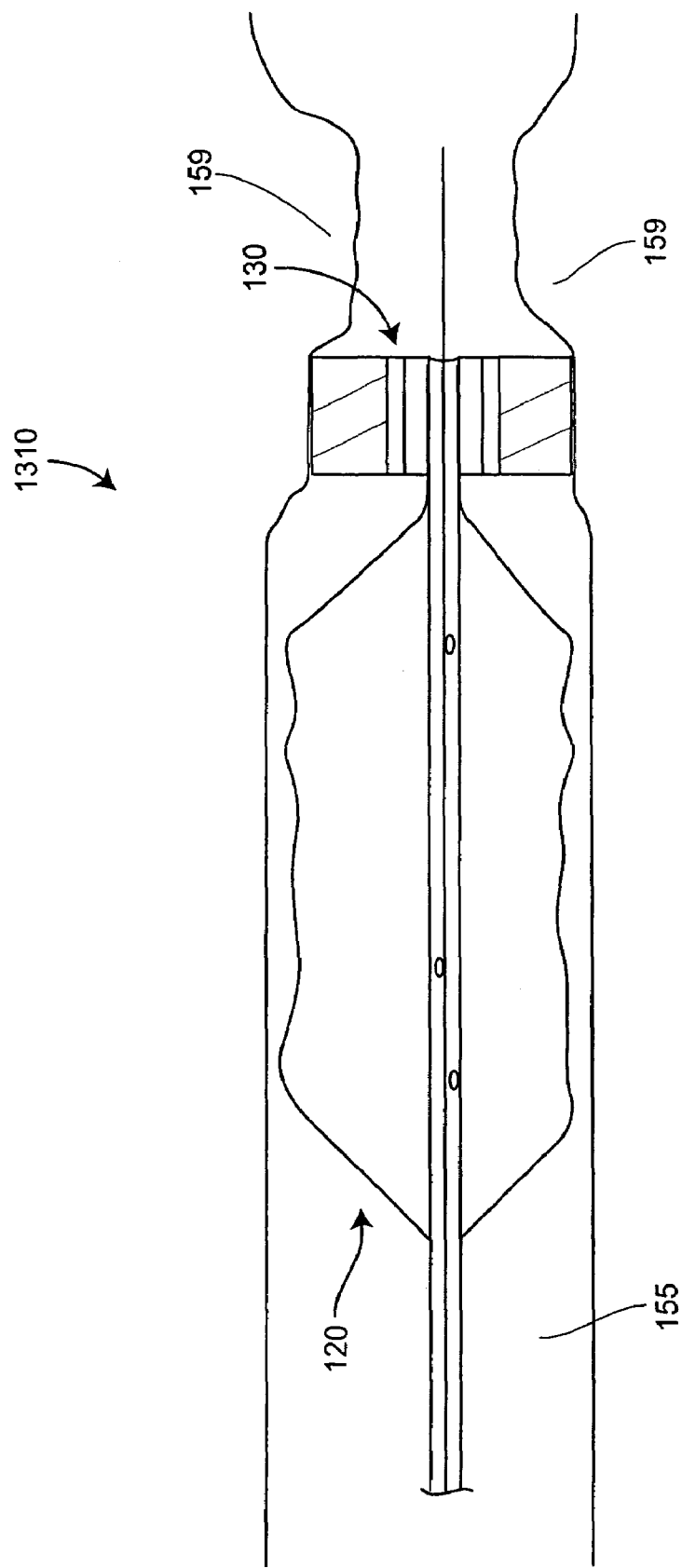
FIG. 24B shows the balloon catheter in FIG. 24B, but with the actuator in an activated state, according to the teachings of the disclosure.
Figure 24C:
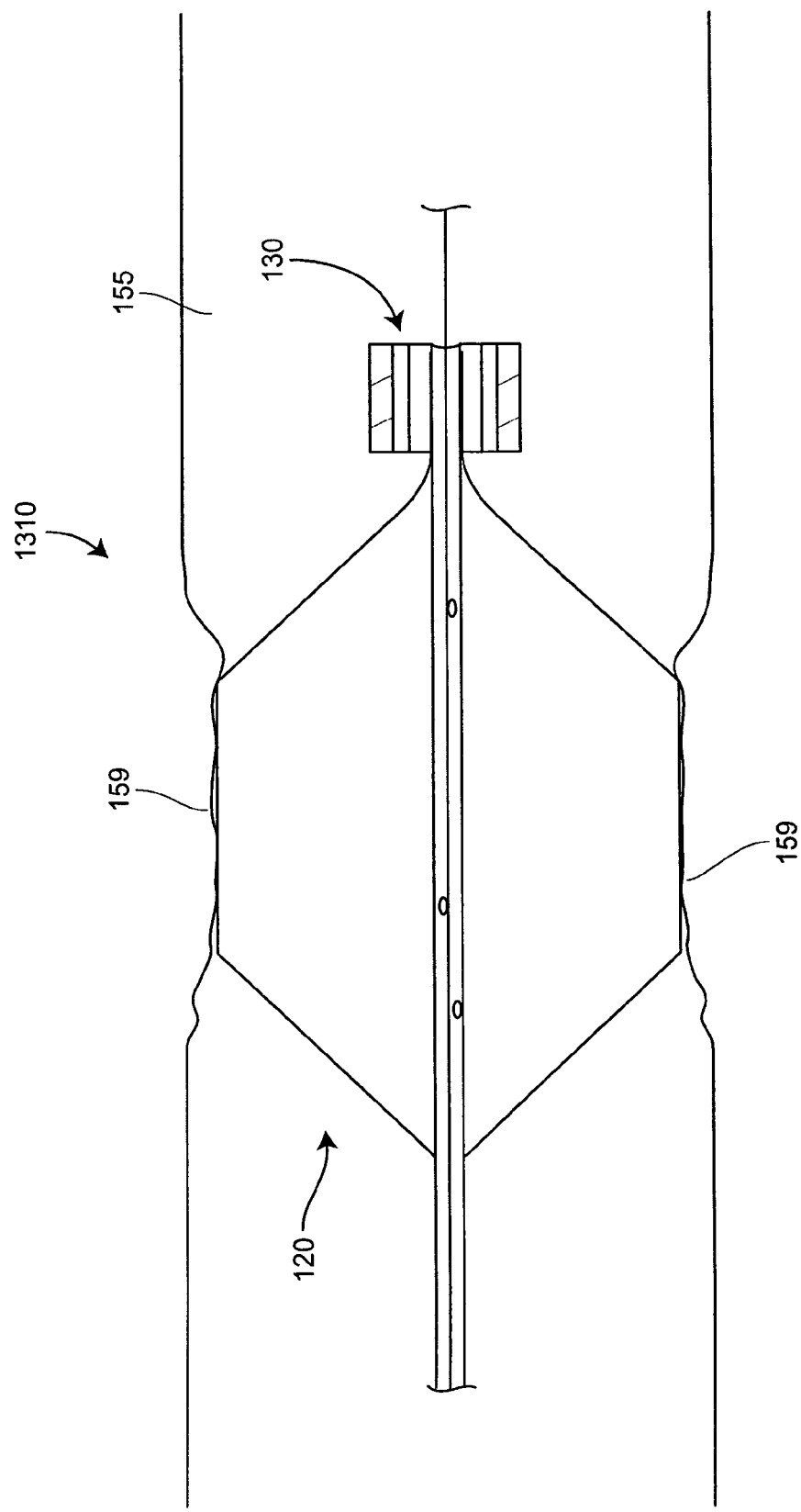
FIG. 24C shows the balloon catheter of FIG. 24A with balloon inserted and inflated in the stenosis, according to the teachings of the disclosure.
Figure 25:
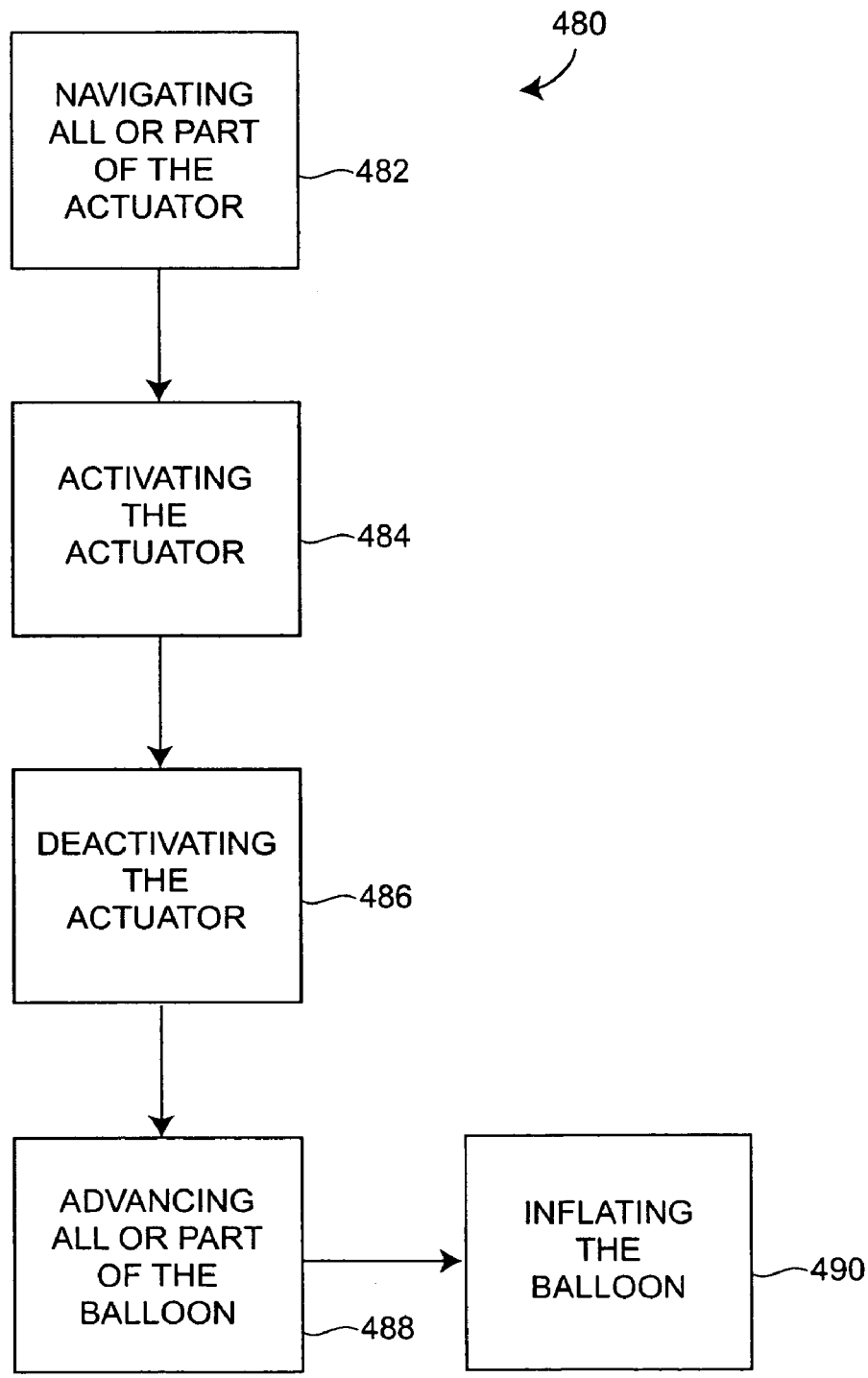
FIG. 25 is a flow chart showing a method of advancing a balloon catheter through a stenosis, according to the teachings of the disclosure.

FIGS. 24A-C depict a medical device or system, e.g., a balloon catheter, 1310 located in a body lumen 155 comprising a stenosis 159. The medical device 1310 may comprise a balloon 120 and at least one actuator 130. The medical device 1310 may further comprise a guide wire 153. The actuator 130 may be associated with a distal end 116 of the balloon 120 or with guide wire 153 on a part of the guide wire adjacent to the distal end 116 of the balloon 120. In some embodiments, wherein the actuator 130 is associated with the guide wire 153, the guide wire may serve as the first electrode 132. Guide wires 153 may comprise, but are not limited to, platinum and nitinol. FIG. 25 depicts a flow chart of a method 480 of advancing a balloon catheter, e.g., system or medical device 1310, through a stenosis 159 in a body lumen 155. Such a method 480 can be used to open up a stenosis 159, stenoses may or may not be calcified. The method 480 may comprise a step 482 of navigating all or part of the actuator into a stenosis, a step 484 of activating the actuator, the expansion thereof causing the stenosis to open at least partially, a step 486 of deactivating the actuator, and a step 488 of advancing all or part of the balloon into the stenosis. In some embodiments, a series of actuators 130 may be provided at the distal end 116 of the balloon 120, each successively distal actuator 130 may have a smaller diameter to allow for easier insertion into the stenosis 159. In some embodiments, the actuator 130 has a helical, cone or screw-like shape with the tip of the helix, cone or screw being distal to the balloon and pointing toward or into the stenosis 159, again allowing for easier insertion into the stenosis 159.

FIG. 24A depicts the medical device 1310 as it may appear after the navigating step 482 and before the activating step 484. FIG. 24B shows the medical device 1310 as it may appear after the activating step 484 and before the deactivating step 486. The method 480 may be repeated by activating the actuator again, deactivating the actuator, and further advancing the balloon into the stenosis. In some embodiments, the method 480 further comprises the step 490 of inflating the balloon. FIG. 24C shows how the medical device 1310 may appear after the step 490 has been performed. One will understand, as with the other methods of the disclosure, that the order and performance of the steps of method 480 may be varied on a case-by-case basis. For example, one may begin the advancing step 488 just before or simultaneously with the deactivating step 486 so that the balloon can be pulled further into the stenosis before the stenosis closes again. One may perform the method 480 so that the balloon is inflated after the balloon has advanced so that it is enclosed within an interior of the stenosis 161, e.g., as in FIG. 24C, or so that at least the distal end of the balloon has advanced through and of the of the stenosis.

In some embodiments, in contrast to what is shown in FIGS. 24A-C, in some embodiments, an actuator 130 may be provided on a proximal 114 end of a balloon. Such a device is useful in narrowing lumens, e.g., a large vessel that branches into a vessel which has a smaller diameter.

Figure 26A:
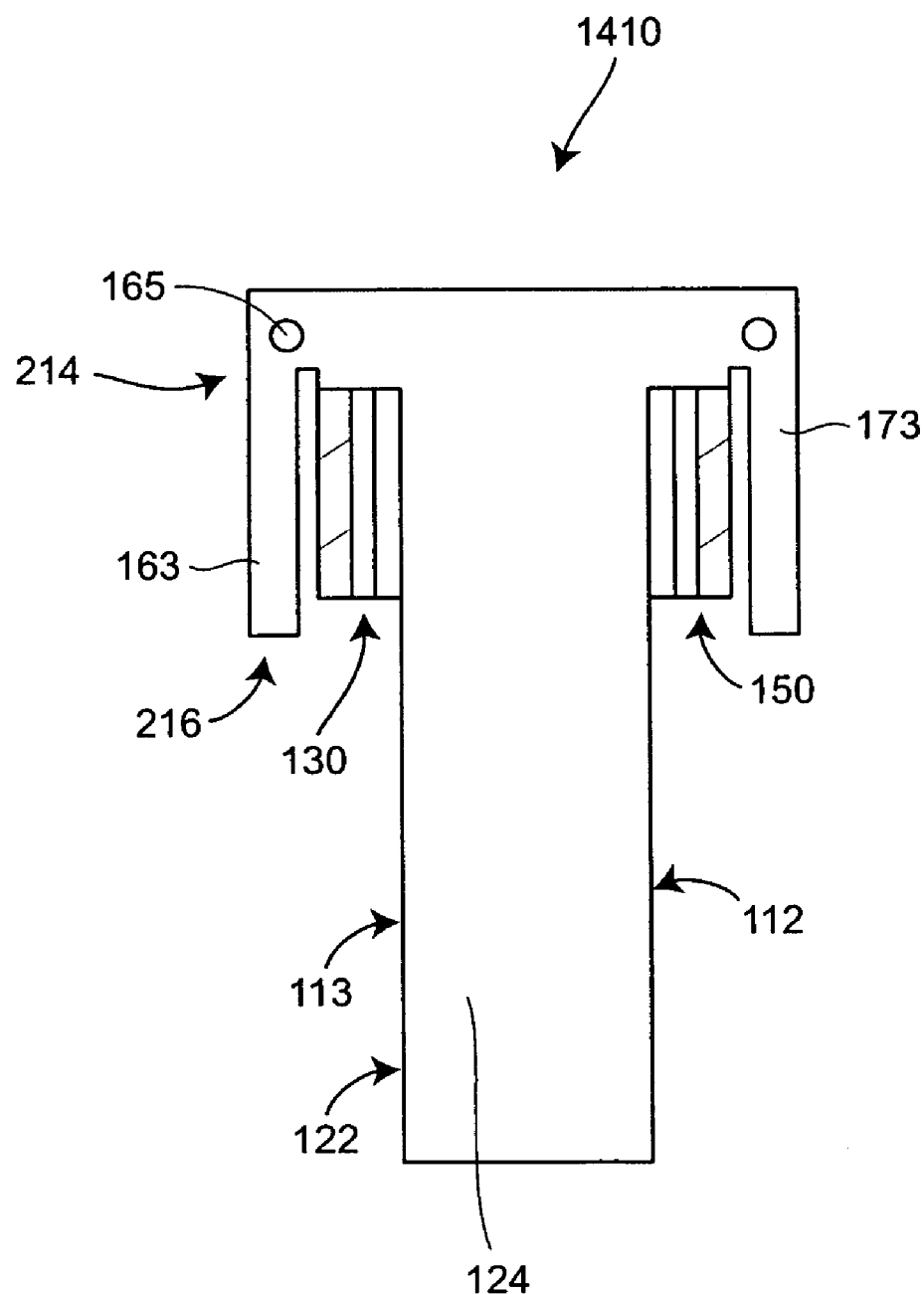
FIG. 26A is a longitudinal sectional view of a medical device with a hook operatively associated with a nanoactuator, the nanoactuator in a non-activated state, according to the teachings of the disclosure.
Figure 26B:
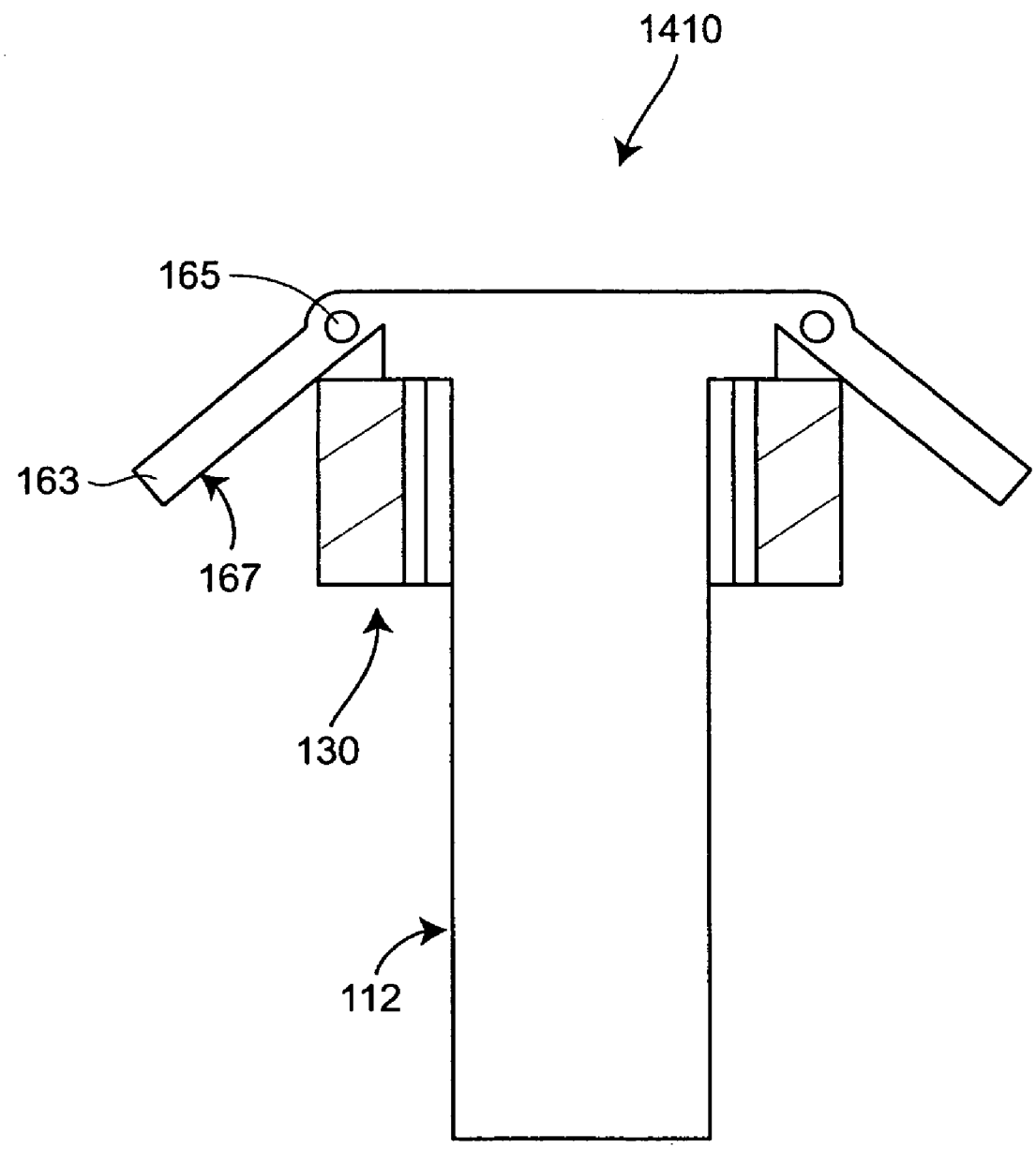
FIG. 26B shows the medical device of FIG. 26A, but with the actuator in an activated state with the hooks extended, according to the teachings of the disclosure.

FIG. 26A depicts a medical device 1410 that may comprise at least one nanoactuator 130 and a hook 163, having a proximal end 214 and distal end 216, that may be pivotally associated at its proximal end 214 with the housing 112 at a pivot or hinge 165. In some embodiments, the medical device 1410 may have a single hook 163, in other it may have a plurality hooks, e.g., including a second hook 173. A single actuator 130 or multiple actuators, e.g., 130, 150, etc., may be used in a manner analogous to that described herein in relation to medical device 110. FIG. 26B shows the medical device 1410 after the nanoactuator has been activated, resulting in the hook extending so that the distal end 216 is further disposed from the housing 112. In some embodiments, the hook 163 may comprise a blade 156.

Figure 27A:
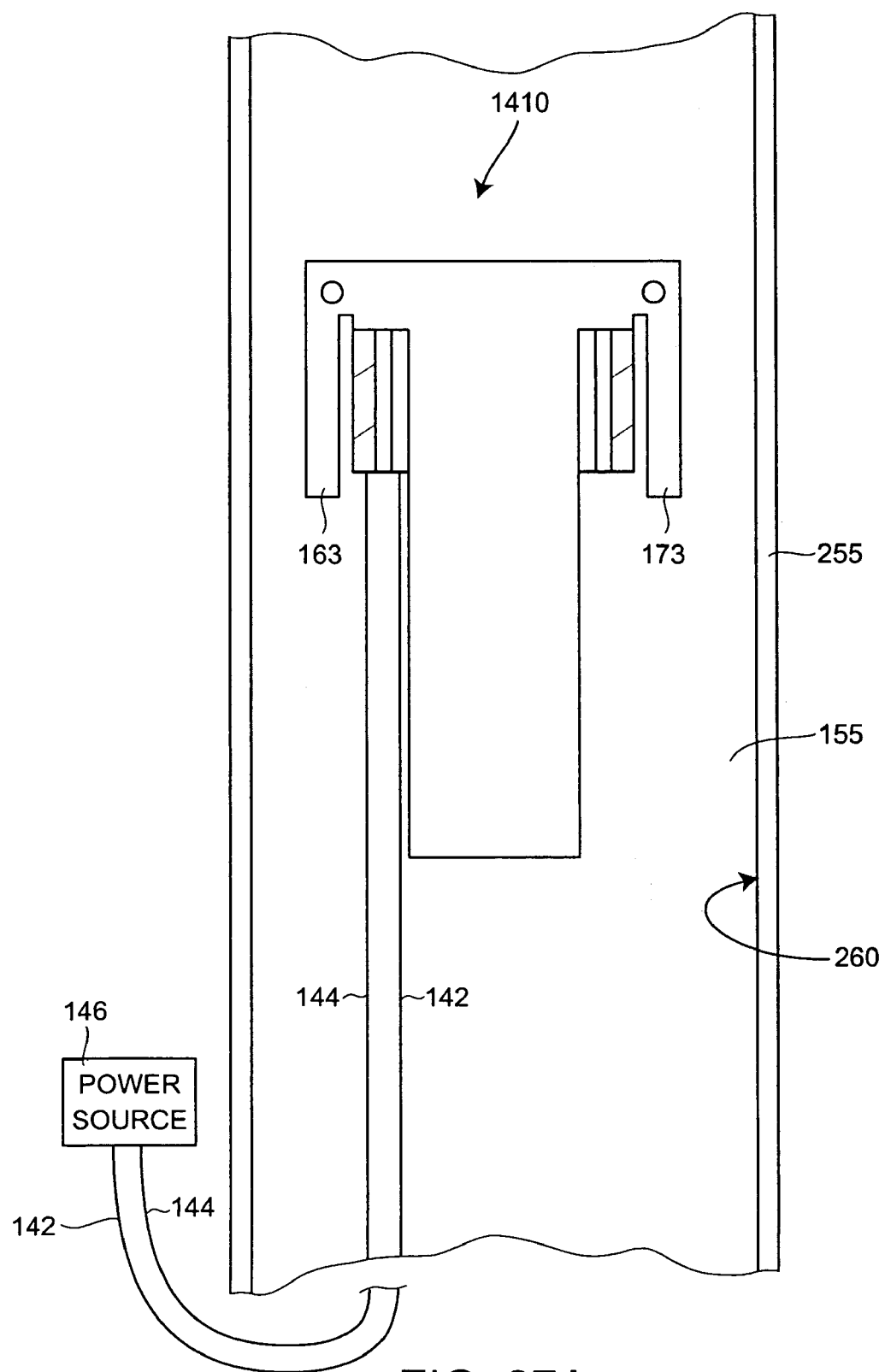
FIG. 27A. shows the medical device of FIG. 26A, positioned within a body lumen, according to the teachings of the disclosure.
Figure 27B:
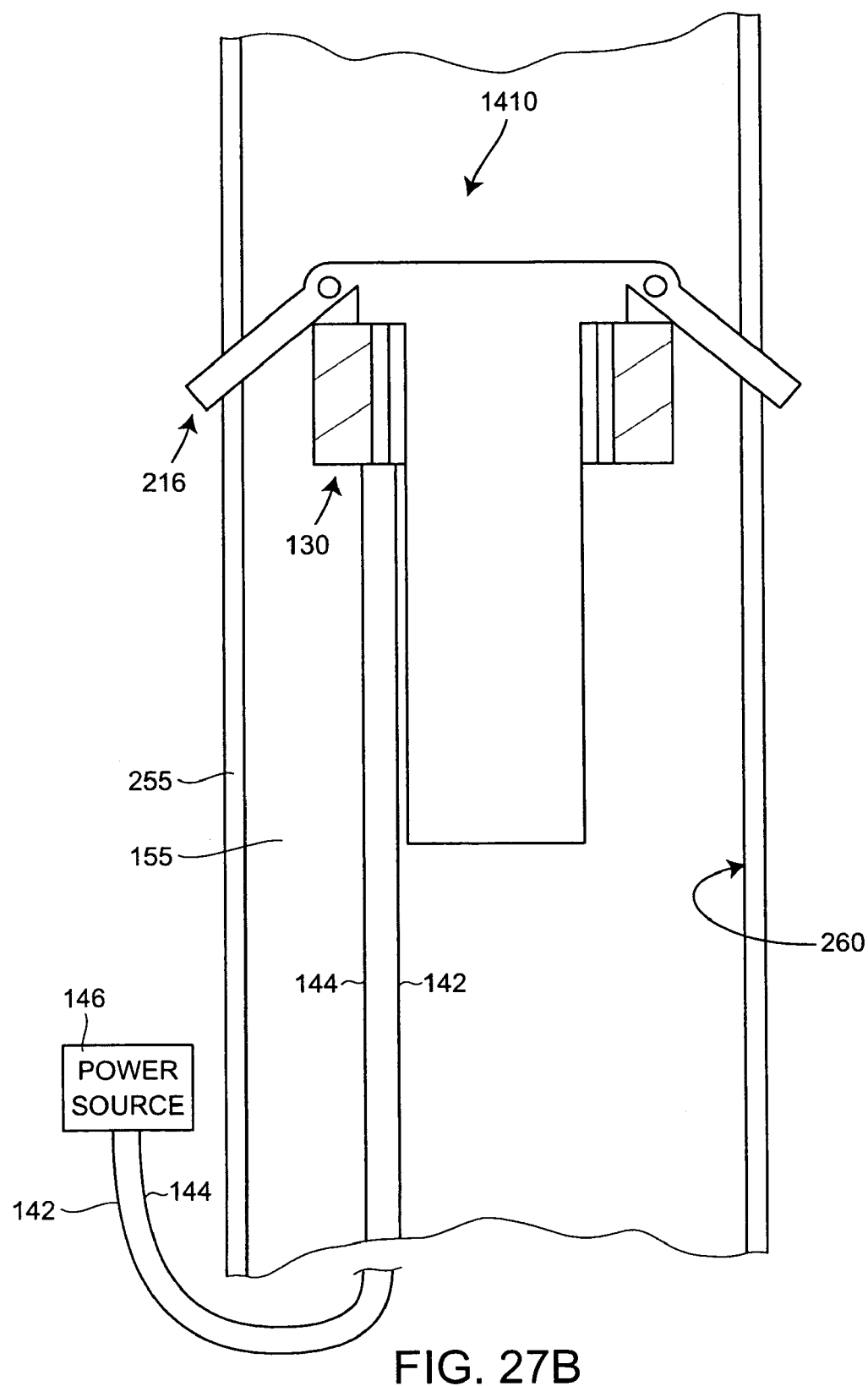
FIG. 27B shows the medical device of FIG. 27B, but with the actuator in an activated state and the hooks embedded in a lining of the body lumen, according to the teachings of the disclosure.

FIGS. 27A and 27B depict the medical device 1410 positioned in a body lumen 155 with a lumen wall 255. In FIG. 27B, the medical device is shown as it had been in FIG. 26B, but with the presence of the lumen wall 255, the medical device 1410 has become attached to the lumen wall 255. While the hooks, e.g., 163, 173, are shown puncturing the lumen wall, that is for illustrative purposes only. In other embodiments, the hooks may push against the lumen lining 260 so as to secure the medical device 1410. The body lumen 155 may include, but is not limited to, arteries, veins, capillaries, the heart, the aorta, the respiratory tract, the alimentary canal, and the bladder and urinary tract.

Figure 28:
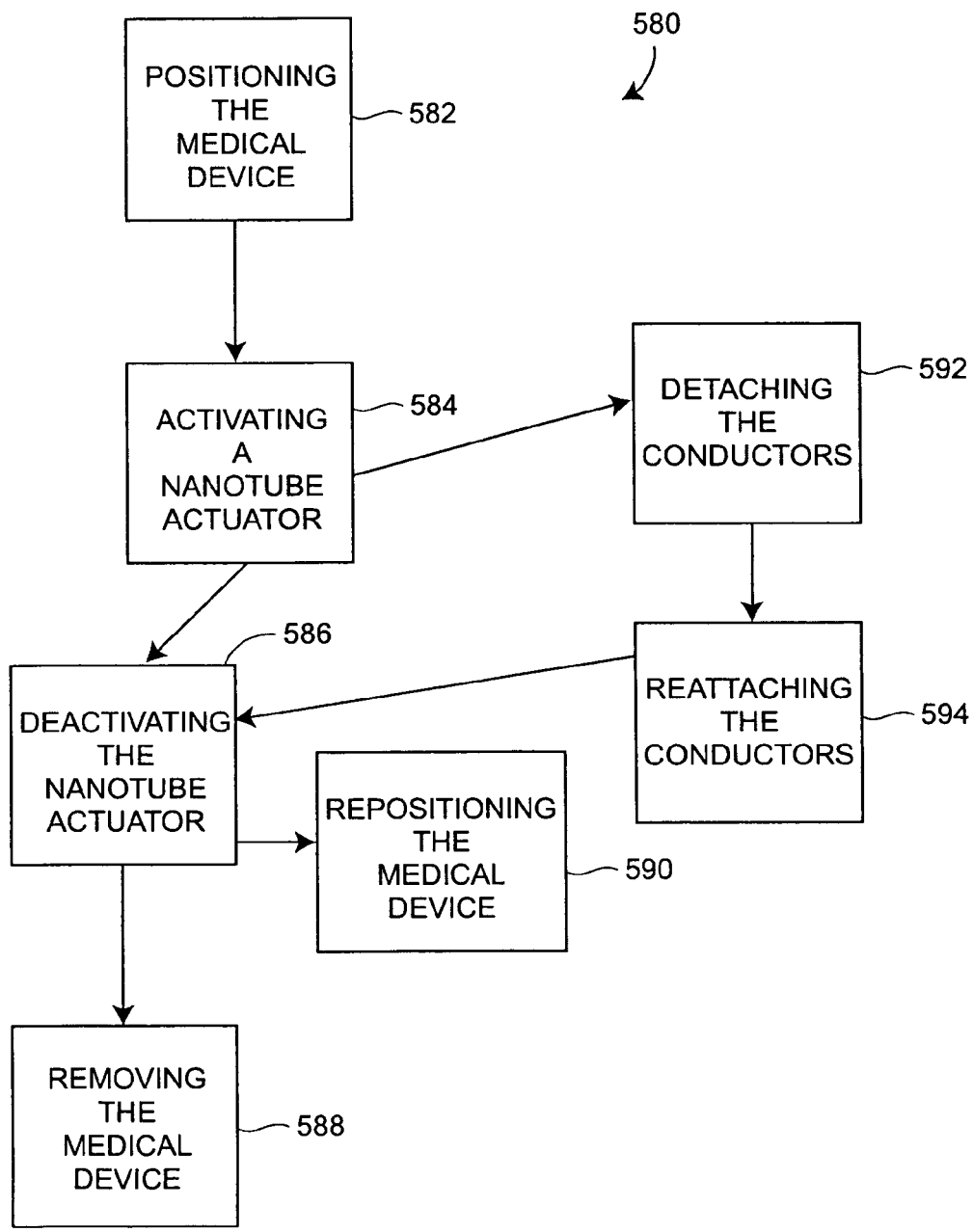
FIG. 28 is a flow chart showing a method of attaching a medical device to a lining of a body lumen, according to the teachings of the disclosure.

FIG. 28 depicts a flow chart showing a method 580 of attaching a medical device, e.g., 1410, to a lining of body lumen. The method 580 may comprise a step 582 of positioning the medical device at a desired position for attachment, and a step 584 of activating a nanoactuator operatively associated with a housing of the medical device and a hook of the medical device. In some embodiments, the method 580 may further comprise a step 586 of deactivating the nanoactuator, and in some embodiments may further comprise a step 588 of removing, or a step 590 of repositioning the medical device. In some embodiments, the method 580 further comprises, e.g., after activating the actuator, a step 592 of detaching the conductors from the actuator, the conductors having supplied the power to activate the actuator. In some embodiments, the method 580 further comprises a step 594 of reattaching the conductors to the actuator, which may be further proceeded by the deactivating step 586 and either the removing 588 step or repositioning step 590. In some embodiments, both conductors are detached, in others only one.

Figure 29A:
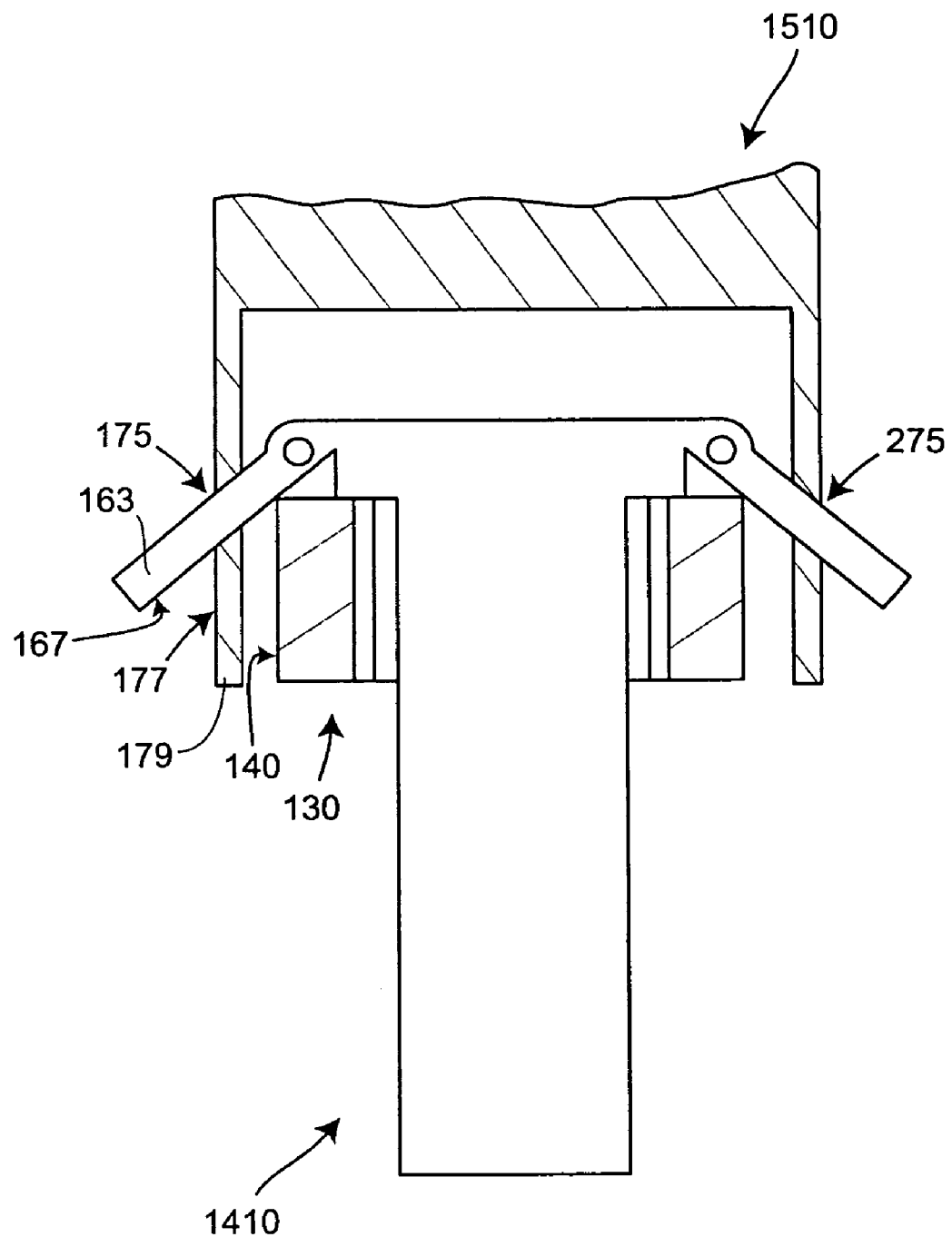
FIG. 29A shows the medical device of FIG. 27A so that the actuator(s) are activated and the hooks are positioned in receptacles of a second medical device, according to the teachings of the disclosure.
Figure 29B:
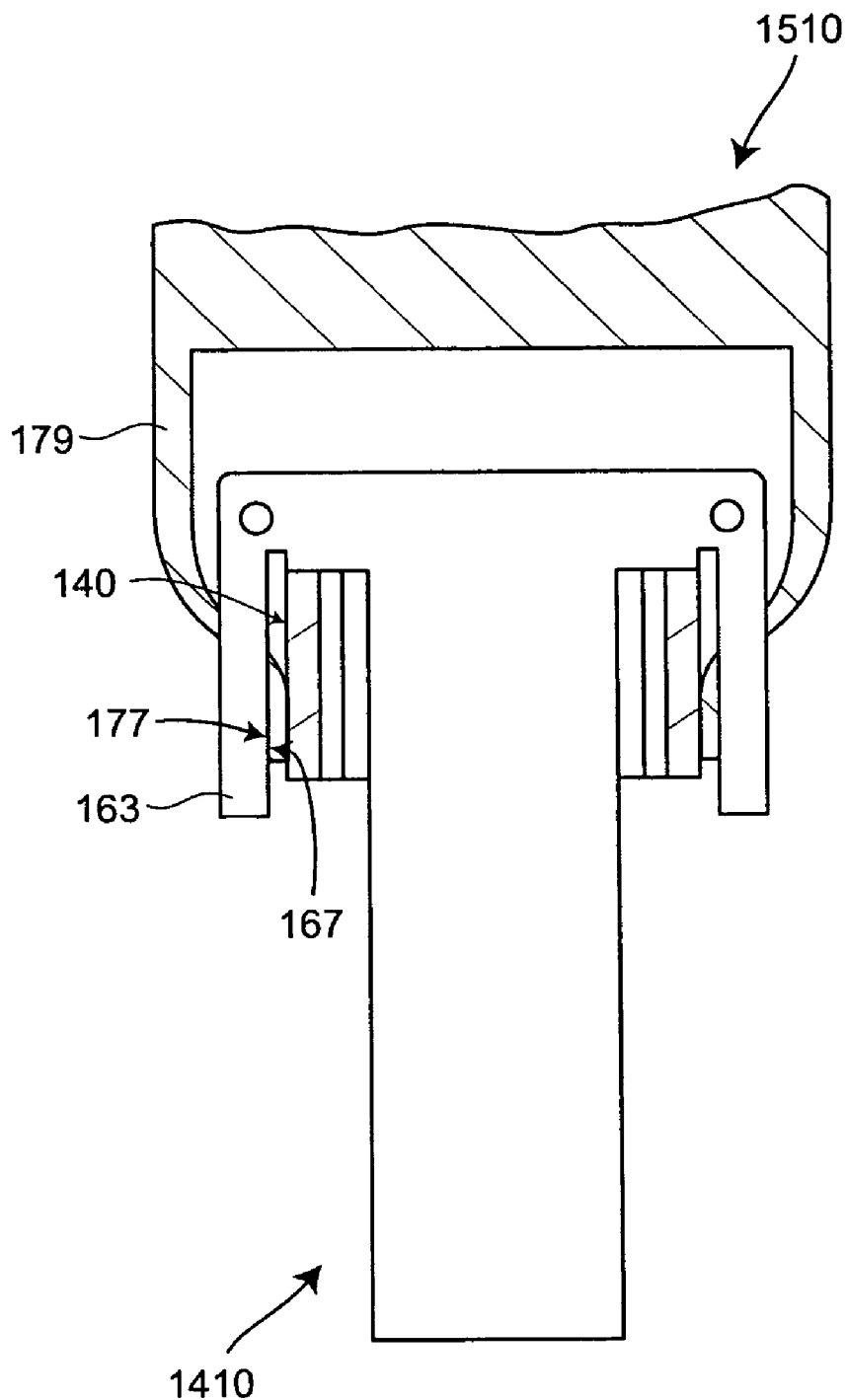
FIG. 29B shows the medical devices of FIG. 29A, but with the actuator(s) deactivated and the second medical device more securely attached to the first medical device, according to the teachings of the disclosure.

FIGS. 29A and 29B show an embodiment wherein the (first) medical device 1410 is associated with a second medical device 1510. The hooks, 163, 173 have been positioned in receptacles 175 and 275, respectively, of the second medical device 1510. In some embodiments, such as that shown in FIGS. 29A and 29B, the receptacles 175, 275 are provided for by a first flange 179 and second flange 279, respectively, but that is for illustrative purposes only, as the second medical device 1510 need not comprise such flanges. In FIG. 29A, the actuator 130 is in an activated state. In FIG. 29B, the actuator 130 is in a non-activated state so that a surface 167 of the hook 163 is brought into contact with a surface 177 of the second medical device 1510 such that the flange 179 is sandwiched between the hook 163 and the outer surface 140 of the nanoactuator 130. FIG. 29B shows then the first and second medical devices 1410 and 1510 more securely attached to one another.

Figure 30:
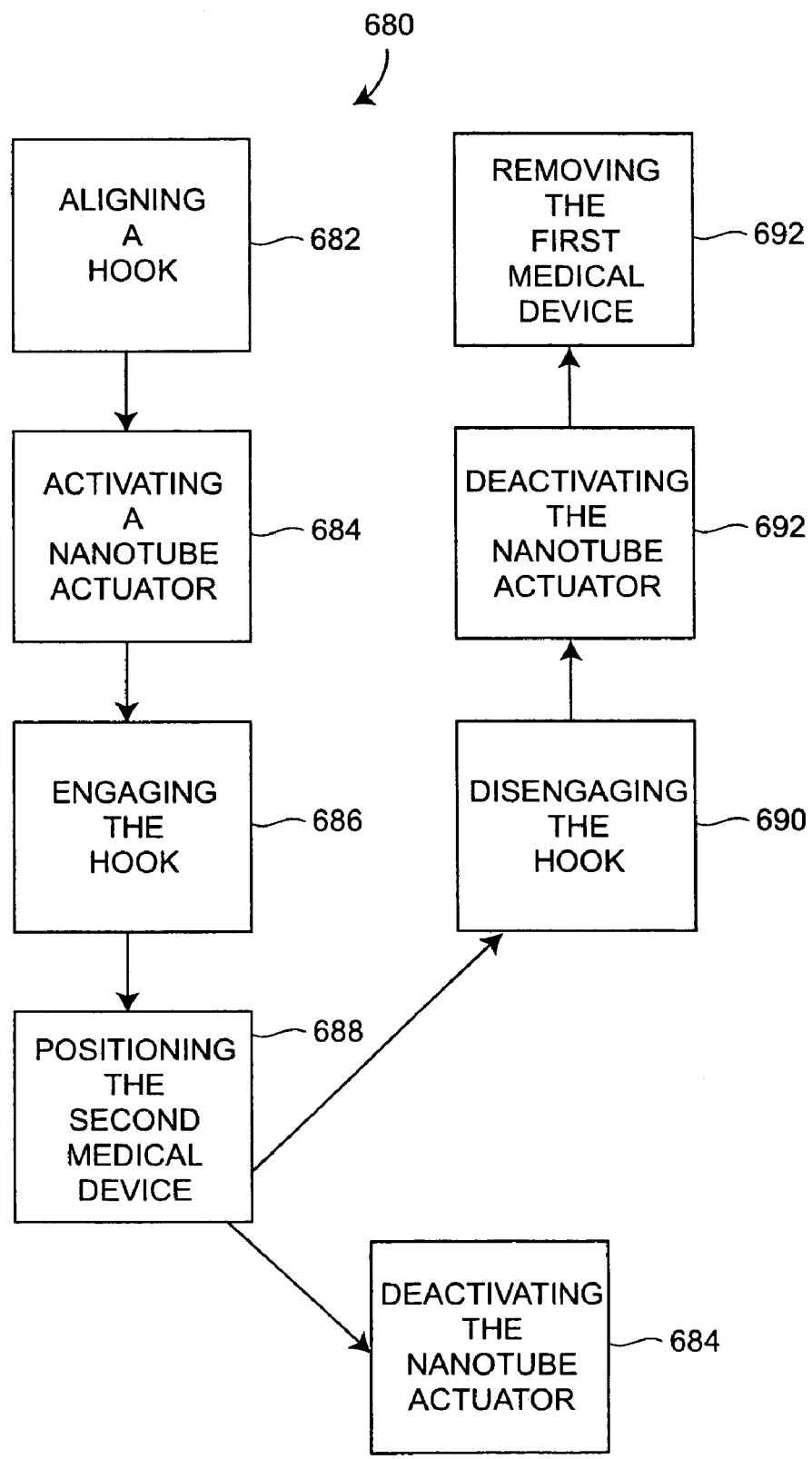
FIG. 30 is a flow chart showing a method of using a first medical device to position a second medical device, according to the teachings of the disclosure.

FIG. 30 depicts a method 680 for using a first medical device, e.g., 1410, to position a second medical device, e.g., 1510. The method 680 may comprise a step 682 of aligning a hook of the first medical device with a receptacle of the second medical device, a step 684 of activating a nanoactuator operatively associated with the hook of the first medical device, a step 686 of engaging the hook with the receptacle, and a step 688 of positioning the second medical device at a desired location within a body lumen. In some embodiments, the method 680 may further comprise a step 690 of disengaging the hook from the receptacle, and may further comprise a step 692 of deactivating the nanoactuator 692, and may still further comprise a step 694 of removing the first medical device. In some embodiments, the method 680 may further comprise, e.g., after the positioning step 688, a step 696 of deactivating the nanoactuator so that a surface of the hook is operatively associated with a surface of the second medical device., e.g., as shown in FIG. 29B.

In some embodiments of the first and second medical devices 1410 and 1510, as well as the method 680, the second medical device 1510 may comprise, but is not limited to, stents and aneurysm coils. In some embodiments, the hook 163 and nanoactuator 130 are operatively associated with the second medical device 1510 and the receptacle 175 is operatively associated with the first medical device 1410. In some embodiments, both first and second medical devices 1410, 1510 each comprise hooks, actuators and receptacles. In some embodiments, the hook 163 is absent and the actuator 130 itself acts as a "hook" so as being capable of insertion into a receptacle 175. In some embodiments, the method 680 is used for embolized stent retrieval.

The nanoactuator 130 of the present disclosure may be incorporated into any number of different devices that may be used in performing biopsies, and methods for employing the same. Description of some such devices are described herein.

Figure 31:
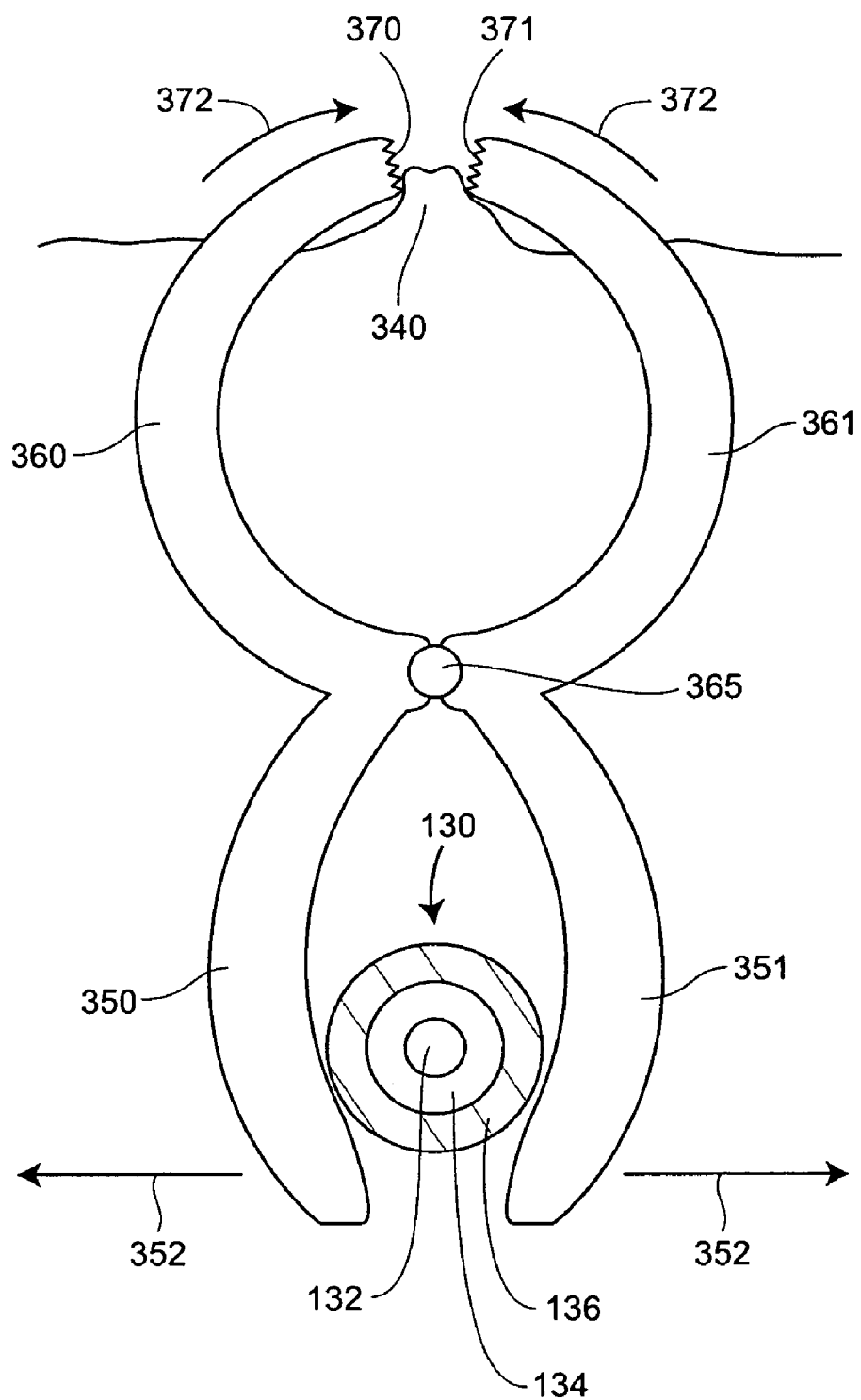
FIG. 31 is a perspective view of a medical device that may be used to obtain tissue samples for biopsies, the actuator of the medical device in a non-activated state according to the teachings of the disclosure.

FIG. 31 depicts a medical device 1610 that may be employed for obtaining a tissue sample 340 in a biopsy. A nanoactuator 130 is operatively associated with first and second handles 350, 351. The hands 350, 351 are operatively associated with arms 360, 361, hingedly attached at a hinge or pivot 365. The arms 360, 361 are provided with an appropriate cutting surfaces 370, 371, respectively, for obtaining a tissue sample 340. The arrows 352 and 372 denote the movement of the handles 350, 351 and arms 360, 361 respectively upon activation of the actuator 130, which brings together the surfaces 370, 371 to obtain a tissue sample.

Figure 32B:
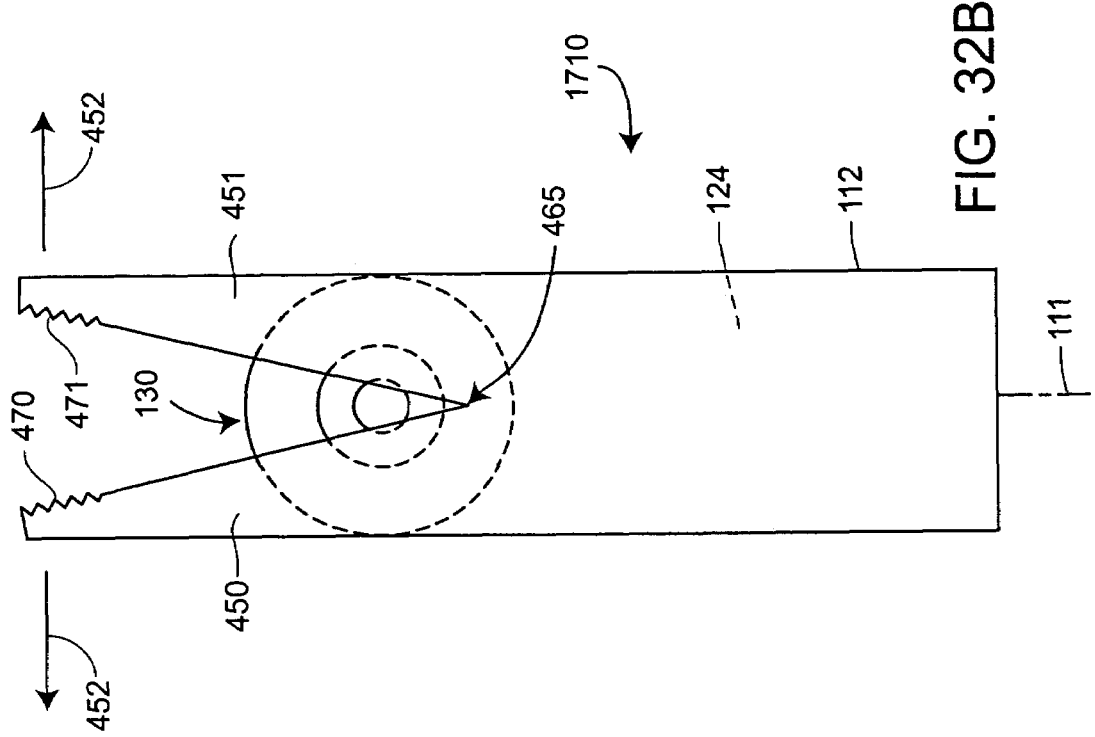
FIG. 32B is a perspective view of medical device shown in FIG. 32A, the actuator of the medical device in an activated state, according to the teachings of the disclosure.
Figure 32A:
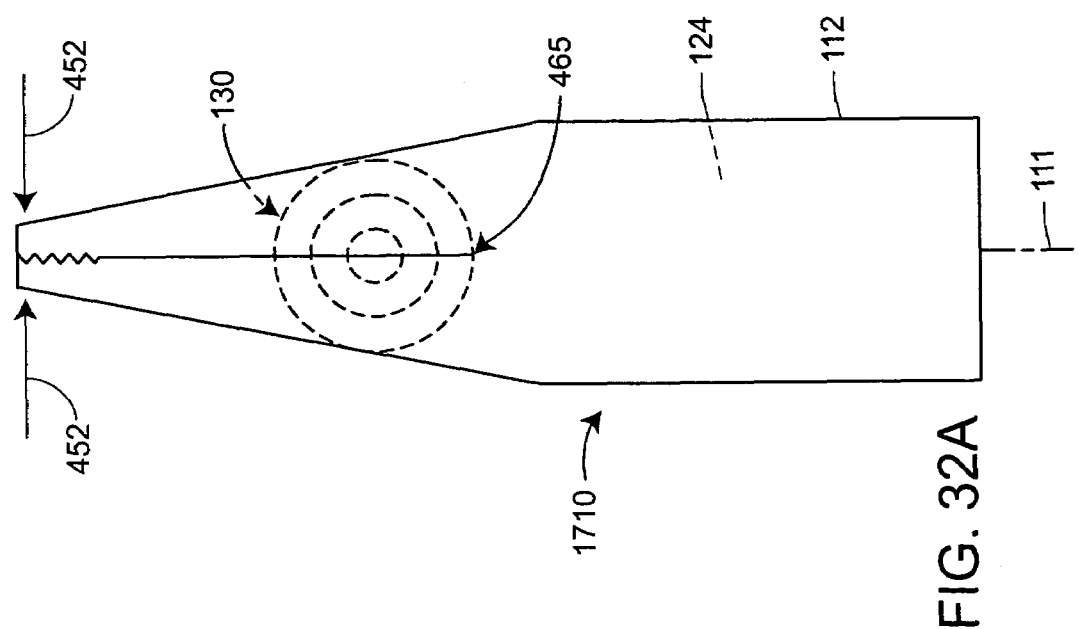
FIG. 32A is a perspective view of another medical device that may be used to obtain tissue samples for biopsies, the actuator of the medical device in a non-activated state, according to the teachings of the disclosure.

FIGS. 32A and 32B show a medical device 1710 that may be employed to obtain a tissue sample 340 when performing a biopsy. FIG. 32A shows the nanoactuator 130 in a non-activated state and FIG. 32B shows the nanoactuator 130 in an activated state. The medical device 1710 comprises first and second arms 450, 451 each provide with a surface 470, 471, respectively, designed for obtaining a tissue sample 340. The housing 112 and arms 350, 351 surround the nanoactuator 130 so that the actuator 130 is completely or partly within an interior 124 of the medical device 1710. The arrows 452 show the direction of movement and force when the actuator 130 is deactivated, and arrows 472 show the direction of the force when the actuator 130 is actuator. By positioning the surfaces 470, 471 about a tissue sample 340 with the actuator 130 activated, and then deactivating the actuator 130, a tissue sample 340 may be obtained. While the actuator 130 is shown perpendicular to the longitudinal axis 111 in FIGS. 32A and 32B that is for illustrative purposes only. In some embodiments the actuator 130 may be coaxial with the longitudinal axis 111 or have other orientations. The housing 112 and other components of the medical device 1710 may comprise superelastic material, shape memory metals, shape memory polymers, and nitinol.

Figure 33:
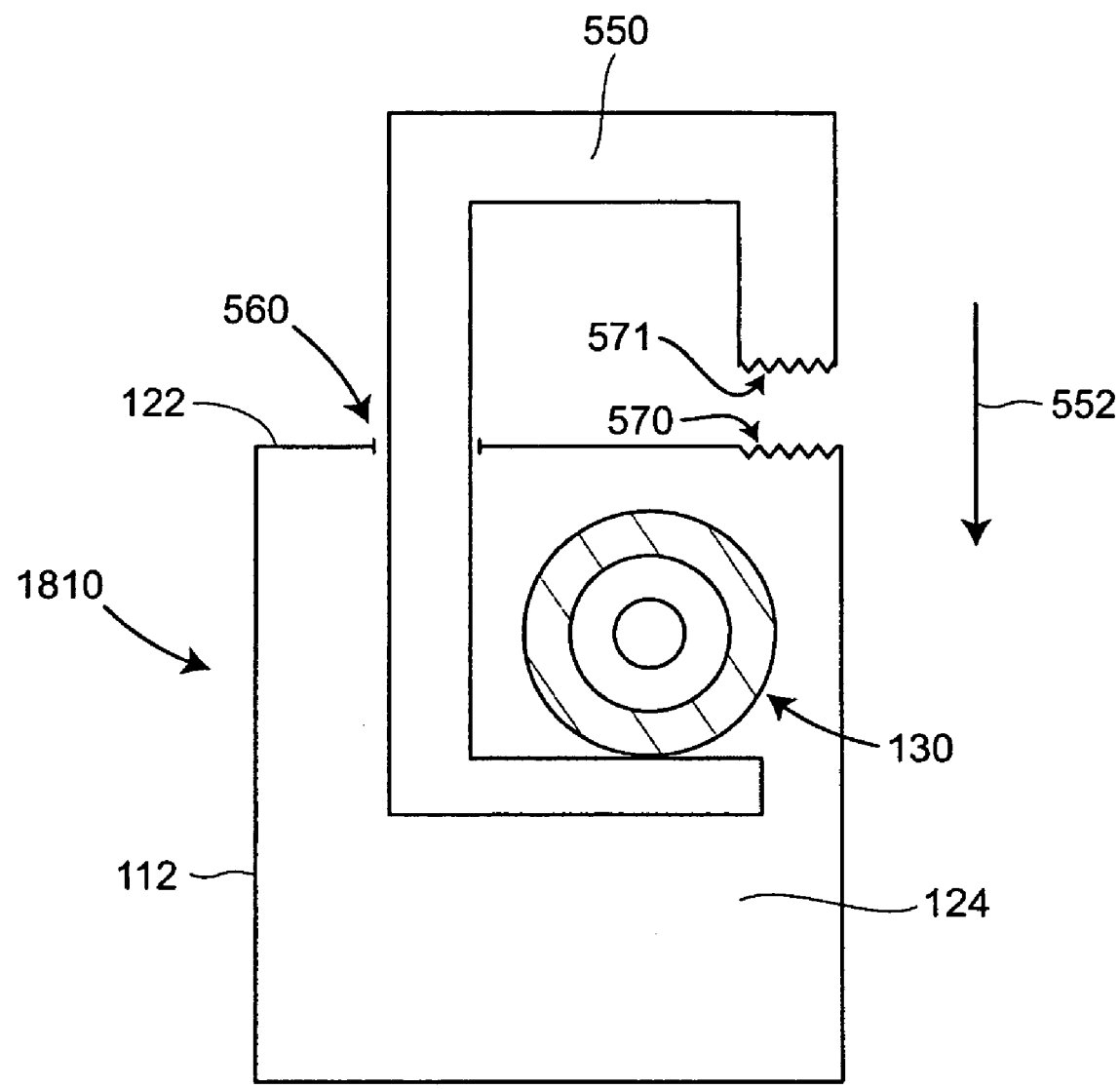
FIG. 33 is a sectional view of yet another medical device that may be used to obtain tissue samples for biopsies, the actuator of the medical device in a non-activated state, according to the teachings of the disclosure.

FIG. 33 shows a medical device 1810 that may be employed to obtain a tissue sample 340 for a biopsy. The medical device 1810 comprises an arm 550 operatively associated with a nanoactuator 130 and the housing 112. In FIG. 33, the actuator 130 is in a non-activated state. The housing 112 has a surface 570 and the arm 550 a surface 571 that may be brought together to obtain a tissue sample 340 by activating the actuator 130. Activating the actuator 130 forces the arm 550 down further into the interior 124 of the housing 112, an opening 560 allowing for movement of arm, at least in part, between the interior and exterior of the housing 112. The arrow 552 indicates the direction of the force 552 upon activation of the actuator 130.

Figure 34:
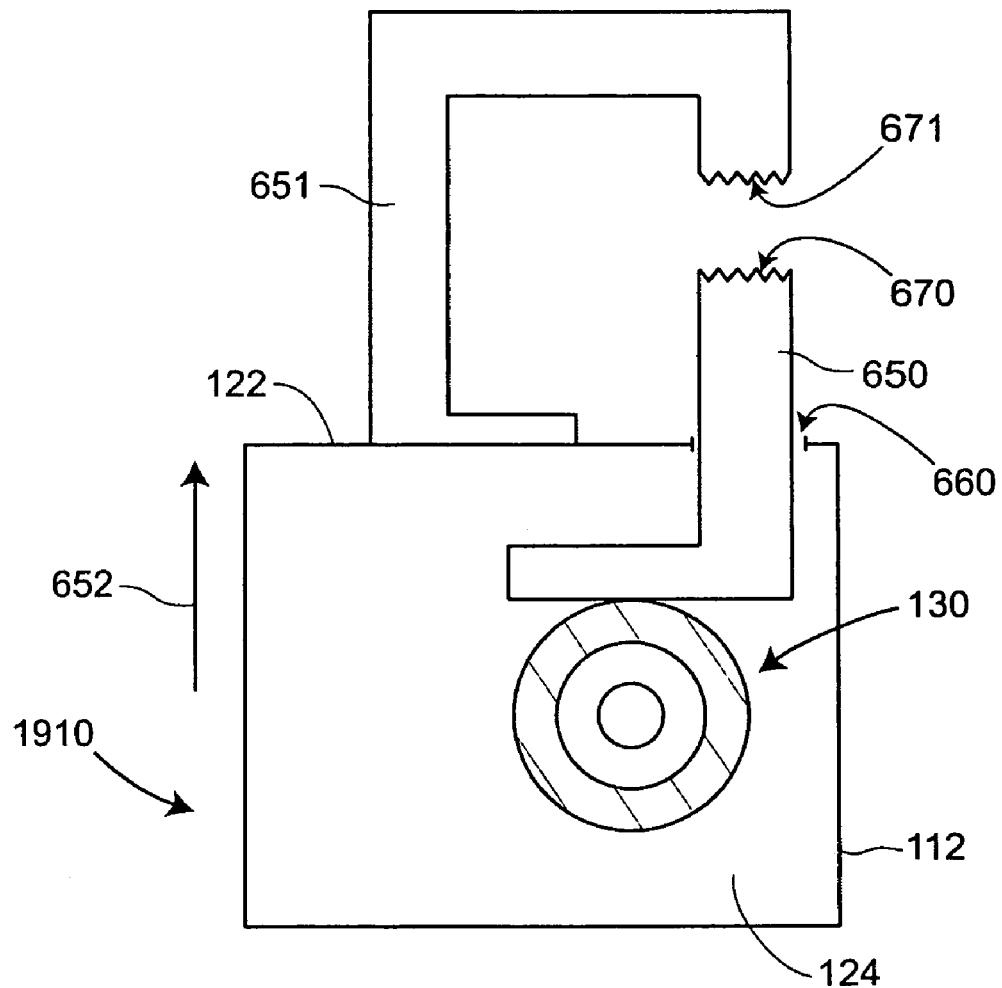
FIG. 34 is a sectional view of still another medical device that may be used to obtain tissue samples for biopsies, the actuator of the medical device in a non-activated state, according to the teachings of the disclosure.

FIG. 34 shows a medical device 1910 that may be employed to obtain a tissue sample 340 for a biopsy. A nanoactuator 130 is provided in the interior 124 of the housing 112. The actuator 130 is operatively associated with a first arm 650 that is partly in the interior 112 and partly in the exterior. A second arm 651 is operatively associated with an exterior surface 122. An opening 660 allows for movement of the first arm 650. The first arm 650 comprises a first surface 670 and the second arm comprises a second surface 671. Activation of the actuator 130 forces the first arm 650 upwards in the direction of the arrow 652 toward the second arm 651 bringing first and second surfaces 670, 671 together, allowing a tissue sample 340 to be obtained.

While the medical devices 1610, 1710, 1810 and 1910 are shown with a nanoactuator 130 in a circular or tubular configuration that is for illustrative purposes only as the actuator may also be provided in other configurations, including, but not limited to a segment of a circle or tube or as a flat sheet. The medical devices 1610, 1710, 1810 and 1910 may be provided at a distal end of a catheter 22 in a manner and placement analogous to that shown for the balloon assembly 28 of medical device 20. Such a placement allows for transport of the medical device to a location in the body where the tissue sample 340 is to be extracted.

Figure 35:
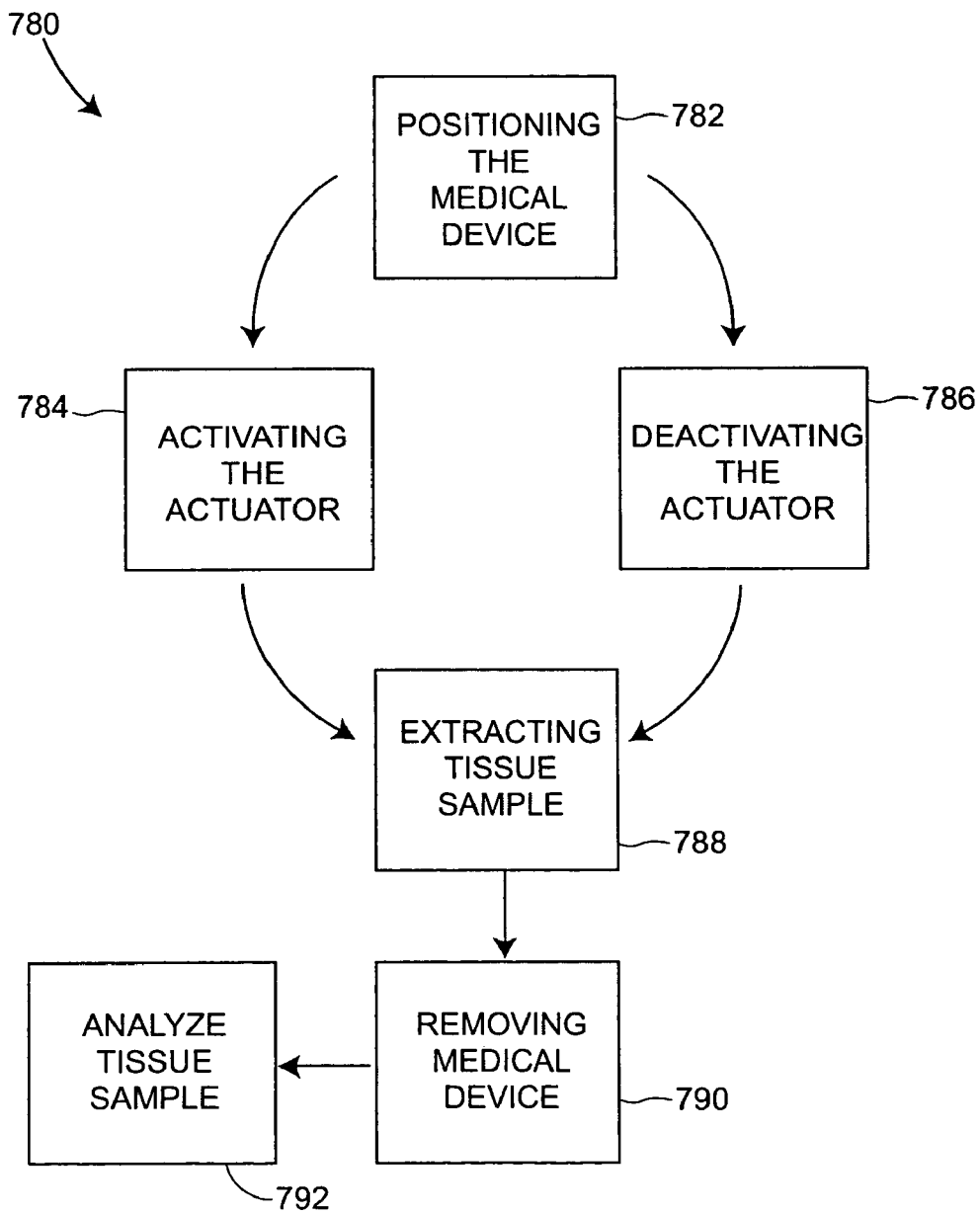
FIG. 35 is a flow chart showing a method of performing a biopsy, according to the teachings of the disclosure.

FIG. 35 demonstrates a method 780 for performing obtaining a tissue sample and performing a biopsy using a medical device, e.g., 1610, 1710, 1810 and 1910. A step 782 may comprise positioning the medial device in a location where one desires to extract a tissue sample. A step 784, which may comprise activating the actuator 130, or a step 786, which may comprise deactivating the actuator 130, may be performed. The step performed may or may not depend on the design on the medical device employed. A step 788 may comprise extracting a tissue sample. The further step 790 of removing the medical device may be performed. The step 792 of analyzing the extracted tissue sample may be performed. For example, one may analyze the tissue sample to determine whether a tumor from which the tissue sample is obtained is benign or malignant. In some embodiments, cell surface markers are assayed for using the tissue sample and appropriate antibodies.

The foregoing description and examples have been set forth merely to illustrate the disclosure and are not intended to be limiting. Nanoactuators according to the disclosure have a wide range of applications including those expressly or impliedly described. Components, elements, and embodiments described for one medical device or method are also applicable to other medical devices and methods of the disclosure. In some embodiments, components or elements may be omitted, added or altered. While the devices and methods of the present disclosure generally employ nanoactuators, other actuator technologies may be used instead or in addition to nanoactuators. The steps of the methods may be altered, e.g., in the ordering of steps. In some embodiments, steps may be omitted, repeated or additional steps added. The methods may be employed with the various devices described as well as other devices. The devices may be used in the methods described as well as other methods. Because modifications of the disclosed embodiments incorporating the spirit and substance of the disclosure may occur to persons skilled in the art, the disclosure should be construed to include everything within the scope of the appended claims and equivalents thereof.

What is claimed is:

1. A nano-actuated medical device, comprising: a housing sized to pass within a body lumen; and a nanoactuator operatively associated with the housing, said nanoactuator, upon electrical energization, actuating expansion of the housing within the body lumen.

2. The medical device of claim 1, wherein the nanoactuator comprises a first electrode, a separator operatively associated with the first electrode and a second electrode, the second electrode comprising nanopaper, and an electrolyte operatively associated with the separator and first and second electrodes.

3. The medical device of claim 2, wherein the nanopaper comprises carbon nanotubes.

4. The medical device of claim 2, wherein the separator comprises a porous membrane.

5. The medical device of claim 2, wherein the separator comprises a proton exchange membrane (PEM).

6. The medical device of claim 5, wherein the PEM is selected from the group consisting of a perfluorosulfonate ionomer and a sulfonated poly(styrene-isobutylene-styrene).

7. The medical device of claim 2, wherein the electrolyte comprises a chloride ion.

8. The medical device of claim 2, further comprising a first conductor associated with the first electrode, and a second conductor associated with the second electrode, the first and second conductors being operatively associated with a power source.

9. The medical device of claim 1, wherein the housing comprises a sheath.

10. The medical device of claim 1, wherein the medical device further comprises a stent, valve, distal protection device, aneurism coil, or vena cava filter.

* * * * *